(12) United States Patent
Hextall et al.

(10) Patent No.: US 11,332,520 B2
(45) Date of Patent: May 17, 2022

(54) HUMAN ANTIBODIES AND BINDING FRAGMENTS THEREOF TO TENASCIN

(71) Applicant: STERLING IP LIMITED, Marlow (GB)

(72) Inventors: Patrick Hextall, London (GB); Kim Suzanne Midwood, Oxford (GB); Eric Culbert, London (GB)

(73) Assignee: STERLING IP LIMITED, Marlow (GB)

( * ) Notice: Subject to any disclaimer, the term of this patent is extended or adjusted under 35 U.S.C. 154(b) by 299 days.

(21) Appl. No.: 16/076,267

(22) PCT Filed: Feb. 10, 2017

(86) PCT No.: PCT/EP2017/052974
§ 371 (c)(1),
(2) Date: Aug. 7, 2018

(87) PCT Pub. No.: WO2017/137542
PCT Pub. Date: Aug. 17, 2017

(65) Prior Publication Data
US 2020/0223910 A1 Jul. 16, 2020

(30) Foreign Application Priority Data
Feb. 10, 2016 (GB) .................................... 1602414

(51) Int. Cl.
| C07K 16/00 | (2006.01) |
| C12N 5/00 | (2006.01) |
| C12N 15/00 | (2006.01) |
| A61K 39/00 | (2006.01) |
| C07K 16/18 | (2006.01) |
| A61P 19/02 | (2006.01) |
| C12N 15/63 | (2006.01) |

(52) U.S. Cl.
CPC .............. *C07K 16/18* (2013.01); *A61P 19/02* (2018.01); *C12N 15/63* (2013.01); *A61K 39/00* (2013.01); *C07K 2317/21* (2013.01); *C07K 2317/55* (2013.01); *C07K 2317/565* (2013.01)

(58) Field of Classification Search
None
See application file for complete search history.

(56) References Cited

U.S. PATENT DOCUMENTS

2013/0045212 A1* 2/2013 Midwood ............... A61P 19/02
424/152.1

FOREIGN PATENT DOCUMENTS

| WO | 2010103289 A1 | 9/2010 |
| WO | 2016020702 A1 | 2/2016 |

OTHER PUBLICATIONS

Bendig M. M. Humanization of rodent monoclonal antibodies by CDR grafting. Methods: A Companion to Methods in Enzymology, vol. 8:83-93 (1995). (Year: 1995).*
Paul, W.E. Fundamental Immunology, Third Edition (textbook), "Fv Structure and Diversity in Three Dimensions" pp. 292-295; Raven Press, New York (1993). (Year: 1993).*
Houdebine, The methods to generate transgenic animals and to control transgene expression. Journal of Biotechnology, 98:145-160 (2002). (Year: 2002).*
Türkbeyler et al. "Prolidase Could Aetas a Diagnosis and Treatment Mediator in Lung Fibrosis" Inflammation, vol. 35, No. 5:1747-1752 (Oct. 2012). (Year: 2012).*
Morel, Mouse models of human autoimmune diseases: Essential tools that require proper controls, Pios Biology vol. 2/No. 8:1061-1064 (Aug. 2004). (Year: 2004).*
Salamanna et al. Improvement of an in vitro system to mimic the in vivo condition. Acta Histochemica 115:76-85 (2013). (Year: 2013).*
Justice et al. Using the mouse to model human disease: increasing validity and reproducibility, Disease, Models & Mechanisms 9: 101-103 (2016). (Year: 2016).*
International Search Report and Written Opinion for PCT International Application No. PCT/EP2017/082974 dated May 17, 2017.
Herold-Mende, et al., Clinical impact and functional aspects of tenascin-C expression during glioma progression, Int J Cancer. 98(3) ,2002 ,362-369.
Reardon, et al., Antitenascin-C monoclonal antibody radioimmunotherapy for malignant glioma patients, Expert Rev Anticancer Ther. 7(5) ,2007 ,675-687.

* cited by examiner

*Primary Examiner* — Elizabeth C. Kemmerer
*Assistant Examiner* — Regina M DeBerry
(74) *Attorney, Agent, or Firm* — Debora Plehn-Dujowich; Eckert Seamans Cherin & Mellott, LLC

(57) ABSTRACT

The present disclosure relates to antibodies and binding fragments to a Tenascin, in particular the FBG domain of a Tenascin, which are potentially less immunogenic than the parent antibody. The disclosure also relates to compositions comprising the antibody or binding fragment and use of any one of the same for diagnosis, prognosis and/or treatment of disorders such as those associated with chronic inflammation. The disclosure further provides methods of making the antibodies.

14 Claims, 12 Drawing Sheets
Specification includes a Sequence Listing.

FIGURE 2B
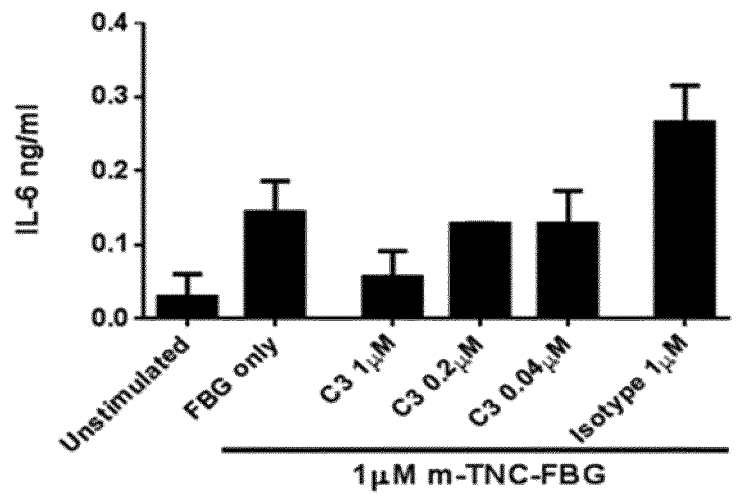
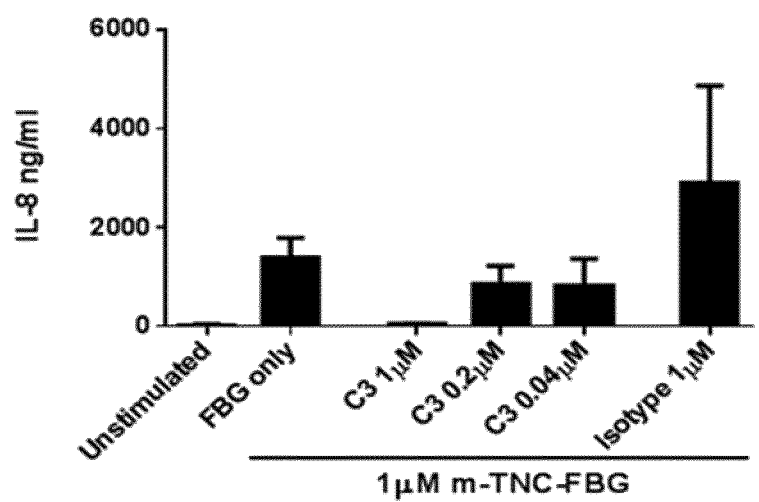
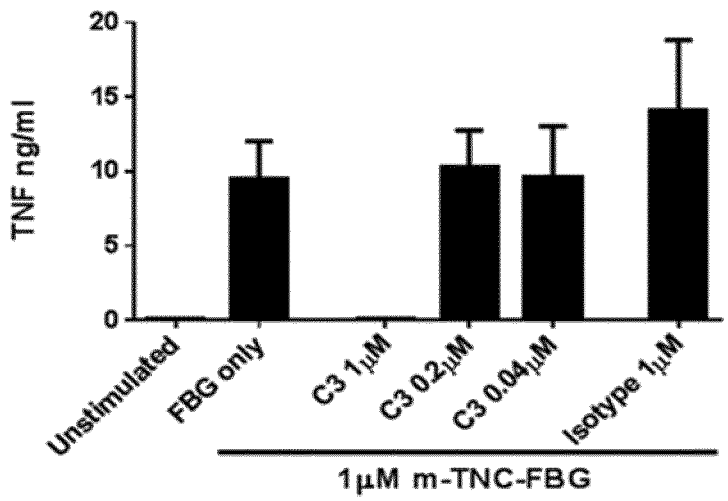

FIGURE 4
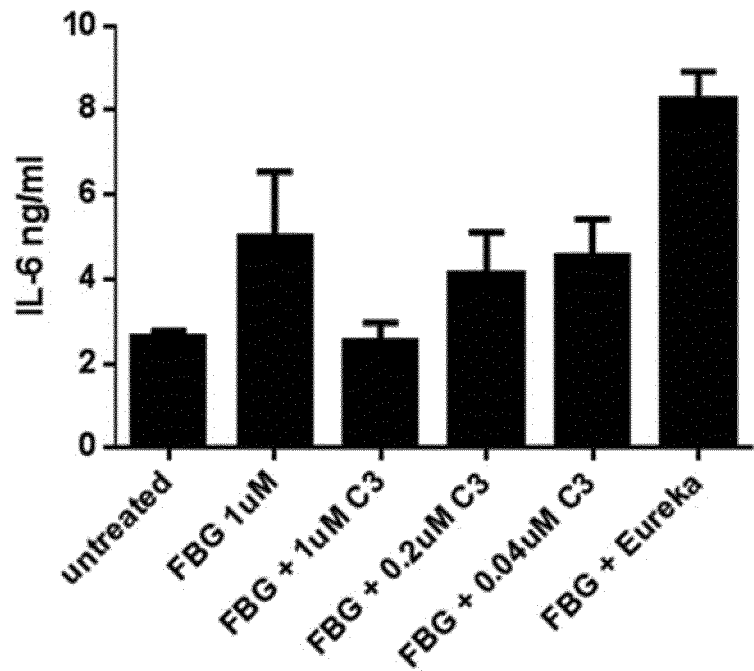
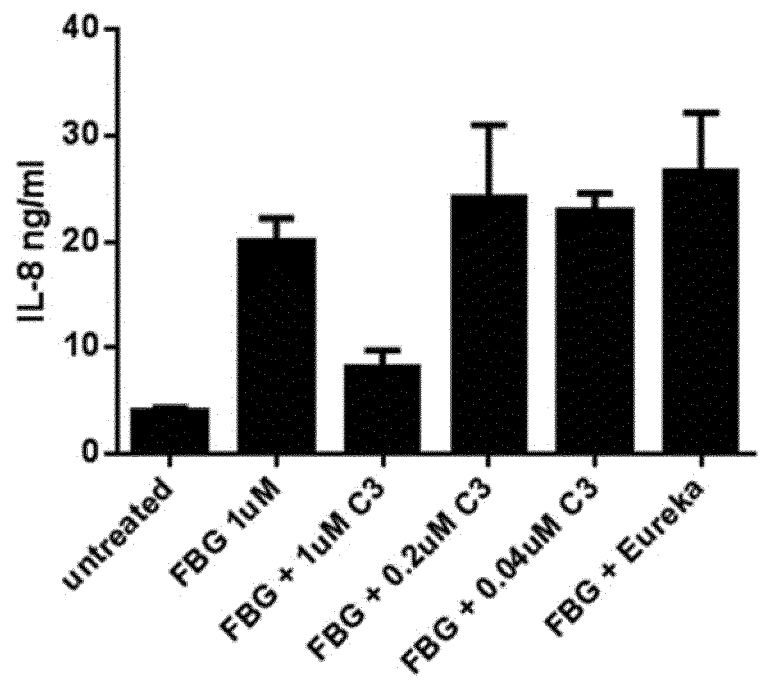

FIGURE 8

| Construct | N-term | Species | Primer name (F) | Primer sequence (F) | Primer name (R) | Primer sequence (R) |
|---|---|---|---|---|---|---|
| FBG-X | minus | human | 2561 | GGTACCTCGCGAATGCATCTAG | 2562 | CATGCAGGCCTCTGCAGTCG |
| FBG-X | plus | human | 2565 | TTTTTCCATGGCCCAGATTGGACTCCTGTACCCCTTCCCAAAGATTGCTCTCAGGC | 2562 | CATGCAGGCCTCTGCAGTCG |
| FBG-X | minus | mouse | 2561 | GGTACCTCGCGAATGCATCTAG | 2562 | CATGCAGGCCTCTGCAGTCG |
| FBG-X | plus | mouse | 2566 | TTTTTCCATGGCCCAGATTGGACTCCTGTACCCCTTCCCTCGCGACTGCTCACAG | 2562 | CATGCAGGCCTCTGCAGTCG |
| X-FBG | minus | human | 2567C | TTTTTGGATCCCATCATCATCACCATCACTTCCCAAAGATTGCTCTCAGGC | 2570 | TTTTTAAGCTTTTATTACGCCCGTTACGCCGACCCTC |
| X-FBG | plus | human | 2567 | TTTTTGGATCCCATCATCATCACCATCACATTGGACTCCTGTACCCCTTCCCAAAGATTGCTCTCAGGC | 2570 | TTTTTAAGCTTTTATTACGCCCGTTACGCCGACCCTC |
| X-FBG | minus | mouse | 2569C | TTTTTGGATCCCATCATCATCACCATCACTTCCCTCGCGACTGCTCACAG | 2571 | TTTTTAAGCTTTTATTACGCCCGTTCCGCCGACCTTC |
| X-FBG | plus | mouse | 2568C | TTTTTGGATCCCATCATCATCACCATCACATTGGACTCCTGTACCCCTTCCCTCGCGACTGCTCACAG | 2571 | TTTTTAAGCTTTTATTACGCCCGTTCCGCCGACCTTC |
| BamHI-His6-HindIII | N/A | N/A | 2574 | TTTTTGGATCCCATCATCATCACCATCACTAATAAAAG | 2575 | TTTTTAAGCTTTTATTAGTGATGGTGATGATGATGGG |
| His-FBG | plus | human | 2580 | TTTTTCTCGAGCATCATCATCACCATCACATTGGACTCC | 2570 | TTTTTAAGCTTTTATTACGCCCGTTACGCCGACCCTC |
| His-FBG | plus | mouse | 2580 | TTTTTCTCGAGCATCATCATCACCATCACATTGGACTCC | 2571 | TTTTTAAGCTTTTATTACGCCCGTTCCGCCGACCTTC | a b

| Region | Name | Residues | MW (kDa) |
|---|---|---|---|
| ◁ | TA | 23-45 | 15.6 |
| →◇◇◇◇◇◇◇◇◇◇◇◇ | EGF-L | 146-621 | 49.4 |
| 1 2 3 4 5 | TNIII1-5 | 622-1071 | 51.2 |
| 6 7 8 | TNIII6-8 | 1709-1973 | 29.4 |
| ● | FBG | 1974-2201 | 26.9 |
| 1 2 3 | TNIII1-3 | 622-891 | 31.4 |
| 3 4 5 | TNIII3-5 | 802-1071 | 30.6 |
| 5 6 7 | TNIII5-7 | 984-1885 | 29.7 |

HUMAN ANTIBODIES AND BINDING FRAGMENTS THEREOF TO TENASCIN

The present invention relates to antibodies or binding fragments thereof, specific the fibrinogen-like globe (FBG) domain of a tenascin, such as tenascin-C, compositions comprising the antibodies and use of any one of the same in the diagnosis, determination of prognosis, and/or treatment of disorders, for example disorders associated with chronic inflammation, as well as methods of making said antibodies.

CROSS-REFERENCE TO RELATED APPLICATIONS

The present application is a 35 U.S.C. 371 national phase application from, and claims priority to, International Application No. PCT/EP2017/052974, filed Feb. 10, 2017, and published under PCT Article 21(2) in English, which designated the U.S., and claims the benefit of priority from United Kingdom Patent Application No. GB1602414.3 filed on Feb. 10, 2016 each of which are incorporated by reference herein into this application in their entirety including all tables, figures and claims.

SEQUENCE LISTING

The instant application contains a Sequence Listing which has been submitted in ASCII format via EFS-Web and is hereby incorporated by reference in its entirety. Said ASCII copy, created on Nov. 17, 2019, is named 314641_00035_Sequence_Listing_ST25.txt and is 47 kilobytes in size.

BACKGROUND

Inflammation is the complex biological response of tissues to harmful stimuli, such as pathogens, tissue damage, or irritants. It is a protective attempt by the tissue to remove the injurious stimuli as well as initiate the healing process for the tissue. Abnormalities associated with inflammation comprise a large, unrelated group of disorders which underlie a variety of human diseases (inflammatory disorders). Examples of diseases with an inflammatory aspect include (but are not limited to) asthma, autoimmune disease, glomerulonephritis, allergy (hypersensitivities), cancer, inflammatory bowel diseases, reperfusion injury, rheumatoid arthritis and transplant rejection. Rheumatoid arthritis (RA) is a typical example of a chronic inflammatory condition.

Toll-like receptors (TLRs) play a key role in driving the production of inflammatory mediators in RA and blockade of TLR function may be of significant clinical benefit (reviewed in Brentano (2005) and O'Neill (2002)). This family of receptors forms an integral part of the immune system. TLRs mediate host defence against infection and injury by recognising both pathogen-associated molecular patterns (PAMPs) and damage-associated molecular patterns (DAMPs) (Matzinger (2002)). DAMPs are endogenous pro-inflammatory molecules generated upon tissue injury and include intracellular molecules released from damaged or necrotic cells, fragments of extracellular matrix (ECM) molecules or ECM molecules up regulated upon injury (reviewed in Bianchi (2007) and Gordon (2002)).

Upon activation, TLRs promote both innate and adaptive immune responses including stimulation of expression of pro-inflammatory cytokines and MMPs (Medzhitov (2002)). TLRs are expressed at high levels in synovial tissue from RA patients (Radstake (2004), Roelofs (2005), Sacre (2007), and (Sacre, 2008) and mice with targeted deletions or loss of function mutations in TLR4 are protected from experimental arthritis (Choe (2003) and Lee (2005).

Tenascin-C (TNC) is an ECM glycoprotein that is associated with tissue injury and wound repair. Tenascin-C is not normally expressed in healthy adult tissue but, in adults, is specifically and transiently up-regulated during acute inflammation and persistently expressed in chronic inflammation (reviewed in Chiquet-Ehrismann (2003)). Immunohistochemical studies show that little tenascin-C is expressed in normal human joints but levels are greatly increased in RA synovia, in areas of inflammation and fibrosis, specifically below the synovial lining, in the invading pannus and around blood vessels (Cutolo (1992), MacCachren (1992) and Salter (1993)). There is also a significant increase in tenascin-C levels in synovial fluid from RA patients (Chevalier (1994) and Hasegawa (2007)) and in RA cartilage (Salter (1993) and Chevalier (1994)).

Tenascin-C is a large hexameric protein of 1.5 million Da. Each chain comprises different domains, including an assembly domain (TA), EGF-like repeats (EGF-L), fibronectin type III-like repeats (TNIII) and a fibrinogen-like globe (FBG) (reviewed in Orend (2005)). The sequences of tenascin-C and its domains are shown in FIG. 9.

Tenascin-C has been shown to be an endogenous activator of TLR4 and it has been demonstrated that this molecule is required for destructive joint inflammation (WO2010/103289). Tenascin-C was shown to be capable of activating cells in the joint and the primary active domain of tenascin-C has been mapped to the fibrinogen-like globe (FBG), a 227 amino acid (26.9 kDa) globular domain at the C terminal of the molecule (Siri (1991)). Addition of FBG to synovial membrane cultures from RA patients enhanced the spontaneous release of pro-inflammatory cytokines. It also stimulated synthesis of TNF-α, IL-6 and IL-8 in primary human macrophages and IL-6 in RA synovial fibroblasts via activation of TLR4 and MyD88 dependent signalling pathways.

It has been shown that, as in the case of LPS, TLR4 expression is necessary for induction of cytokine synthesis by FBG. However, unlike LPS, neither CD14 nor MD-2 appears to be required for TLR-4 activation. CD14 is dispensable for activation of TLR4 by other ligands. It is not required for TLR4 to respond to lipid A in a MyD88 dependent manner (Jiang (2005)), fibronectin EDA (extra domain A) can activate mast cells even in the absence of CD14 (Gondokaryono (2007)) and hyaluronic acid activation of human monocytic THP-1 cells requires a complex of TLR4, CD44 and MD-2, but not CD14 (Taylor (2007)).

Formation of distinct receptor complexes by each TLR4 ligand may facilitate recruitment of different intracellular adapter/signalling molecules. This may account for the differential cellular responses we observe with FBG and LPS. Similarly, hyaluronic acid activation of the TLR4 and CD44 complex induces a pattern of gene expression in mouse alveolar macrophage cell lines that is different to LPS (Taylor (2007)).

The tightly regulated pattern of expression of tenascin-C makes it an attractive target for treating chronic inflammation. It is predominantly absent from healthy adults, however expression is specifically induced upon tissue injury. During acute inflammation tenascin-C is transiently expressed: induction often precedes inflammation and both mRNA and protein are absent from the tissue by the time inflammation is resolved (reviewed in Chiquet-Ehrismann (2003)).

Persistent expression of tenascin-C has now been shown to be associated with chronic inflammation. In addition to RA, increased tenascin-C levels are observed in other autoimmune diseases including multiple sclerosis (Gutowski (1999)) and Sjogrens disease (Amin (2001)), and in non-healing wounds and diabetic and venous ulcers (Loots (1998)). De novo synthesis of tenascin-C correlates well with the intensity of inflammation in diseases of the oral mucosa and plasma levels of tenascin-C are a reliable indicator for the activity of inflammatory bowel diseases before and after medication or surgery (reviewed in Chiquet-Ehrismann (2003)).

WO2010/103289 describes the use of agents for modulation of a chronic inflammatory response wherein the agent modulates the biological activity of tenascin-C and their use in treating conditions associated with chronic inflammation.

Clark et al. (1997) (52) describes a murine antibody specific for the FBG domain, which interfers with "lymphocyte rolling". The latter is believed to be a measure of cell migration, and unrelated to cell activation and production of inflammatory cytokines.

The inventors have designed antibodies and fragments thereof with properties that are suitable for use in therapy, in particular human antibodies, with very high affinity to the fibrinogen-like globe (FBG) domain of tenascin-C, and which neutralise the biological activity of FBG. These high affinity antibodies are useful in a variety of therapeutic methods, such as those which use anti-FBG antibody molecules in the diagnosis or treatment of tenascin-C related disorders, particularly those associated with chronic inflammation, including rheumatoid arthritis (RA). The antibodies are also useful in related diagnostic and prognostic methods. The antibodies are disclosed in WO2016/020702, incorporated herein by reference. This application discloses an antibody B12 from which an antibody 165_12_C3 (referred to herein as C3) was derived.

SUMMARY OF INVENTION

The present disclosure relates to a modified antibody or binding fragment thereof referred to C3* wherein a potential T cell epitope has been removed from the light chain framework to reduce the immunogenicity, and variants of the B12 antibody comprising said modification in the light chain.

Thus there is provided:
1. An antibody or binding fragment specific to Tenascin (for example specific to Tenscin C) comprising a sequence as shown in SEQ ID NO: 22 or 23, in particular, SEQ ID NO: 22.
2. An antibody or binding fragment according to paragraph 1 further comprising VH with CDRH1 of SEQ ID NO: 3, CDRH2 of SEQ ID NO: 4 and a CDRH3 independent selected from SEQ ID NO: 5, 12, 14, 16, 18, 24, 26, 28, 30 and 32, or a variant thereof wherein up to 5 amino acids are changed in the CDRs of the VH and VL.
3. An antibody or binding fragment according to paragraph 1 or 2 comprising a VH selected from SEQ ID NO: 6, 13, 15, 17, 19, 21, 25, 27, 29, 31, 33 and a variant thereof wherein up to 5 amino acids in the sequence are changed.
4. An antibody or binding fragment according to any one of paragraphs 1 to 3, which is a Fab or Fab' fragment
5. An antibody or binding fragment according to any one of paragraphs 1 to 3, which is a full length antibody.
6. An antibody or binding fragment according to paragraph 5, wherein the heavy chain has a sequence as shown in SEQ ID NO: 1.
7. An antibody or binding fragment according to paragraph 5 or 6, wherein the heavy chain has a sequence as shown in SEQ ID NO: 2.
8. A pharmaceutical composition comprising an antibody or binding fragment according to any one of paragraphs 1 to 7.
9. An antibody or binding fragment according to any one of paragraphs 1 to 7, or a pharmaceutical composition according to paragraph 8, for use in treatment
10. An antibody, binding fragment or composition for use according to paragraph 9, wherein the use is for the treatment of an inflammatory disorder, for example a chronic inflammatory disorder, for example a disorder disclosed herein, such as rheumatoid arthritis.
11. An antibody or binding fragment according to any one of paragraphs 1 to 7, or a pharmaceutical composition according to paragraph 8, for use in the manufacture of a medicament for the treatment of a chronic inflammatory response, for example a disorder disclosed herein, such as rheumatoid arthritis.
12. A method of treatment comprising administering a therapeutically effect amount of an antibody or binding fragment according to any one of paragraph 1 to 7 or a pharmaceutical composition according to paragraph 8.
13. A method according to paragraph 12, wherein the treatment is for an inflammatory disorder, for example a chronic inflammatory disorder, such as rheumatoid arthritis.
14. A polynucleotide encoding an antibody or binding fragment according to any one of paragraph 1 to 7.
15. A vector comprising a polynucleotide according to paragraph 13.
16. A host cell (for example a mammalian cell) comprising a polynucleotide of paragraph 12 or a vector of paragraph 13.
17. A process of producings (making) an antibody or binding fragment according to the present disclosure comprising the step of culturing a host cell, as defined in paragraph 16, to express said antibody or binding fragment.

Thus there is provided an antibody or binding fragment specific to Tenascin (for example specific to Tenscin C) comprising a light chain sequence as shown in SEQ ID NO: 1:

DIQMTQSPS<u>SLSAS</u>VGDRVTITCRASQYIQGFLNWYQQKPGKAPKLLIYDA

SNLETGVPSRFSGSGSGTDFTLTISSLQPEDFATYYCQQSYSTPQTFGQGT

KVDIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC

The antibody or binding fragment of the present disclosure further comprises a VH comprising CDRH1 of SEQ ID NO: 3, CDRH2 of SEQ ID NO: 4 and a CDRH3 independent selected from SEQ ID NO: 5, 12, 14, 16, 18, 20, 24, 26, 28, 30 and 32, or a variant thereof wherein up to 5 amino acids are changed in the CDRs of the VH and VL (in particular wherein the binding affinity for human Tenascin C in maintained at a similar value as that of the "parent/starting" antibody.

In one embodiment the VH in the antibody or binding fragment of the present disclosure is independently selected from SEQ ID NO: 6, 13, 15, 17, 19, 21, 25, 27, 29, 31, 33 and a variant thereof wherein up to 5 amino acids in the sequence are changed.

In one embodiment the VH is in a heavy chain as shown in SEQ ID NO: 2:

QVQLVESGGGLVQPGRSLRLSCAASGFTFDDYAMHWVRQAPGKGLEWVSGI

SGSGGSTYYADSVKGRFTISRDNAKNSLYLQMNSLRAEDTALYYCAKSYQS

DEDAFDIWGQGTMVTVSSASTKGPSVFPLAPCSRSTSESTAALGCLVKDYF

PEPVTVSWNSGALTSGVHTFPAVLQSSGLYSLSSVVTVPSSSLGTKTYTCN

VDHKPSNTKVDKRVESKYGPPCPPCPAPEFLGGPSVFLFPPKPKDTLMISR

TPEVTCVVVDVSQEDPEVQFNWYVDGVEVHNAKTKPREEQFNSTYRVVSVL

TVLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLYS

RLTVDKSRWQEGNVFSCSVMHEALHNHYTQKSLSLSLG

Thus in one embodiment the antibody of the present disclosure is a full length antibody or a molecule comprising a full length antibody, for example an IgG, such as IgG1, IgG2, IgG3 or IgG4.

In one embodiment the antibody or binding fragment thereof, is specific to an FBG domain, in particular an FBG domain of Tenascin-C.

In one embodiment the antibody or binding fragment according to the present disclosure have affinity to human Tenascin-C of 100 nM or higher affinity, such as 50 nM or higher, in particular 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 or 0.5 nM or higher affinity (which of course has a lower numerical value).

The antibodies and binding fragments according to the present disclosure may be less immunogenic that the corresponding parent antibody.

In one embodiment the antibody or binding fragment according to the present disclosure is conjugated to a payload.

The antibodies and binding fragments according to the present disclosure may express better than the corresponding parent antibody, for example 1.5, 2, 2.5 or 3 times better expression.

The antibodies and binding fragments according to the present disclosure have comparable properties, such as affinity, to the corresponding parent antibody. However, in some instances they antibodies or binding fragments herein may improved properties or activity over the corresponding parent antibodies.

DETAILED DISCLOSURE

"Antibody" as employed herein includes substantially intact antibody molecules, as well as chimeric antibodies, humanised antibodies, human antibodies (wherein at least one amino acid is mutated relative to the naturally occurring human antibodies), single chain antibodies, multispecific antibodies (such as bispecific antibodies), antibody heavy chains, antibody light chains, homodimers and heterodimers of antibody heavy and/or light chains, and antigen binding fragments and derivatives of the same.

By "antigen-binding fragment" we mean a functional fragment of an antibody that is capable of binding to the FBG domain of tenascin-C.

Antibody binding fragment and antigen binding fragment are employed interchangeably herein unless the context indicates otherwise.

Example of antibody binding fragments include to Fab, modified Fab, Fab', modified Fab', F(ab')2, Fv, Fab-Fv, Fab-dsFv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171.

Examples of a multispecific antibody comprising a fully length antibody include a DVD-Ig, IgG-scFv, scFv-IgG, and IgG-V.

IgG-scFv as employed herein is a full length antibody with a scFv on the C-terminal of each of the heavy chains or each of the light chains.

scFv-IgG as employed herein is a full length antibody with a scFv on the N-terminal of each of the heavy chains or each of the light chains.

V-IgG as employed herein is a full length antibody with a variable domain on the N-terminal of each of the heavy chains or each of the light chains.

IgG-V as employed herein is a full length antibody with a variable domain on the C-terminal of each of the heavy chains or each of the light chains DVD-Ig (also known as dual V domain IgG) is a full length antibody with 4 additional variable domains, one on the N-terminus of each heavy and each light chain.

In one embodiment the antibody binding fragment is or comprises a Fab or Fab' fragment.

Antibody binding fragments that comprise a Fab or Fab' fragment include Fabdab, Fab'dab, FabFv, Fab'Fv, FabdsFv, Fab-scFv, Fab'-scFv, Fab-(scFv)2, Fab'-(scFv)2, DiFab, DiFab'.

Fabdab as employed herein refers to a Fab fragment with a domain antibody appended to the heavy or light chain thereof, optionally via a linker.

Fab'dab as employed herein refers to a Fab' fragment with a domain antibody appended to the heavy or light chain thereof, optionally via a linker.

FabFv as employed herein refers to a Fab fragment with an additional variable region appended to the C-terminal of each of the following, the CH1 of the heavy chain and CL of the light chain see for example WO2009/040562. The format may be provided as a PEGylated version thereof see for example WO2011/061492, Fab'Fv as employed herein is similar to FabFv, wherein the Fab portion is replaced by a Fab'. The format may be provided as a PEGylated version thereof.

FabdsFv as employed herein refers to a FabFv wherein an intra-Fv disulfide bond stabilises the appended C-terminal variable regions, see for example WO2010/035012. The format may be provided as a PEGylated version thereof Fab-scFv (also referred to as a bibody) as employed herein is a Fab molecule with a scFv appended on the C-terminal of the light or heavy chain, optionally via a linker.

Fab'-scFv as employed herein is a Fab' molecule with a scFv appended on the C-terminal of the light or heavy chain, optionally via a linker.

DiFab as employed herein refers to two Fab molecules linked via their C-terminus of the heavy chains.

DiFab' as employed herein refers to two Fab' molecules linked via one or more disulfide bonds in the hinge region thereof.

DiFab and DiFab' molecules include chemically conjugated forms thereof.

Examples of linkers are disclosed in the sequence listing in SEQ ID NO: 45 to 86, and further includes the sequence PPP, and the hinge sequences disclosed in SEQ ID NO: 36 to 44.

The antibody or antigen-binding fragment, derivative or variant thereof according to the present disclosure may down-regulate the biological activity of, for example tenascin-C.

The antibody or antigen-binding fragment, derivative or variant thereof according to the present disclosure may be an inhibitor of transcription of, for example tenascin-C.

The antibody or antigen-binding fragment, derivative or variant thereof according to the present disclosure may be an inhibitor of translation of, for example tenascin-C.

Thus in one embodiment the antibody or binding fragment, derivate or variant thereof according to the present disclosure may down-regulate expression of the a tenascin, such as tenascin-C, in particular in vivo.

The antibody or antigen-binding fragment, derivative or variant thereof of the first aspect of the invention may be an inhibitor of the binding properties of tenascin-C. For example, the antibody or antigen-binding fragment, derivative or variant thereof may alter the conformation of tenascin-C such that it is no longer able to bind to its receptor or receptors, (in particular binding and/or activity of the FBG domain of tenascin-C is inhibited).

The antibody or antigen-binding fragment, derivative or variant thereof of the present disclosure may be a competitive binding inhibitor of tenascin-C. It will be appreciated by persons skilled in the art that the antibody or antigen-binding fragment, derivative or variant thereof may also inhibit the biological activity of the tenascin (such as tenascin-C) by blocking tenascin-C receptor function either directly (by acting as a tenascin-C receptor antagonist) or indirectly (by binding intermediary or assisting molecules).

The antibody or antigen-binding fragment, derivative or variant thereof of the first aspect of the invention may be an antagonist of the TLR-4 receptor. By an antagonist of TLR4 we include indirect antagonism. The antigen-binding fragment, derivative or variant thereof might prevent tenascin-C activation of TLR4 or also of any other receptor.

It will be appreciated by persons skilled in the art that inhibition of the biological activity of a tenascin (such as tenascin-C, in particular the FBG domain thereof) by an antibody or antigen-binding fragment, derivative or variant thereof of the invention may be in whole or in part. For example, the antibody or antigen-binding fragment, derivative or variant thereof may inhibit the biological activity of a tenascin (such as tenascin-C, in particular the FBG domain thereof) by at least 10%, preferably at least 20%, 30%, 40%, 50%, 60%, 70%, 80% or 90%, such as 100% compared to the biological activity of the tenascin (such as tenascin-C) on inflammatory cells which have not been exposed to the antibody or antigen-binding fragment, derivative or variant thereof.

In one embodiment, the antibody or antigen-binding fragment, derivative or variant thereof is monoclonal.

In one embodiment there is provided a polynucleotide encoding an antibody or binding fragment according to the present disclosure, for example the heavy and light chain of the antibody or binding fragment can be encoded on the same or different polynucleotide strand. Thus as employed herein "polynucleotide encoding) includes one polynucleotide encoding both the heavy and light chain or two separate polynucleotides one encoding the heavy chain and one encoding the light chain.

In one aspect, there is provided a vector comprising the polynucleotide as described above. General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

In another aspect, there is provided a host cell comprising the polynucleotide or vector as described above. Any suitable host cell/vector system may be used for expression of the DNA sequences encoding the antibody molecule of the present invention. Bacterial, for example *E. coli*, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector (and/or DNA) of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

In one embodiment the antibody or binding fragment is provided as a pharmaceutical formulation comprising one or more excipients, diluents and/or carriers. Accordingly, there is provided a pharmaceutical composition comprising an antibody or binding fragment as described above.

It will be appreciated by persons skilled in the art that the antibody or antigen-binding fragment, derivative or variant thereof of the invention will generally be administered in admixture with a suitable pharmaceutical excipient diluent or carrier selected with regard to the intended route of administration and standard pharmaceutical practice (for example, see *Remington: The Science and Practice of Pharmacy,* 19th edition, 1995, Ed. Alfonso Gennaro, Mack Publishing Company, Pennsylvania, USA).

For example, the antibody or antigen-binding fragment, derivative or variant thereof of the invention can be administered orally, buccally or sublingually in the form of tablets, capsules, ovules, elixirs, solutions or suspensions, which may contain flavouring or colouring agents, for immediate-, delayed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxy-propylcellulose (HPC), sucrose, gelatin and acacia.

Additionally, lubricating agents such as magnesium stearate, stearic acid, glyceryl behenate and talc may be included.

Solid compositions of a similar type may also be employed as fillers in gelatin capsules. Suitable excipients in this regard include lactose, starch, cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof. Alternatively, capsules may be filled with a liquid formulation.

The antibody or antigen-binding fragment, derivative or variant thereof of the invention can also be administered parenterally, for example, intravenously, intra-articularly, intra-arterially, intraperitoneally, intrathecally, intraventricularly, intrasternally, intracranially, intra-muscularly or sub-cutaneously, by intracavernosal injection, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets.

Example approaches: 1) Excipients such as buffers and detergents (usually Tween) are added to inhibit aggregation in aqueous formulations; 2) Freeze drying with appropriate excipients to provide bulk, stability and cosmetic appeal to the cake; 3) Formation of a glassy sugar using compounds such as trehalose.

For oral and parenteral administration, or other routes of administration, to human patients, the daily dosage level of the antibody or antigen-binding fragment, derivative or variant thereof of the invention will usually be from 1 µg to 1000 mg per adult (i.e. from about 0.015 to 15 mg/kg), administered in single or divided doses.

As an example, the dosage level may be from about 0.5 mg/kg to about 10 mg/kg, the administration regimen may be twice or three times weekly, the administration may be intravenous. In another embodiment the dosing regimen may be in the range once a week to once a month delivered intravenously or by subcutaneous injection.

The antibody or antigen-binding fragment, derivative or variant thereof of the invention can also be administered intranasally or by inhalation and are conveniently delivered, for example in the form of a dry powder inhaler, pump, spray or nebuliser an aerosol spray presentation from a pressurised container with the use of a suitable propellant, such as dichlorodifluoromethane, trichlorofluoro-methane, dichloro-tetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active antibody or antigen-binding fragment, derivative or variant thereof, such as using a mixture of ethanol and the propellant as the solvent, which may additionally contain a lubricant, such as sorbitan trioleate. Capsules and cartridges (made, for example, from gelatin) for use in an inhaler or insufflator may be formulated to contain a powder mix of an antibody or binding fragment of the invention and a suitable powder base such as lactose or starch.

Aerosol or dry powder formulations are suitably arranged so that each dose (or metered dose or 'puff') contains at least 1 µg of an antibody or antigen-binding fragment, derivative or variant thereof of the invention for delivery to the patient. It will be appreciated that the overall daily dose with an aerosol will vary from patient to patient, and may be administered in a single dose or, more usually, in divided doses throughout the day.

Alternatively, the antibody or antigen-binding fragment, derivative or variant thereof of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route.

For ophthalmic use, the antibody or antigen-binding fragment, derivative or variant thereof of the invention can be formulated as micronised suspensions in isotonic, pH adjusted, sterile saline, or, suitably, as solutions in isotonic, pH adjusted, sterile saline, optionally in combination with a preservative such as a benzylalkonium chloride. Alternatively, they may be formulated in an ointment such as petrolatum.

For application topically to the skin, the antibody or antigen-binding fragment, derivative or variant thereof of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

In one embodiment a sustained-release drug delivery system is employed, such as a microspheres. These are designed specifically to reduce the frequency of injections. An example of such a system is Nutropin Depot which encapsulates recombinant human growth hormone (rhGH) in biodegradable microspheres that, once injected, release rhGH slowly over a sustained period.

Alternatively, the antibody or antigen-binding fragment, derivative or variant thereof of the present invention can be administered by a surgically implanted device that releases the drug, for example directly to the required site.

Electroporation therapy (EPT) systems can also be employed for the administration of the antibody or antigen-binding fragment, derivative or variant thereof. A device which delivers a pulsed electric field to cells increases the permeability of the cell membranes to the drug, resulting in a significant enhancement of intracellular drug delivery.

The antibody or antigen-binding fragment, derivative or variant thereof can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of antibody or antigen-binding fragment, derivative or variant thereof delivery is the thermo-sensitive ReGel injectable. Below body temperature, ReGel is an injectable liquid while at body temperature it immediately forms a gel reservoir that slowly erodes and dissolves into known, safe, biodegradable polymers. The active drug is delivered over time as the biopolymers dissolve.

Antibody or antigen-binding fragment, derivative or variant thereof pharmaceuticals can also be delivered orally. One such system employs a natural process for oral uptake of vitamin B12 in the body to co-deliver proteins and polypeptides. By employing the vitamin B12 uptake system, the protein or polypeptide can move through the intestinal wall. Complexes are produced between vitamin B12 analogues and the drug that retain both significant affinity for intrinsic factor (IF) in the vitamin B12 portion of the complex and significant bioactivity of the "antibody" portion of the complex.

The composition of the present disclosure may further comprise at least one other agent.

Such a further agent may be an anti-inflammatory agent which includes but is not limited to non-steroidal anti-inflammatory agent (NSAID), a disease modifying anti-rheumatic drug (DMARD), a statin (including HMG-CoA reductase inhibitors such as simvastatin), a biological agent (biologicals), a steroid, an immunosuppressive agent, a salicylate and/or a microbicidal agent Non-steroidal anti-inflammatory agents include anti-metabolite agents (such as methotrexate) and anti-inflammatory gold agents (including gold sodium thiomalate, aurothiomalate or gold salts, such as auranofin). Biologicals include anti-TNF agents (including adalimumab, etanercept, infliximab, anti-IL-1 reagents, anti-IL-6 reagents, anti-B cell reagents (retoximab), anti-T cell reagents (anti-CD4 antibodies), anti-IL-15 reagents, anti-CLTA4 reagents, anti-RAGE reagents), antibodies, soluble receptors, receptor binding proteins, cytokine binding proteins, mutant proteins with altered or attenuated functions, RNAi, polynucleotide aptamers, antisense oligonucleotides or omega 3 fatty acids. Steroids (also known as corticosteroids) include cortisone, prednisolone or dexamethasone may also be employed in a combination therapy with an antibody or binding fragment according to the present disclosure. Immunosuppressive agents for use in a combination therapy according to the present disclosure include cyclosporin, FK506, rapamycin, mycophenolic acid. Salicylates for use in said combination therapy include aspirin, sodium salicylate, choline salicylate and magnesium salicylate. Microbicidal agents include quinine and chloroquine. For example, the antibody or antigen-binding fragment, derivative or variant thereof may be administered in combination with one or more of an NSAID, DMARD, or an immunosuppressant in treatment regime comprising an antibody or binding fragment according to the present disclosure.

In one embodiment there is provided an antibody or antigen-binding fragment of the present disclosure, or a derivative or variant thereof or composition as defined for use in therapy.

In one embodiment the antibody or antigen-binding fragment of the present disclosure, or a derivative or variant thereof or composition is employed for the treatment of a pathological condition such as an inflammatory condition/disorder and/or an autoimmune disease, for example a chronic inflammatory condition, in particular rheumatoid arthritis.

In one aspect of the invention there is provided the use of an antibody or antigen-binding fragment, derivative or variant thereof or composition according to the present disclosure in the manufacture of a medicament for the treatment and/or diagnosis of a pathological condition disclosed herein, for example chronic inflammatory condition.

In one embodiment there is provided a method of treating a pathological condition disclosed herein, such as chronic inflammatory condition comprising administering to a subject a therapeutically effective amount of an antibody or antigen-binding fragment, derivative or variant thereof or composition according to the present disclosure.

The pathological condition or disorder, may, for example be selected from the group comprising or consisting of arthritis such as rheumatoid arthritis, asthma such as severe asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis, hypochlorhydia and cancer, including breast cancer, lung cancer, gastric cancer, ovarian cancer, hepatocellular cancer, colon cancer, pancreatic cancer, esophageal cancer, head & neck cancer, kidney, and cancer, in particular renal cell carcinoma, prostate cancer, liver cancer, melanoma, sarcoma, myeloma, neuroblastoma, placental choriocarcinoma, cervical cancer, and thyroid cancer, and the metastatic forms thereof.

In one embodiment the autoimmune disease is selected from the group comprising or consisting of Acute disseminated encephalomyelitis (adem), acute necrotizing hemorrhagic leukoencephalitis, Addison's disease, adrenal insufficiency, hypocortisolism, alopecia areata, amyloidosis, ankylosing spondylitis, spondyloarthritis, Strumpell-marie disease, anti-GBM/anti-TBM nephritis, antiphospholipid syndrome (aps), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune lymphoproliferative syndrome (ALPS), Canale-Smith syndrome, autoimmune myocarditis, autoimmune oophoritis, autoimmune pancreatitis (AIP), autoimmune polyglandular syndromes (types I, II & III), autoimmune retinopathy (AR), autoimmune thrombocytopenic purpura (ATP), autoimmune thyroid disease, autoimmune urticaria, axonal/neuronal neuropathies, balo disease, Behcet's disease, bullous pemphigoid, cardiomyopathy, Castleman disease, coeliac disease, chagas disease, chronic inflammatory demyelinating polyneuropathy (CIDP), chronic recurrent multifocal ostomyelitis (CRMO), Churg-Strauss syndrome, cicatricial pemphigoid/benign mucosal pemphigoid (CP), Crohn's disease, inflammatory bowel disease, colitis, enteritis, ileitis, Cogans syndrome, cold agglutinin disease, congenital heart block, Coxsackie myocarditis, crest disease, cryoglobulinemia, demyelinating neuropathies, dermatitis herpetiformis, Duhring's disease, dermatomyositis, diabetes, type I, discoid lupus erythematosus (DLE), Dressler's syndrome, endometriosis, epidermolysis bullosa (EB) and eb acquisita (EBA), eosinophilic gastroenteritis, esophagitis, eosinophilic fasciitis, schulman's syndrome, erythema nodosum, experimental allergic encephalomyelitis, Evans syndrome, fibrosing alveolitis, giant cell arteritis (temporal arteritis), giant cell myocarditis, glomerulonephritis (nonproliferative: focal segmental glomerulosclerosis and membranous glomerulonephritis. proliferative: IgA nephropathy), goodpasture's syndrome, granulomatosis with polyangiitis (GPA) (formerly called Wegener's granulomatosis), Graves' disease, Guillain-Barré syndrome, Miller Fisher syndrome, acute motor axonal neuropathy, acute motor sensory axonal neuropathy, acute panautonomic neuropathy, Bickerstaffs brainstem encephalitis, Hashimoto's encephalitis, Hashimoto's thyroiditis, hemolytic anemia, Henoch-Schonlein purpura, herpes gestationis, hypogammaglobulinemia, idiopathic pulmonary fibrosis, idiopathic thrombocytopenic purpura (ITP), IgA nephropathy (IGAN), berger's syndrome, synpharyngitic glomerulonephritis, IgA pemphigus, IgG4-related sclerosing disease, immune-regulated infertility, inclusion body myositis, insulin-dependent diabetes mellitus, interstitial cystitis, Isaac's syndrome, neuromyotonia, juvenile arthritis, juvenile myositis, Kawasaki syndrome, Lambert-Eaton syndrome, leukocytoclastic vasculitis, lichen planus, lichen sclerosus, ligneous conjunctivitis, linear IgA dermatosis (LAD), pemphigoid, lupus (SLE), lyme disease, Meniere's disease, microscopic polyangiitis (MPA), mixed connective tissue disease (MCTD), monoclonal gammaopathy, Mooren's ulcer, Mucha-Habermann disease, multiple sclerosis, myasthenia gravis, myositis, narcolepsy, neuromyelitis optica (devic's), neuromyotonia, Isaac's syndrome (acquired, paraneoplastic, hereditary), neutropenia, ocular cicatricial pemphigoid, optic neuritis, oophoritis, opsoclonus-myoclonus syndrome, orchitis, palindromic rheumatism, pandas (pediatric autoimmune neuropsychiatric disorders associated with *Streptococcus*), paraneoplastic autoimmune multiorgan syndrome (PAMS), paraneoplastic cerebellar degeneration, paraneoplastic pemphigus (PNP), paroxysmal nocturnal hemoglobinuria (PNH), Parry Romberg syndrome, Parsonnage-Turner syndrome, pars planitis (peripheral uveitis), pempgigoid gestationis (PG), pemphigus vulgaris (PV), pemphigus folliaceus (PF), peripheral neuropathy, perivenous encephalomyelitis, pernicious anemia, Poems syndrome, polyarteritis nodosa (PAN), polymyalgia rheumatic, polymyositis, postmyocardial infarction syndrome, postpericardiotomy syndrome, progesterone dermatitis primary biliary cirrhosis, Hanot syndrome, primary sclerosing cholangitis (PSC), sclerosong cholangitis, psoriasis, psoriatic arthritis, pyoderma gangrenosum, pure red cell aplasia, Rasmussen's encephalitis, chronic focal encephalitis (CFE), Raynauds phenomenon, reactive arthritis, Reiter's syndrome, recoverin-associated retinopathy (RAR), reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, systemic sclerosis, sjogren's syndrome, sperm & testicular autoimmunity, stiff person/man syndrome, subacute bacterial endocarditis (SBE), Susac's syndrome, sympathetic ophthalmia, Takayasu's arteritis, temporal arteritis/giant cell arteritis, thromboangiitis obliterans, Buerger's disease, thrombocytopenic purpura (TTP), Tolosa-Hunt syndrome, transverse myelitis, ulcerative colitis, undifferentiated connective tissue disease (UCTD), uveitis, polymyalgia rheumatica, Takayasu's arteritis, temporal arteritis, Buerger's disease, cutaneous vasculitis, Kawasaki disease, polyarteritis nodosa, Behcet's syndrome, Churg-Strauss syndrome, cutaneous vasculitis, Henoch-Schönlein purpura, microscopic polyangiitis, Wegener's granulomatosis, golfer's vasculitis, vesiculobullous dermatosis, and Vitiligowegener's granulomatosis (now termed granulomatosis with polyangiitis (GPA).

In one embodiment the autoimmune disease is selected from the group comprising or consisting of ANCA vasculitis, IgA nephropathy (Berger's), pemphigus vulgaris/bullous pemphigoid, ITP, primary biliary cirrhosis, autoimmune thyroiditis (Grave's disease), hashimoto's disease, lupus nephritis, membranous glomerulonephritis (or membranous nephropathy), APS, myasthenia gravis, neuromyelitis optica, primary Sjögren's, autoimmune neutropaenia, autoimmune pancreatitis, dermatosmyositis, autoimmune uveitis, autoimmune retinopathy, Behcet's disease, IPF, systemic sclerosis, liver fibrosis, autoimmune hepatitis, primary sclerosing cholangitis, vitiligo, goodpasture's syndrome, pulmonary alveolar proteinosis, chronic autoimmune urticarial, psoriasis, rheumatoid arthritis, psoriatic arthritis, axial spodyloarthritis, transplantation (including GvHD), asthma, COPD, giant cell arteritis, refractory autoimmune cytopaenias, Evans syndrome (autoimmune haemolytic anaemia), type I diabetes, sarcoidosis, polymyositis, ulcerative colitis, Crohn's disease, coeliac disease, Waldenstrom's macroglobulinaemia, focal segmental glomerulosclerosis, chronic Lyme disease (Lyme borreliosis), lichen planus, Stiff person syndrome, dilated cardiomyopathy, autoimmune (lymphocytic) oophoritis, epidermolysis bullosa acquisita, autoimmune atrophic gastritis, pernicious anaemia, atopic dermatitis, atherosclerosis, multiple sclerosis, Rasmussen's encephalitis, Guillain-Barré syndrome, acquired neuromyotonia, stroke.

In one embodiment the antibody or antigen-binding fragment, derivative or variant thereof, composition, according to the present disclosure is employed for the treatment of a chronic inflammatory condition wherein the condition associated with inappropriate inflammation. Such conditions include, but are not limited to, rheumatoid arthritis (RA), autoimmune conditions, inflammatory bowel diseases, non-healing wounds, multiple sclerosis, cancer, atherosclerosis, sjogrens disease, diabetes, lupus erythematosus (including systemic lupus erythematosus), asthma, fibrotic diseases (including liver cirrhosis), pulmonary fibrosis, and UV damage and psoriasis.

Chronic inflammation is a debilitating and serious condition associated with many of the above diseases and is characterised by persistent inflammation at a site of infection or injury, or persistent inflammation of an unknown origin, or in relation to altered immune responses such as in autoimmune disease.

Thus in one embodiment the antibody or antigen-binding fragment, derivative or variant thereof, composition or method according to the present disclosure is employed in the treatment of a chronic inflammatory condition wherein the condition is associated with any condition associated with inappropriate inflammation. Such conditions include, but are not limited to, rheumatoid arthritis (RA), autoimmune conditions, inflammatory bowel diseases, non-healing wounds, multiple sclerosis, cancer, atherosclerosis, sjogrens disease, diabetes, lupus erythrematosus (including systemic lupus erythrematosus), asthma, fibrotic diseases (including liver cirrhosis), pulmonary fibrosis, UV damage and psoriasis.

In one embodiment the antibody or antigen-binding fragment, derivative or variant thereof, composition or method according to the present disclosure is employed in the treatment of a condition selected from axial spondyloarthropathy, primary biliary cholangitis, and allergy.

Rheumatoid arthritis (RA) is a typical example of, though by no means the only, a chronic inflammatory condition. RA is characterised by synovial inflammation and destruction of joint cartilage and bone mediated by persistent synthesis of pro-inflammatory cytokines and matrix metalloproteinases (MMPs).

In one embodiment the antibody or antigen-binding fragment, derivative or variant thereof or composition according to the present disclosure may be used, for example, for one or more of the following: to diagnose chronic inflammatory condition status in a subject; to assess the likelihood of a subject developing a chronic inflammatory condition; to determine the prognosis for a subject with a chronic inflammatory condition; to monitor disease progression of a chronic inflammatory condition; and/or to monitor effectiveness or response of a subject to a treatment for chronic inflammatory condition.

In one embodiment there is provided an antibody or antigen-binding fragment, derivative or variant thereof or composition according to the present disclosure for use in the diagnosis of a chronic inflammatory condition and/or the determination of prognosis of a patient with a chronic inflammatory condition.

In one embodiment there is provided a method of diagnosing a chronic inflammatory condition and/or determination of the prognosis of a patient with a chronic inflammatory condition comprising detecting the presence or absence or amount of the FBG domain of tenascin-C using an antibody or antigen-binding fragment, derivative or variant thereof or composition according to the present disclosure.

The prognosis determined may, for example, be a worsening of the chronic inflammatory condition. Alternatively, the prognosis may be a reduction (i.e. improvement) in the chronic inflammatory condition, or the prognosis may be that the chronic inflammatory condition stays the same (i.e. remains constant without worsening or improving).

In one embodiment the method of diagnosis is an in vitro method.

Thus in one embodiment an antibody or binding fragment according to the present disclosure is conjugate to label, for example a label that can detected, quatified and/or monitored such as a radiolabel or fluorescent label.

The appropriate treatment may comprise the administration of an effective amount of an an antibody or antigen-binding fragment, derivative or variant thereof, or composition according to the present disclosure optionally in combination with one or more of the following; DMARDS (such as methotrexate); anti-TNF drug; an anti-IL17 therapy; a T-cell co-stimulation modulator (such as Orencia™—abatacept): an interleukin-6 (IL-6) inhibitor (such as Actemra™—tocilizumab); an anti-CD20 antibody (such as Rituxan™—rituxumab; a B cell activating factor (such as anti-BAFF); an inhibitor of janus kinase (JAK) (such as Tofacitinib™); an inhibitor of spleen tyrosine kinase (Syk) (such as Fostamatinib™); antiTNC antibodies or antibodies to citrullinated tenascin-C domains; and/or an agent that modulates the biological activity of citrullinated and/or non-citrullinated tenascin-C.

In a particular embodiment, the appropriate treatment according to the present disclosure targets the FBG domain of tenascin-C.

In one embodiment, the method of diagnosis or method of determining the appropriate treatment comprises performing one or more of: immunoassays; spectrometry; western blot; ELISA; immunoprecipitation; slot or dot blot assay; isoelectric focussing; SDS-PAGE; antibody microarray; immunohistological staining; radio immuno assay (RIA); fluoro-immunoassay; and/or an immunoassay using an avidin-biotin or streptoavidin-biotin system.

In one aspect there is provided a kit of parts comprising:
(i) an antibody or antigen-binding fragment, derivative or variant thereof or composition according to the present disclosure.
(ii) administration means
(iii) instructions for their use In one embodiment, the kit may further optionally comprise
(iv) at least one other agent.

According to a further aspect of the invention there is provided a kit of parts for use in determining the chronic inflammatory condition status of a subject comprising:
(i) an antibody or antigen-binding fragment, derivative or variant thereof or composition according to the present disclosure; and
(ii) instructions for use Further Definitions "Amino acid change" as employed herein refers to substituting or deleting an amino acid, in particular substituting an amino acid refers to replacing an amino acid in sequences with a different (alternative) amino acid.

"Inflammation" as employed herein refers to local accumulation of fluid, plasma proteins, and white blood cells that is initiated by tissue injury, infection or a local immune response.

"Acute inflammation" as employed herein refers to the initial stages (initiation) of inflammation and the short-term transient inflammatory response immediately after injury, infection or local immune response. Typically, acute inflammation is rapidly resolved, lasting from a matter of minutes to no longer that a few days.

"Chronic inflammation" as employed herein refers to persistent and/or non-resolved inflammation. It is often associated with inappropriate destruction of healthy tissue. This may be progressive and last over a period of weeks or longer. Chronic inflammation is typically associated with persistent infection or disease including, but not limited to, autoimmune conditions.

"Chronic joint inflammation" as employed herein refers to persistent inflammation that is progressive and unremitting over a period of weeks to months, resulting in distortion of the affected joint and radiographic evidence of cartilage and bone destruction as observed in human disease (Kelly, Harris, Ruddy and Sledge, Textbook of Rheumatology 4th Edition).

In experimental murine models, chronic joint inflammation is characterised by inflammation that does not subside and causes inappropriate tissue destruction, even over a relatively short period of time. This is characterised (and can be identified) histologically by the prolonged presence of inflammatory cells in the synovium and joint space, chondrocyte death, and cartilage and bone erosion.

"Chronic inflammatory condition status", as employed herein includes the diagnosis of, determining the prognosis of and/or determining the appropriate treatment for a subject with or without a chronic inflammatory condition.

"Fragment" as employed herein refers to at least four amino acids, for example at least 4, 5, 6, 7, 8, 9, 10, 11, 12, 13, 14, 15, 16, 17, 18, 19, 20, 25, 30, 35, 40, 45, 50 amino acids.

The percent sequence identity between two polypeptides may be determined using suitable computer programs, for example the GAP program of the University of Wisconsin Genetic Computing Group and it will be appreciated that percent identity is calculated in relation to polynucleotides whose sequences have been aligned optimally.

The alignment may alternatively be carried out using the Clustal W program (as described in Thompson et al., 1994, Nuc. Acid Res. 22:4673-4680).

The parameters used may be as follows: Fast pairwise alignment parameters: K-tuple (word) size; 1, window size; 5, gap penalty; 3, number of top diagonals; 5. Scoring method: x percent. Multiple alignment parameters: gap open penalty; 10, gap extension penalty; 0.05. Scoring matrix: BLOSUM. Alternatively, the BESTFIT program may be used to determine local sequence alignments.

The term "subject" or "individual" means all animals including humans. Examples of subjects include humans, cows, dogs, cats, goats, sheep, and pigs. The term "patient" means a subject or individual having a disorder in need of treatment. Generally the subject and/or patient will be a human.

As used herein, 'pharmaceutical formulation' refers to a therapeutically effective formulation according to the present disclosure.

A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and/or prevent, a clinically significant deficit in the activity, function and response of the host/patient. Alternatively, a therapeutically effective amount is sufficient to cause an improvement in a clinically significant condition in a host/patient. As is appreciated by those skilled in the art, the amount of an active agent (such as an antibody or binding fragment according to the present disclosure) may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

The term payloads as used herein includes, for example, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Other payloads may include chelated radionuclides such as 111In and 90Y, Lu177, Bismuth213, Californium252, Iridium192 and Tungsten188/Rhenium188; or drugs such as but not limited to, alkylphosphocholines, topoisomerase I inhibitors, taxoids and suramin.

Other payloads include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *Pseudomonas* exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other payloads may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include 125I, 131I, 111In and 99Tc.

In another example the payload may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof "Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545).

Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971, WO2008/038024). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment or diFab which is PEGylated, i.e. has PEG (poly(ethyleneglycol)) covalently attached thereto, e.g. according to the method disclosed in EP 0948544 or EP1090037 (see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido)propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA2 (wherein m in the structure below is 5) and GL2-400MA (where m is 2) and n is approximately 450:

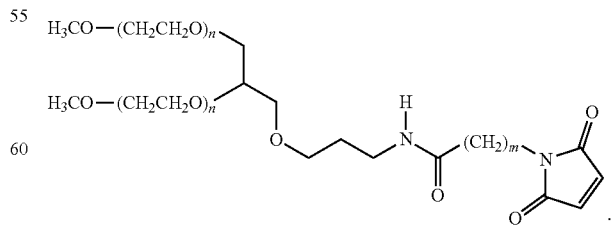

m is 2 or 5

That is to say each PEG is about 20,000 Da. Further alternative PEG effector molecules of the following type:

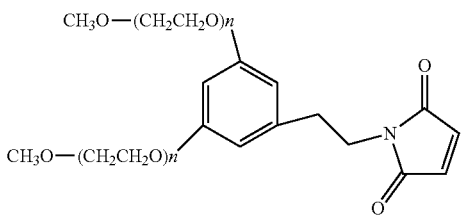

are available from Dr Reddy, NOF and Jenkem.

In one embodiment there is provided an antibody which is PEGylated (for example with a PEG described herein), attached through a cysteine amino acid residue at or about amino acid 226 in the chain, for example amino acid 226 of the heavy chain (by sequential numbering).

In the context of this specification "comprising" is to be interpreted as "including".

Aspects of the invention comprising certain elements are also intended to extend to alternative embodiments "consisting" or "consisting essentially" of the relevant elements.

Where technically appropriate, embodiments of the invention may be combined.

Technical references such as patents and applications are incorporated herein by reference.

Any embodiments specifically and explicitly recited herein may form the basis of a disclaimer either alone or in combination with one or more further embodiments.

Aspects of the present disclosure are described in the sequences and the figures, which may form the basis of an amendment. The disclosure of the figures and sequences have general application to the teaching of the present disclosure and not intended to considered as simply very specific combinations of features.

Examples embodying an aspect of the invention will now be described by way of illustration only, with reference to the following figures:

BRIEF DESCRIPTION OF FIGURES

FIG. 4 Graphs show effect on pro-inflammatory cytokine release by RA synovial fibroblasts stimulated with recombinant TNC-FBG after incubation with MAb C3.

FIG. 8 Table showing primer sequences used: Primer 2561 (SEQ ID NO: 87), Primer 2562 (SEQ ID NO: 88), Primer 2565 (SEQ ID NO: 89), Primer 2566 (SEQ ID NO: 90), Primer 2567C (SEQ ID NO: 91), Primer 2570 (SEQ ID NO: 92), Primer 2567 (SEQ ID NO: 93), Primer 2569C (SEQ ID NO: 94), Primer 2571 (SEQ ID NO: 95), Primer 2568C (SEQ ID NO: 96), Primer 2574 (SEQ ID NO: 97), Primer 2575 (SEQ ID NO: 98), and Primer 2580 (SEQ ID NO: 99).

EXAMPLES

Figure 1A:
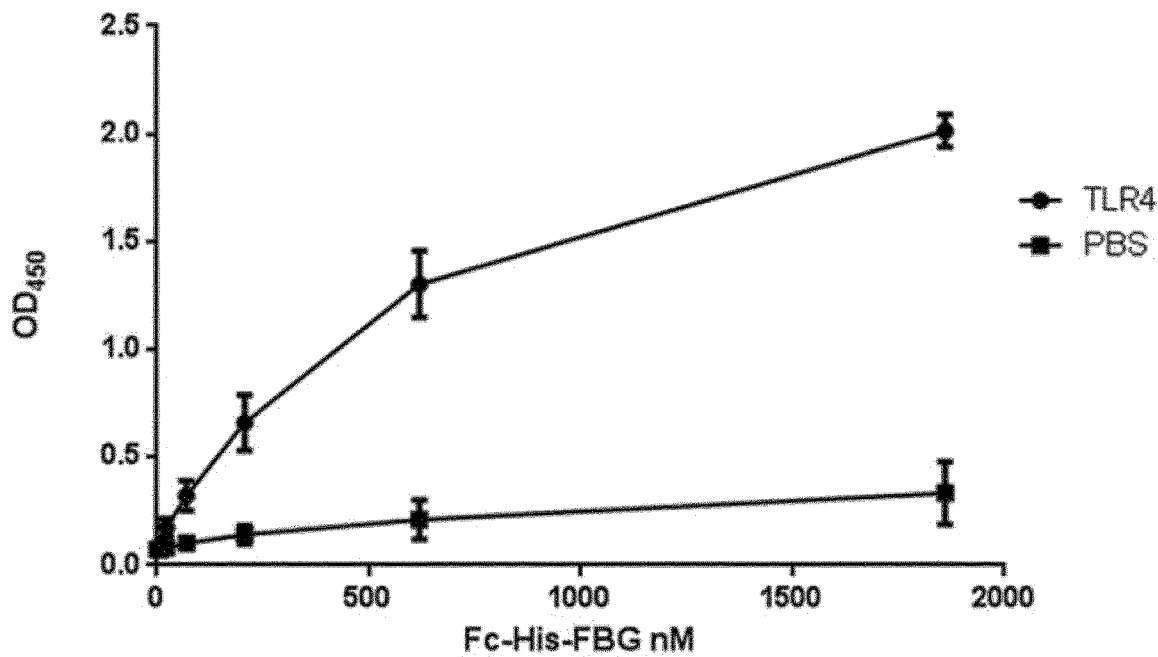
FIG. 1 (A) graph showing results of in vitro binding assay for TLR4 and Fc-His-FBG. (B) graph showing results of experiments to demonstrate ability of monoclonal Ab C3 to disrupt binding of FBG and TLR4 in vitro.

Example 1—Generation of Purified Tenascin-c FBG as Antigen and Assay Reagents

Purified soluble proteins containing the FBG domain of tenascin-C (TNC FBG) were generated for use as antigens in antibody selections and as reagents in subsequent screening and characterisation assays. To enable selection strategies for isolation of antibodies that bind tenascin-C of multiple mammalian species, a range of DNA expression constructs were synthesised, which incorporated the TNC FBG domain of either human, mouse, rat or dog. A human tenascin-R FBG construct was also prepared for identification of antibodies that displayed unwanted binding to this homologue. Constructs were produced as 6His-tagged proteins with either a rat CD4 or human IgG1 Fc tag coupled to either a C- or N-terminal FBG domain as described below.

Protein Expression Constructs

All synthetic DNA constructs for antigen expression were synthesised and sequence confirmed by Genscript (Piscataway, USA). FBG domains were cloned into the mammalian expression vectors pBIOCAM4 or BIOCAM5, which fuse the expressed domains with either a rat Cd4 (domains 3 and 4) tag (Chapple et al, 2006) or a human IgG1 Fc tag (Falk et al, 2012) respectively. The vectors were modified from the pCMV/myc/ER plasmid (Invitrogen) (Falk et al, 2012), which contains an endoplasmic reticulum (ER) signal sequence derived from the mouse VH chain, for secretion of expressed proteins. For all constructs which resulted in an N-terminal FBG (e.g. FBG-Fc-His or FBG-rCd4-His) the digested PCR products were ligated with NcoI/NotI cut pBIOCAM4 or pBIO CAMS vectors. For all constructs which resulted in a C-terminal FBG (e.g. Fc-His-FBG or rCd4-His-FBG), digested PCR products were ligated with BamHI/HindIII cut pBIOCAM4 or pBIOCAM5 vectors. The primers used to amplify the FBG domains are listed in FIG. 3. All constructs were sequence confirmed. To facilitate ELISA screening, an insert encoding a His-tag (primers 2574 and 2575) was cloned between the BamHI and HindIII sites (replacing the His-FLAG tag) for the expression plasmid with a FBG-X (N-terminal FBG) fusion. Full length tenascin C was cloned directly from the Genscript pUC57 plasmid by digestion with BstXI and BamHI and cloned into the BstXI/BamHI cut expression vector pFBG-Fc-His6. To create His-FBG constructs, primers were designed to PCR from an rCd4-His-FBG expression plasmid and the PCR product, encoding His-FBG, was digested with XhoI and HindIII and cloned into the XhoI/HindIII digested pBIO-CAM5.

Protein Expression and Cell Culture

Transfection quality plasmid DNA was prepared using the Machery Nagel Nucleobond Xtra Midi kit (740410.50, Fisher Scientific, UK). HEK293F suspension cells and Freestyle media, for antigen and antibody expression, and RPMI media were from Life Technologies (Paisley, UK). Transfection of HEK293F cells was carried out as described previously (Chapple et al, 2006).

Protein Purification and QC

Protein affinity purification employed either Ni-NTA agarose or immobilised recombinant protein A resin.

For purification of His-tagged proteins, culture supernatants were mixed with Ni-NTA agarose (1018240, Qiagen, Crawley, UK) for 1 h and the resin transferred to Proteus 1-step midi spin columns (Generon, UK) for centrifugation (200×g, 2 min). Unbound proteins were washed out with phosphate buffered saline (PBS) supplemented with 20 mM imidazole (pH 8). Bound proteins were eluted in fractions through addition of 300 mM imidazole in PBS (pH 8) and column centrifugation (200×g, 2 min). Pooled fractions containing eluted protein were placed in Gebaflex Midi dialysis tubes (Generon D010; molecular weight cut-off 3.5 kDa) and dialysed against PBS.

Fc-tagged proteins and antibodies expressed as human IgG4 were purified using protein A sepharose (PC-A25, Generon, Maidenhead, UK). Culture supernatants were clarified by centrifugation (2500×g, 15 min) and mixed with protein A sepharose overnight at 4° C. before transfer of the resin to Proteus 1-step midi spin columns (Generon, UK). Columns were centrifuged (200×g, 2 min) and washed with PBS to remove unbound protein. Fc-tagged or IgG4 proteins were eluted in fractions from the protein A with 0.2 M glycine (pH 2.8) into Tris-HCl (pH 8) by centrifugation (200×g, 2 min). Eluted fractions were pooled and dialysed against PBS in Gebaflex Maxi dialysis tubes (Generon D045; molecular weight cut-off 8 kDa).

Proteins were analysed for purity and concentration by SDS-PAGE (4-12% gel) and spectrophotometry (OD280 using theoretical extinction coefficient). Where purified proteins were used in cell-based assays the endotoxin content was first determined by limulus amoebocyte lysate chromogenic endotoxin assay (Pierce). Proteins were not used if endotoxin levels exceeded 1 endotoxin unit per milligram (i.e. 1 EU/mg).

Example 2—Isolation of Primary Anti-FBG Antibodies

Antibody Phage Display

Antibodies against tenascin-C FBG domain were isolated using the Iontas Ltd proprietary human antibody phage display library, which was constructed using DNA isolated from 43 human lymphocyte donors. Selections, phage rescues and subcloning into pSANG10 (Martin et al, 2006) were all performed as described previously (Schofield et al, 2007) using techniques that are well known in the art.

Two rounds of panning selections were performed on immobilised TNC FBG fused to human IgG1 Fc or rCd4 at either the N terminus of the fusion partner (e.g. FBG-Fc, FBG-rCd4) or at the C terminus (Fc-FBG, rCd4-FBG). Phage antibody libraries containing either kappa (κ) or lambda (λ) variable light chains ($V_L$) were panned separately to facilitate later sub-cloning to Fab expression vectors containing either constant light ($C_L$) kappa (κ) or lambda (λ) chains.

Polyclonal phage populations were prepared from the selected populations and were tested in ELISA (polyclonal phage ELISA) using ELISA plates coated with TNC FBG antigen or appropriate fusion partner (Fc or rCd4). After incubation with phage, plates were washed, and bound phage detected using peroxidase-conjugated anti-M13 antibodies. Enrichment of antigen-specific binders between rounds 1 and 2 of selection and a greater proportion of FBG binders compared to anti-Fc or -rCd4 phage in the round 2 output populations, indicating that the selections were successful.

Confirmation of scFv Binding to Antigen and Cross-Reactivity Assay by ELISA

Round 2 selection outputs were expressed as individual scFv clones to confirm antigen recognition in ELISA binding assays. Output populations were sub-cloned into the bacterial expression vector pSANG10 (Martin et al, 2006), transformed into E. coli BL21 (DE3), and individual transformants were induced in 96-well plates as described previously (Schofield et al, 2007). E. coli supernatants were collected and assayed for binding of scFv to TNC FBG using DELFIA-based ELISA, using europium-labelled anti-FLAG detection antibodies.

The most successful selections with the λ library were based on panning against the antigens rCd4-FBG and Fc-FBG (selections 147 and 148). For the κ library, the most successful selections were obtained with the antigens FBG-rCd4 (150), rCd4-FBG (152) and Fc-FBG (153). The 79 positive clones from this ELISA screen were selected for further analysis.

Cross-reactivity ELISA showed that 67/79 (85%) of anti-human FBG scFv were cross-reactive to mouse TNC FBG. DNA sequence analysis of the anti-FBG scFv indicated excellent sequence diversity. For example, selections 147 and 148 from the $V_L$ λ library contained 92% unique variable heavy ($V_H$) complementarity determining region 3 (CDR3) sequences, and selections 150, 152 and 153 from the $V_L$ κ library contained 67%, 91% and 100% unique variable $V_H$ CDR3 sequences, respectively.

A further 1425 clones isolated from the most effective selections were screened by ELISA and this resulted in the identification of an additional 401 scFv with FBG-binding specificity. These clones, together with the 79 scFv identified in initial ELISAs were chosen for further evaluation. The 1425 clones were further tested in a specificity ELISA in which each scFv was tested for binding to human Tenascin R FBG and also to human, mouse, rat and dog TNC FBG. Clones were ranked according to the ELISA signal obtained for binding to Tenascin C divided by the signal for Tenascin R FBG binding. The top 250 clones with a ratio above 50 were taken for subcloning and further analysis.

Example 3—Screening of Primary Anti-FBG Antibodies in a Functional Assay

Anti-FBG scFv were reformatted either as bivalent scFv-Fc or as monomeric Fabs for evaluation of their activity as inhibitors of FBG-evoked signalling in a whole cell assay system.

The top 50 anti-FBG scFv, ranked by primary ELISA signal, for each of the selections 147, 148, 150, 152 and 153 were sub-cloned into the mammalian expression plasmid pBIOCAM5 (Falk et al, 2012) as individual selection populations and expressed by transient transfection in HEK293F cells (Chapple et al, 2006). For Fab expression, pooled λ or κ scFv variable heavy (V$_H$) and variable light (V$_L$) inserts were cloned into a dual promoter Fab expression vector (pFab-dual-κ or pFab-dual-λ, depending on the light chain germ-line) using a proprietary Iontas Ltd protocol. Culture supernatants were screened for activity in the THP-1 cell assay and selected scFV-Fc and Fab hits were affinity purified for re-assaying and confirmation of inhibitory activity.

THP1-Blue™ Reporter Cell Assay

Tenascin-C has been shown to elicit the generation of cytokines in inflammatory cells and fibroblasts by interaction of the FBG domain with cellular TLR4 (Midwood et al, 2009). The receptor signalling cascade leading to generation of inflammatory cytokines such as TNFa, IL-8 and IL-6 involves activation of the transcription factor NF-κB. This process can be studied in 'reporter' cell lines modified to respond to NF-κB activation with generation of an easily measured protein signal. The THP1-Blue™ reporter cell line (InvivoGen; Toulouse, France) is derived from the human THP-1 monocyte cell line and stably expresses an NF-κB-inducible secreted alkaline phosphatase (SEAP) reporter construct. These cells also constitutively express cell surface TLR4, which enables the signalling activity of TNC FBG fusion proteins to be readily measured using colorimetric or fluorimetric quantitation of SEAP in culture supernatants using medium- to high-throughput assay methods.

Activity at low FBG concentrations is critical to the success of any screening assay; if the concentrations of FBG required to produce a robust increase in the reporter protein are too high then the expression levels and concentrations of scFv, Fc-ScFv or Fab constructs required to fully inhibit any such signal would be unacceptable for a screen. Fc-FBG produces a robust SEAP signal at low nM levels in this cell assay (CD4-FBG did not produce a response in this concentration range).

THP1-Blue™ cells were cultured and passaged in supplemented RPMI media according to supplier's protocols (www.invivogen.com/PDF/THP1_Blue_NF_kB_TDS.pdf), except that cells were grown in ultra-low attachment T75 flasks. For assays, THP1-Blue™ cells were added to 96-well tissue culture plates (100,000 cells/well) containing Fc-FBG (3 or 10 nM) in RPMI medium in a total volume of 170 μl. Culture supernatants containing expressed scFv-Fc or Fab, or affinity purified antibody in PBS, was added in a volume of 30 μl and cells were incubated for 18 h at 37° C. Supernatants were harvested and assayed for either SEAP using the Attophos AP fluorimetric quantitation system (S1000; Promega) or IL-8 content using the DuoSet ELISA development system (DY208; R&D Systems, UK) according to the supplier's instructions. Data were plotted and curves fitted using Prism software (GraphPad).

Screening of anti-FBG antibodies as HEK293F culture supernatants highlighted putative inhibitors of Fc-His-FBG evoked signalling in THP1-Blue™ cells of which 9 were confirmed when re-assayed as purified scFv-Fc or Fab. Fc-His-FBG is key to having the potency assays work. Monomeric FBG does not elicit any cytokine response in THP-1Blue and human cells.

Example 4—Functional Characterisation of Primary Anti-FBG Antibodies

ELISA Cross-Reactivity Assays

The panel of 9 human FBG signalling inhibitors identified in the THP1-Blue™ functional assay was evaluated by ELISA for cross-reactivity to rat, mouse, and dog FBG. Binding to the human tenascin-R FBG homologue was also determined. Assay wells were coated with human, rat, mouse, and dog TNC FBG-rCD4, or human TNR FBG-rCd4 fusion proteins and binding of Fabs was detected using anti-kappa or anti-lambda mAb followed by Europium-conjugated anti-mouse mAb. ELISA results revealed that the C3 antibody showed good cross-reactivity to other mammalian homologues of human TNC FBG, with lower apparent binding to human TNR FBG. These were:

Determination of Binding Affinity by Surface Plasmon Resonance

The affinity and association and dissociation kinetics of selected Fabs for binding to the human, rat and mouse TNC FBG, and human TNR FBG were measured by surface plasmon resonance (SPR) at 25° C. Experiments were performed using a BIAcore T100 instrument with CM5 sensor chip according to the protocol provided with the Human Fab Capture Kit (GE, 28-9583-25). Varying concentrations of rCd4-FBG were injected into a flow-cell with immobilised Fab and a reference flow-cell. After reference signal subtraction, the data was fitted to a global 1:1 fit using the T100 BIAevaluation software.

The calculated kinetic constants are shown in Table 3. The rank order of affinity of Fabs for human TNC FBG was B12 (110 pM)>. All Fabs displayed low nanomolar affinity for rodent TNC FBG, and affinities for human TNR FBG were typically greater than 60-fold lower than human TNR FBG.

Inhibitory Potency Assays

The potency of purified Fabs for neutralisation of huFc-His-FBG activity was determined in the THP1-Blue™ assay, using measures of TLR4-mediated secreted alkaline phosphatase and IL-8 cytokine production. Assays were conducted as described in Example 2, except that purified Fabs were added to assay wells at a range of concentrations (0.3-100 nM) to enable calculation of IC$_{50}$ values using Prism software (GraphPad).

The C3 antibody of the present disclosure is derived from an antibody referred to as B12.

TABLE 1

Anti-FBG Fab binding kinetic data determined by surface plasmon resonance (SPR) spectroscopy.

| Fab | FBG | Kinetics | | | |
| --- | --- | --- | --- | --- | --- |
| | | K$_D$ (nM) | K$_a$ (M$^{-1}$s$^{-1}$) ×10$^5$ | K$_d$ (s$^{-1}$) ×10$^{-4}$ | Steady State |
| B12 | Hu TNC | 0.111 | 26.62 | 3.0 | N/A |
| | Mu TNC | 13 | 52.15 | 675.5 | 18.7 |
| | Rat TNC | 7.9 | 94.59 | 747.9 | N/A |
| | Hu TNR | 33.9 | 13.96 | 472.5 | 36.1 |

K$_D$, equilibrium dissociation constant;
K$_a$, association constant;
K$_d$, dissociation constant Example 5—Generation and Isolation of Optimised Antibodies to huTNC FBG Domain Affinity Maturation by Targeted CDR Mutagenesis Anti-FBG antibody B12 was selected for affinity maturation. Targeted CDR mutagenesis was carried out by randomising VH and VL CDR3 residues in blocks of 6 amino acids using Kunkel mutagenesis (Fellouse and Sidhu, 2007; Kunkel et al., 1987; Sidhu and Weiss, 2004). Due to the longer VH CDR3s (10-16 residues) for the given clones randomisation was done in three overlapping blocks and the VL CDR3s (9 residues) were randomised in two overlapping blocks. Randomisations were carried out using NNS (N=A/G/C/T and S=G/C) degenerate primers that could encode any of the 20 amino acids (and only a single amber stop codon) at a given position from 32 codon combinations. The following library was created.

TABLE 2

Estimated sizes of the CDR3 randomised libraries

| Library | Sub library | Size | Combined size |
|---|---|---|---|
| B12 VH | B12 VH 3.1 | $1.8 \times 10^9$ | $6.1 \times 10^9$ |
|  | B12 VH 3.2 | $1.6 \times 10^9$ |  |
|  | B12 VH 3.3 | $1.7 \times 10^9$ |  |
| B12 VL | B12 VL 3.1 | $2.6 \times 10^9$ | $7.7 \times 10^9$ |
|  | B12 VL 3.2 | $5.1 \times 10^9$ |  |

High Stringency Phage Display Selections

Phage-antibody selections on streptavidin Dynabeads were performed as described previously (Dyson et al, 2011). Multiple rounds of solution-phase selections were carried out on biotinylated rCd4-His-FBG to enrich for affinity improved clones. The optimum antigen concentrations for each round were determined empirically by selecting against a range of antigen concentrations and comparing the output numbers with a no-antigen control. The stringency of selection was increased by reducing the amount of antigen used in each round. No further rounds of selection were carried out after the selection window (the fold difference between phage titres from selection outputs and no antigen control) dropped below 10. Hence, three rounds of selection were carried out on biotinylated human rCd4-His-FBG for all libraries except B12 which was subjected to a fourth round of selection due to the large selection windows observed at round 3. All libraries were subjected to deselection against streptavidin beads and tenascin-R (100 nM for rounds 1 to 3 and 1 nM for round 4) at each round of selection to avoid unwanted cross reactivity to streptavidin or tenascin-R. In addition, a hybrid selection strategy in which the human and mouse antigens were alternated between rounds of selection was performed for the B12 randomised libraries only. The reason for performing this extra selection on the B12 libraries was the large difference in affinity observed for the B12 parental antibody binding to human and mouse rCd4-his-FBG. Furthermore, an additional round of selection was carried out to select for antibody clones with superior off-rates. In off-rate selections, phage were allowed to bind to the biotinylated antigen (1 nM in this case), and a large excess of non-biotinylated antigen (500 nM) was subsequently added to the reaction and incubated for 20 h or 40 h. The non-biotinylated antigen serves as a competitor and captures the phage antibodies that dissociate from the biotinylated antigen, i.e. only the antibodies with longer off-rates will be recovered at the end of the selection (Hawkins et al., 1992; Zahnd et al., 2010). The output phage titres for each round of selection together with calculated selection windows are shown in Tables 3 to 5 below.

TABLE 3

Selection output titres. Round 1 selections. Phage output titres were determined as described previously (Schofield et al, 2007).

| CDR3 randomised libraries | 10 nM Selection | 1 nM Selection | 0 nM Selection | Selection window for 10 nM selection | Selection window for 1 nM selection |
|---|---|---|---|---|---|
| B12 VH | $6 \times 10^7$ | $2.6 \times 10^7$ | $1 \times 10^5$ | 600 | 260 |
| B12 VL | $6 \times 10^7$ | $5 \times 10^7$ | $2 \times 10^5$ | 300 | 250 |

TABLE 4

Selection output titres. Round 2 selections. Phage output titres were determined as described previously (Schofield et al, 2007).

| CDR3 randomised libraries | 200 pM Selection | 50 pM Selection | 0 nM Selection | Selection window for 200 pM selection | Selection window for 50 pM selection |
|---|---|---|---|---|---|
| B12 VH | $1 \times 10^8$ | $6.75 \times 10^7$ | $2 \times 10^4$ | 5000 | 3375 |
| B12 VL | $1.2 \times 10^8$ | $8.1 \times 10^7$ | $4 \times 10^4$ | 3000 | 2025 |
| B12 VH on mu TNC FBG | $7 \times 10^6$ |  | $2 \times 10^4$ | 350 |  |
| B12 VL on mu TNC FBG | $7.5 \times 10^6$ |  | $4 \times 10^4$ | 187 |  |

TABLE 5

Selection output titres. Round 3 selections. Phage output titres were determined as described previously (Schofield et al, 2007).

| CDR3 randomised libraries | 5 pM Selection | 1 pM Selection | 0 nM Selection | Selection window for 5 pM selection | Selection window for 1 pM selection |
|---|---|---|---|---|---|
| B12 VH | $1.5 \times 10^7$ | $4 \times 10^6$ | $<1 \times 10^5$ | >150 | >40 |
| B12 VL | $2.7 \times 10^7$ | $3.5 \times 10^6$ | $<1 \times 10^5$ | >270 | >35 |
| Hybrid selections on B12 libraries (Hu-mu-hu) | 20 pM Selection | 5 pM Selection | 0 pM Selection | Selection window for 20 pM selection | Selection window for 5 pM selection |

TABLE 5-continued

Selection output titres. Round 3 selections. Phage output titres
were determined as described previously (Schofield et al, 2007).

| B12 VH | $1 \times 10^8$ | $7.7 \times 10^6$ | $<1 \times 10^5$ | $>1000$ | $>77$ |
| B12 VL | $1.3 \times 10^8$ | $1.8 \times 10^7$ | $<1 \times 10^5$ | $>1300$ | $>78$ |

ELISA Screen

An anti-FLAG capture ELISA was performed to screen for clones that had an improved affinity for mouse FBG binding compared with the parental antibodies.

E. coli clones harbouring scFv pSANG10 expression plasmids were induced in 96-well plates with auto-induction media as described previously (Schofield et al, 2007). E. coli supernatants were harvested for ELISA assays. ELISA used the DELFIA (dissociation enhanced lanthanide fluorescent immunoassay) system with Europium-labelled anti-FLAG antibody (Sigma, Aldrich, UK). Black immunosorb plates (Nunc) were coated overnight with anti-FLAG M2 antibody (Sigma, F3165, 5 µg/ml in PBS, 50 µl per well), in wells blocked by the addition of 2% milk powder, PBS (PBS-M, 300 µl per well). Plates were washed three times with PBS-T (PBS, 0.1% Tween-20) and three times with PBS followed by the addition of a 1:2 dilution of 96-well auto-induction culture supernatants containing expressed scFv in PBS-M (50 µl per well). The plates were incubated for 1 h, washed as above and biotinylated mouse or human rCd4-His-FBG (5 µg/ml in PBS-M, 50 µl) added to each well. Plates were incubated for a further 1 h, washed and Strepravidin-Eu added (Perkin Elmer, 1 µg/ml, PBS-M, 50 µl), incubated for 30 min, washed and DELFIA enhancement solution added (50 µl) and plates read on a Perkin Elmer Fusion plate reader (excitation=320 nm, emission 620 nm).

In this assay differences in scFv expression level are normalised because the expression levels of scFv in auto-induction cultures saturate the anti-FLAG coated wells. Therefore, the signals obtained in the assay reflect the amount of biotinylated rCd4-His-FBG bound after washing, which will be a function of the off-rate of that clone for mouse or human FBG. ELISA screening of the selection output from the B12 sub-library revealed clones with improved binding to mouse TNC FBG.

HTRF Screen

An HTRF-based competition assay was developed to screen for antibody variants with improved binding to human TNC FBG.

All samples and reagents were prepared in assay buffer (50 mM $NaPO_4$, 0.1% BSA, 0.4 M KF, pH 7.0) at 4× the stated concentration. 5 µl of each reagent was subsequently added to low volume 384-well assay plates (Greiner, 784075) to give a final reaction volume of 20 µl. IgG antibodies were labelled using the d2 labelling kit (CisBio, 62D2DPEA) as directed by the manufacturer. Streptavidin europium cryptate (CisBio, 610SAKLA, Lot #25C) was used at a final concentration of 1.8 ng active moiety (SA) per 20 µl reaction as recommended by the manufacturer. Biotinylated rCd4-His-FBG was prepared using EZ-link Sulfo-NHS-LC-Biotin reagent (Thermo Scientific, 21327) the extent of biotinylation was quantified using biotinylation fluorescence quantitation kit (Thermo Scientific, 46610). Where appropriate, supernatants containing scFv (prepared as described above for ELISA assays) were added to the 384-well assay plate at a final dilution of 1/20 (i.e. 1/5 dilution in assay buffer followed by addition of 5 µl diluted sample to the 20 µl FRET assay). The concentrations of d2-labelled B12 IgG used for screening were 1.25 nM. Unless otherwise stated, biotinylated rCd4-His-FBG (biotin: protein ratio=1.8:1) was present at either 2.2 nM (in assays using the 2A5 IgG antibody) or 1 nM (in experiments using B12 IgG). Samples were incubated for approximately 1 h at room temperature and the FRET signal was determined using a BMG Pherastar instrument: excitation=320 nm; emission=620 nm and 665 nm; integration start time=60 µs; integration time=500 µs; 100 flashes per well. For competition assays containing culture supernatant, biotinylated rCd4-His-FBG antigen was pre-incubated with streptavidin europium cryptate for 45 min prior to addition of reagents to the assay plate. All FRET signals are presented as ΔR, where R=(E665/E620×104) and ΔR=(Rsample−Rbackground fluorescence).

Culture supernatants containing unlabelled scFv clones from affinity selected mutant libraries were tested for inhibition of the interaction between FBG and the fluorophore-labelled parental IgG antibody. The relative ranking of clones exhibiting FRET signals within the useful range in both assays was broadly unchanged, indicating that they were competing for similar epitopes. Hence, all B12 scFv variants from affinity maturation selections were screened for their ability to inhibit the binding of B12 IgG molecules to human TNC FBG. The parental clones, expressed as scFvs in parallel with the affinity matured clones, were used as benchmarks.

ScFv were sequenced and a panel of clones with unique VH or VL CDR3 sequences was selected for further study in human IgG4 format, based on their binding to mouse and human TNC FBG in the ELISA and HTRF assays, respectively.

TABLE 6

HTRF screen for clones with improved affinity for human rCD4-FBG.

| CDR3 Library | Selection type | Total clones tested | % inhibition of FRET signal | | | | | | % inhibition by parent scFv | |
| --- | --- | --- | --- | --- | --- | --- | --- | --- | --- | --- |
| | | | 0-25% | 25-50% | 51-75% | 76-85% | 86-90% | 91-95% | ≥96% | 2A5 | B12 |
| B12 VH | 100 fM | 46 | 6 | 2 | 3 | 8 | 5 | 6 | 16 | 19 | 86 |
| B12 VH | Hybrid 5 pM | 46 | 3 | 3 | 5 | 5 | 3 | 9 | 18 | 19 | 86 |

Variants of antibody B12 showed ≥4-fold improvement for mouse FBG binding, and ≥91% inhibition of HTRF signal. In total, 31 clones fitting these criteria with unique CDR3 sequences were identified below.

TABLE 7

Heavy or light chain CDR3 sequences of clones identified with improved binding to mouse and human TNC FBG and chosen for conversion to human IgG format for further study.

| Library | Clone name | CDR sequence | | |
|---|---|---|---|---|
| B12 VH | 165_13_B1 | VMSSMEDAFDI | SEQ ID NO: | 12 |
| | 165_13_B6 | GQKGEGDTFDI | SEQ ID NO: | 14 |
| | 165_13_D1 | GTRGEGDTFDI | SEQ ID NO: | 16 |
| | 165_13_C3 | SYQSDEDAFDI | SEQ ID NO: | 18 |
| | 165_13_D4 | GTVGEGDTFDI | SEQ ID NO: | 24 |
| | 165_13_A4 | DKYPVLDTFDI | SEQ ID NO: | 26 |
| | 165_13_B3 | ALARGHDTFDI | SEQ ID NO: | 28 |
| | 165_13_E1 | DISAVMDVPQT | SEQ ID NO: | 30 |
| | 180_11_F5 | VMRTGLDTFDI | SEQ ID NO: | 32 |

These are heavy or light chain sequences of antibody clones that bind to human and mouse TNC FBG and thus have potential utility in the methods, uses, compositions and compounds of the present invention. For example, antibodies that bind TNF FBG having these CDR3 sequences may be useful in identifying, inhibiting the function of, detecting and purifying TNC or TNC FBG.

Conversion to IgG4 Format and Determination of Binding Kinetics

The 31 scFv of interest were sub-cloned into a human IgG4 expression vector for generation of antibodies as human IgG4 with a hinge-stabilising mutation (S241P; Angal et al, 1993). IgG4 antibodies were transiently expressed in HEK-293F cells and culture supernatants were screened using surface plasmon resonance spectroscopy for ranking of their off-rates for binding to human and mouse TNC FBG, and human TNR FBG. Briefly, surface plasmon resonance (SPR) experiments were performed using a BIAcore T100 instrument and followed the protocol according to the Human antibody capture kit protocol (GE, BR-1008-39). For off-rate screening, 10,000 response units (RU) of anti-human Fc IgG (GE, BR-1008-39) was immobilised on flow-cells (FC1 and FC2) of a Series 5 CM5 dextran sensor chip (BR-1005-30) using EDC/NHS cross-linking chemistry according to the amine coupling kit protocol (GE, BR-1000-50). Culture supernatants containing expressed IgG4 were diluted 1:2 with 2×PBS-T and injected into FC2 (flowrate 5 μl/min, 60 s contact time) to enable antibody capture at 25° C. Antibody capture levels ranged from 308 to 1975 RU depending on the expression level of the antibody in the supernatant.

A fixed concentration of antigen (15 nM of human and mouse TNC rCd4-His-FBG and 100 nM of human TNR rCd4-His-FBG) was injected with a flow-path via FC 1 (reference flow cell) and FC 2 (antibody capture flow cell), with a flow rate of 30 μl/min, and the association and dissociation phases measured over 1 and 5 min time periods, respectively. Regeneration of the binding surface employed 3M MgCl$_2$ with 30 s contact time. Off rates were determined by reference cell subtraction and fitting the sensogram experimental data assuming a 1:1 interaction using BIAevaluation software (GE, BR-1005-97). Results of the off-rate screen are summarised in the Table 8 below.

TABLE 8

Surface plasmon resonance screen for ranking of human IgG4 anti-FBG off-rates

| | kd (s$^{-1}$ × 10$^{-4}$) for rCD4-His-FBG | | |
|---|---|---|---|
| Clone name | Human TNC FBG | Mouse TNC FBG | Human TNR FBG |
| 165_13_C3 | 0.00095 | 0.033 | 120 |
| 162_02_C3 | 0.0149 | 20 | 6350 |
| B12 parent | 1.5 | 300 | 1001 |

Clones were ranked according to low off-rate for human and mouse TNC rCd4-His-FBG, and high-off rate for human TNR rCd4-His-FBG. The 3 highest-ranking antibodies from each library were prioritised for more detailed kinetic analysis as purified IgG4. These clones are shown in Table 9 below.

TABLE 9

Heavy chain CDR3 amino acid sequences of B12 mutants with improved FBG binding off-rate characteristics (bol-underlined shows the amino acids that were changed in B12 parent).

| Clone | VH CDR3 | | |
|---|---|---|---|
| B12 parent | DISAVPDTFDI | SEQ ID NO: | 5 |
| 165_13_B1 | VMSSMEDAFDI | SEQ ID NO: | 12 |
| 165_13_D1 | GTRGEGDTFDI | SEQ ID NO: | 16 |
| 165_13_C3 | SYQSDEDAFDI | SEQ ID NO: | 18 |

Detailed kinetic parameters were evaluated for the 9 prioritised IgG4 antibodies. Binding characteristics were determined for interaction with human, rat and dog TNC rCD4-His-FBG, and human TNR rCD4-His-FBG. Kinetic assays followed essentially the same protocols as for the off-rate determinations described above, with some modifications as follows. To improve the accuracy of kinetic parameter determination, anti-human Fc IgG was immobilised at lower levels (2229 RU), resulting in a corresponding reduction in the amount of anti-FBG IgG4 captured.

Purified anti-FBG IgG4 was diluted to a concentration of 3.5 nM in PBS, pH 7.4, 0.05% Tween-20 and injected into FC2 at a flow rate of 10 μl/min, 60 s contact time. This typically resulted in an average of 80 RU of antibody captured (range: 55 RU to 90 RU). Antigens were prepared by doubling dilution in PBS, pH 7.4, 0.05% Tween-20 (highest concentration 100 nM except mouse rCD4-His-FBG which was 7 nM). Assays were performed at 37° C. (30 μl/min, 120 s contact time; mouse rCD4-His-FBGFBG 10 μl/min, 60 s contact time), with both the flow cell and injection chamber equilibrated to this temperature. As before, kinetic parameters were determined by reference cell subtraction and fitting the sensogram experimental data assuming a 1:1 interaction using BIAevaluation software (GE, BR-1005-97).

All nine antibodies displayed improved binding to mouse TNC FBG domain compared to the non-affinity matured parent clones, and antibodies 165_13_B1, 165_13_C3, and 160_01_A4 exhibited sub-nanomolar $K_D$ values for binding to human TNC FBG, with >70-fold lower affinity to the human TNR FBG analogue:

TABLE 10

Anti-FBG IgG4 binding kinetic data determined by surface plasmon resonance at 37° C.

| Antibody | | rCD4-His-FBG | | $K_D$ | Ka | $K_d$ |
|---|---|---|---|---|---|---|
| IgG4 | Parent | Species | Tenascin | (nM) | $(M^{-1}s^{-1}) \times 10^4$ | $(s^{-1}) \times 10^{-4}$ |
| B12 | B12 | Human | TNC | 0.24 | 47.1 | 11.2 |
| | | Mouse | TNC | 4.5 | 30 | 13.8 |
| 165_13_B1 | B12 | Human | TNC | 0.26 | 72.7 | 18.8 |
| | | Mouse | TNC | 0.96 | 73.3 | 7.06 |
| | | Rat | TNC | 2.20 | 31.1 | 68.4 |
| | | Dog | TNC | 2.85 | 65.5 | 187 |
| | | Human | TNR | 94.4 | 12.2 | 1149 |
| 165_13_C3 | B12 | Human | TNC | 0.072 | 116 | 8.3 |
| | | Mouse | TNC | 0.46 | 97.2 | 4.45 |
| | | Rat | TNC | 1.22 | 38.9 | 47.3 |
| | | Dog | TNC | 1.80 | 59.7 | 108 |
| | | Human | TNR | 35.8 | 12.0 | 431 |

Example 7—Anti-FBG IgG4 Binding to Citrullinated FBG

The binding affinity of antibody B12 to citrullinated FBG was determined by surface plasmon resonance (SPR). B12 was expressed as a human IgG4 with the hinge-stabilising S241P mutation using the QMCF expression technology (Icosagen, Estonia) and purified by protein A affinity chromatography (MabSelect Sure; GE Healthcare).

Citrullination of human TNC FBG

Purified human His-FBG was citrullinated using either peptidylarginine deiminase 2 (PAD2; MQ-16.201-2.5, Modiquest, NL) or peptidylarginine deiminase 4 (PAD4; MQ-16.203-2.5, Modiquest, NL) according to the supplier's instructions. Briefly, His-FBG was diluted to 1 mg/ml in the supplied deimination buffer (0.1 M Tris-HCl pH 7.5, 10 mM $CaCl_2$, 5 mM dithiothreitol) and 250 µl mixed with 125 mU of either PAD2 or PAD4 enzyme followed by incubation at 37° C. for 2 h. Citrullination was confirmed by amino acid analysis of the enzymatically-treated samples. Aliquots of His-FBG in deimination buffer were incubated for 2 h at 37° C. in the absence of added PAD enzyme, for use as non-citrullinated control protein. Citrullinated and unmodified His-FBG proteins were used in SPR experiments as described below.

Surface Plasmon Resonance

SPR experiments were performed on a BIAcore 3000 instrument Anti-human IgG (GE Healthcare) was covalently coupled to the surface of a CM5 sensor chip using amino coupling chemistry. The amount of the coupled anti-human IgG expressed in RU units varied between 6500-7000 (6.5-7.0 ng/mm$^2$). B12-hIgG4 (1-13 nM) was attached to the immobilised anti-human IgG in HBS-EP buffer (10 mM Hepes, 0.15 M NaCl, 2.5 mM EDTA and 0.005% Tween-20) at 25° C. Binding of the His-FBG variants to the immobilised B12-hIgG4 was also measured in HBS-EP buffer at 25° C. The flow rate was 5 µl/min in the immobilization experiments and 20 µl/min for kinetic analyses. The sensor chip surface was regenerated using 3 M $MgCl_2$. Data were analysed using BIAevaluation program 4.1 (GE Healthcare).

Analysis of B12-IgG4 binding to citrullinated His-FBG revealed that the kinetic parameters were essentially unchanged when compared to values obtained for binding to unmodified His-FBG. These results indicate that anti-FBG antibodies of the B12 lineage would be expected to bind both citrullinated and non-citrullinated forms of TNC FBG in therapeutic or diagnostic applications:

TABLE 11

Kinetic parameters for interaction of B12-hIgG4 with the His-FBG variants. Each kinetic parameter represents the mean ± s.d. of 3 independent determinations.

| Analyte | $K_D$ (M) | $K_{on}$ $(M^{-1}s^{-1})$ | $K_{off}$ $(s^{-1})$ |
|---|---|---|---|
| His-FBG | $(1.7 \pm 0.3) \times 10^{-10}$ | $(4.1 \pm 0.6) \times 10^6$ | $(6.8 \pm 0.9) \times 10^{-4}$ |
| His-FBG + PAD2 | $(3.2 \pm 0.3) \times 10^{-10}$ | $(3.0 \pm 0.4) \times 10^6$ | $(9.6 \pm 0.8) \times 10^{-4}$ |
| His-FBG + PAD4 | $(3.2 \pm 0.7) \times 10^{-10}$ | $(2.6 \pm 0.6) \times 10^6$ | $(7.8 \pm 0.4) \times 10^{-4}$ |

Example 8—Detection of TNC FBG in Human RA Tissue Using Immunohistochemistry

Immunohistochemistry studies were performed to determine whether anti-FBG antibodies effectively recognise endogenous forms of the human TNC FBG protein in human tissue. Tenascin-C is expressed at sites of chronic inflammation and its localisation within the inflamed synovium of joints from individuals with rheumatoid arthritis has previously been demonstrated by immunohistochemistry using commercially available antibodies (Goh et al, 2010; Salter D M, 1993).

The B12 antibody was expressed as mouse IgG2a format using the QMCF expression technology (Icosagen, Estonia) and purified by Protein G affinity chromatography followed by Superdex 200 gel filtration. Control mouse IgG1 anti-tenascin-C antibody (Clone 4F10TT; Takara Clontech), which recognises an EGF domain of full-length human tenascin-C was used as a positive control comparator. Mouse IgG1 (Dako X0931) or IgG2a (Dako X0943) against an irrelevant bacterial antigen were used as control primary antibodies to determine the level of non-specific background staining with these isotypes. Frozen sections of human knee joint synovium from donors with confirmed RA diagnosis (Asterand, UK) were equilibrated to room temperature, fixed (10 min) in 1:1 v/v acetone/methanol, and transferred to wash buffer. Immunostaining was performed using a Dako Autostainer with Envision Flex reagents (Dako K8010) according to manufacturer's protocols. Briefly, fixed tissue slides were placed onto the automated stainer and blocked (peroxidase block, 5 min; protein block, 10 min, Dako X0909) before 30 min application of primary antibody (B12 or Clone 4F10TT; 1, 2, or 4 µg/me. In some controls, slides were not exposed to primary antibody. After washing, HRP-labelled goat anti-mouse secondary antibody was applied (20 min) and slides were washed again, followed by 10 min application of DAB+Chromogen. Slides were washed, counterstained with haematoxylin and coverslipped for microscopic visualisation of staining.

In cryosections of RA synovium that were fixed using acetone/methanol, the anti-TNC FBG B12 mouse IgG2a showed a very similar pattern of staining to that obtained with the positive control antibody Clone 4F10TT. Specific immunostaining was observed in the synovium, fibrous capsule, vasculature and within the interstitium. There was no staining within lymphoid aggregates. Some non-specific immunostaining was present in non-immune control treated tissues. These results confirm and extend previous reports of tenascin-C expression within RA synovium, demonstrating that B12 is an effective agent for binding endogenous tenascin-C at sites of inflammation and further indicating that FBG is an accessible target in RA.

Example 9—Antibody Sequences

CDRs in VH and VL sequences indicated by boxes.

```
Antibody B12
VH CDR1:         DYAMH                                       (SEQ ID NO: 3)
VH CDR2:         GISGSGGSTYYADSVKG                           (SEQ ID NO: 4)
VH CDR3:         DISAVPDTFDI                                 (SEQ ID NO: 5)
VH amino acid sequence:

QVQLVESGGGLVQPGRSLRLSCAASGFTFDDYAMHWVRQAPGKGLEWVSGI

SGSGGSTYYADSVKGRFTISRDNAKNSLYLQMNSLRAEDTALYYCAKDISA         (SEQ ID NO: 6)

VPDTFDIWGQGTMVTVSS

VL CDR1:         RASQYIQGFLN                                 (SEQ ID NO: 7)
VL CDR2:         DASNLET                                     (SEQ ID NO: 8)
VL CDR3:         QQSYSTPQT                                   (SEQ ID NO: 9)
VL amino acid sequence:

DIQMTQSPASLPTPVGDRVTITCRASQYIQGFLNWYQQKPGKAPKLLIYDA

SNLETGVPSRFSGSGSGTDFTLTISSLQPEDFATYYCQQSYSTPQTFGQGT         (SEQ ID NO: 10)

KVDIKR; or

DIQMTQSPASLPTPVGDRVTITCRASQYIQGFLNWYQQKPGKAPKLLIYDA

SNLETGVPSRFSGSGSGTDFTLTISSLQPEDFATYYCQQSYSTPQTFGQGT         (SEQ ID NO: 11)

KVDIK

Antibody B12*
VH CDR1:         DYAMH                                       (SEQ ID NO: 3)
VH CDR2:         GISGSGGSTYYADSVKG                           (SEQ ID NO: 4)
VH CDR3:         DISAVPDTFDI                                 (SEQ ID NO: 5)
VH amino acid sequence:
QVQLVESGGGLVQPGRSLRLSCAASGFTFDDYAMHWVRQAPGKGLEWVSGI
SGSGGSTYYADSVKGRFTISRDNAKNSLYLQMNSLRAEDTALYYCAKDISA
VPDTFDIWGQGTMVTVSS                                          (SEQ ID NO: 6)
VL CDR1:         RASQYIQGFLN                                 (SEQ ID NO: 7)
VL CDR2:         DASNLET                                     (SEQ ID NO: 8)
VL CDR3:         QQSYSTPQT                                   (SEQ ID NO: 9)
VL amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKR; or                                                  (SEQ ID NO: 22)
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIK, or                                                   (SEQ ID NO: 23)
a light chain amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC,                                                 (SEQ ID NO: 1)
Antibody 165 13 B1* (derived from B12)
VH CDR1:         DYAMH                                       (SEQ ID NO: 3)
VH CDR2:         GISGSGGSTYYADSVKG                           (SEQ ID NO: 4)
VH CDR3:         VMSSMEDAFDI                                 (SEQ ID NO: 12)
```

VH amino acid sequence:

QVQLVESGGGLVQPGRSLRLSCAASGFTFDDYAMHWVRQAPGKGLEWVSGI

SGSGGSTYYADSVKGRFTISRDNAKNSLYLQMNSLRAEDTALYYCAKVMSS  (SEQ ID NO: 13)

MEDAFDIWGQGTMVTVSS

| | | |
|---|---|---|
| VL CDR1: | RASQYIQGFLN | (SEQ ID NO: 7) |
| VL CDR2: | DASNLET | (SEQ ID NO: 8) |
| VL CDR3: | QQSYSTPQT | (SEQ ID NO: 9) |

VL amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKR; or                                                  (SEQ ID NO: 22)
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIK, or                                                   (SEQ ID NO: 23)
a light chain amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC.                                                 (SEQ ID NO: 1)

Antibody 165 13 B6* (derived from B12)

| | | |
|---|---|---|
| VH CDR1: | DYAMH | (SEQ ID NO: 3) |
| VH CDR2: | GISGSGGSTYYADSVKG | (SEQ ID NO: 4) |
| VH CDR3: | GQKGEGDTFDI | (SEQ ID NO: 14) |

VH amino acid sequence:

QVQLVESGGGLVQPGRSLRLSCAASGTFDDYAMHWVRQAPGKGLEWVSGI

SGSGGSTYYADSVKGRFTISRDNAKNSLYLQMNSLRAEDTALYYCAKGQKG  (SEQ ID NO: 15)

EGDTFDIWGQGTMVTVSS

| | | |
|---|---|---|
| VL CDR1: | RASQYIQGFLN | (SEQ ID NO: 7) |
| VL CDR2: | DASNLET | (SEQ ID NO: 8) |
| VL CDR3: | QQSYSTPQT | (SEQ ID NO: 9) |

VL amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKR; or                                                  (SEQ ID NO: 22)
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIK, or                                                   (SEQ ID NO: 23)
a light chain amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC.                                                 (SEQ ID NO: 1)

Antibody 165 13 D1 (derived from B12)

| | | |
|---|---|---|
| VH CDR1: | DYAMH | (SEQ ID NO: 3) |
| VH CDR2: | GISGSGGSTYYADSVKG | (SEQ ID NO: 4) |
| VH CDR3: | GTRGEGDTFDI | (SEQ ID NO: 16) |

VH amino acid sequence:

QVQLVESGGGLVQPGRSLRLSCAASGFTFDDYAMHWVRQAPGKGLEWVSGI

SGSGGSTYYADSVKGRFTISRDNAKNSLYLQMNSLRAEDTALYYCAKGTRG  (SEQ ID NO: 17)

EGDTFDIWGQGTMVTVSS

| | | |
|---|---|---|
| VL CDR1: | RASQYIQGFLN | (SEQ ID NO: 7) |
| VL CDR2: | DASNLET | (SEQ ID NO: 8) |
| VL CDR3: | QQSYSTPQT | (SEQ ID NO: 9) |

VL amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT

```
KVDIKR; or                                                        (SEQ ID NO: 22)
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIK,                                                            (SEQ ID NO: 23)
a light chain amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC.                                                       (SEQ ID NO: 1)
Antibody 165 13 C3 (derived from B12)
VH CDR1:         DYAMH                                            (SEQ ID NO: 3)
VH CDR2:         GISGSGGSTYYADSVKG                                (SEQ ID NO: 4)
VH CDR3:         SYQSDEDAFDI                                      (SEQ ID NO: 18)

VH amino acid sequence:

QVQLVESGGGLVQPGRSLRLSCAASGFTFDDYAMHWVRQAPGKGLEWVSGI

SGSGGSTYYADSVKGRFTISRDNAKNSLYLQMNSLRAEDTALYYCAKSYQS               (SEQ ID NO: 19)

DEDAFDIWGQGTMVTVSS

VL CDR1:         RASQYIQGFLN                                      (SEQ ID NO: 7)
VL CDR2:         DASNLET                                          (SEQ ID NO: 8)
VL CDR3:         QQSYSTPQT                                        (SEQ ID NO: 9)
VL amino acid sequence:

DIQMTQSPASLPTPVGDRVTITCRASQYIQGFLNWYQQKPGKAPKLLIYDA

SNLETGVPSRFSGSGSGTDFTLTISSLQPEDFATYYCQQSYSTPQTFGQGT               (SEQ ID NO: 10)

KVDIKR; or

DIQMTQSPASLPTPVGDRVTITCRASQYIQGFLNWYQQKPGKAPKLLIYDA

SNLETGVPSRFSGSGSGTDFTLTISSLQPEDFATYYCQQSYSTPQTFGQGT               (SEQ ID NO: 11)

KVDIK

Antibody 165 13 C3* (derived from B12)
VH CDR1:         DYAMH                                            (SEQ ID NO: 3)
VH CDR2:         GISGSGGSTYYADSVKG                                (SEQ ID NO: 4)
VH CDR3:         SYQSDEDAFDI                                      (SEQ ID NO: 18)
VH amino acid sequence:
QVQLVESGGGLVQPGRSLRLSCAASGFTFDDYAMHWVRQAPGKGLEWVSGI
SGSGGSTYYADSVKGRFTISRDNAKNSLYLQMNSLRAEDTALYYCAKSYQS
DEDAFDIWGQGTMVTVSS                                                (SEQ ID NO: 19)
VL CDR1:         RASQYIQGFLN                                      (SEQ ID NO: 7)
VL CDR2:         DASNLET                                          (SEQ ID NO: 8)
VL CDR3:         QQSYSTPQT                                        (SEQ ID NO: 9)
VL amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKR; or                                                        (SEQ ID NO: 22)
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIK, or                                                         (SEQ ID NO: 23)
a light chain amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC.                                                       (SEQ ID NO: 1)
Antibody 165 13 D4* (derived from B12)
VH CDR1:         DYAMH                                            (SEQ ID NO: 3)
VH CDR2:         GISGSGGSTYYADSVKG                                (SEQ ID NO: 4)
VH CDR3:         GTVGEGDTFDI                                      (SEQ ID NO: 24)

VH amino acid sequence:

QVQLVESGGGLVQPGRSLRLSCAASGFTFDDYAMHWVRQAPGKGLEWVSGI
```

```
SGSGGSTYYADSVKGRFTISRDNAKNSLYLQMNSLRAEDTALYYCAKGTVG      (SEQ ID NO: 25)

EGDTFDIWGQGTMVTVSS

VL CDR1:         RASQYIQGFLN                              (SEQ ID NO: 7)
VL CDR2:         DASNLET                                  (SEQ ID NO: 8)
VL CDR3:         QQSYSTPQT                                (SEQ ID NO: 9)
VL amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKR; or                                                (SEQ ID NO: 22)
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIK,                                                    (SEQ ID NO: 23)
a light chain amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC.                                               (SEQ ID NO: 1)
Antibody 165 13 A4* (derived from B12)
VH CDR1:         DYAMH                                    (SEQ ID NO: 3)
VH CDR2:         GISGSGGSTYYADSVKG                        (SEQ ID NO: 4)
VH CDR3:         DKYPVLDTFDI                              (SEQ ID NO: 26)

VH amino acid sequence:

QVQLVESGGGLVQPGRSLRLSCAASGFTFDDYAMHWVRQAPGKGLEWVSGI

SGSGGSTYYADSVKGRFTISRDNAKNSLYLQMNSLRAEDTALYYCAKDKYP      (SEQ ID NO: 27)

VLDTFDIWGQGTMVTVSS

VL CDR1:         RASQYIQGFLN                              (SEQ ID NO: 7)
VL CDR2:         DASNLET                                  (SEQ ID NO: 8)
VL CDR3:         QQSYSTPQT                                (SEQ ID NO: 9)
VL amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKR; or                                                (SEQ ID NO: 22)
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIK, or                                                 (SEQ ID NO: 23)
a light chain amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC.                                               (SEQ ID NO: 1)
Antibody 165 13 B3* (derived from B12)
VH CDR1:         DYAMH                                    (SEQ ID NO: 3)
VH CDR2:         GISGSGGSTYYADSVKG                        (SEQ ID NO: 4)
VH CDR3:         ALARGHDTFDI                              (SEQ ID NO: 28)

VH amino acid sequence:

QVQLVESGGGLVQPGRSLRLSCAASGFTFDDYAMHWVRQAPGKGLEWVSGI

SGSGGSTYYADSVKGRFTISRDNAKNSLYLQMNSLRAEDTALYYCAKALAR      (SEQ ID NO: 29)

GHDTFDIWGQGTMVTVSS

VL CDR1:         RASQYIQGFLN                              (SEQ ID NO: 7)
VL CDR2:         DASNLET                                  (SEQ ID NO: 8)
VL CDR3:         QQSYSTPQT                                (SEQ ID NO: 9)
VL amino acid sequence:
DIQMTQSPSSLSASVGDRVTITCRASQYIQGFLNWYQQKPGKAPLLIYDAS
NLETGVPSRFSGSGSGTDFTLTISSLQPEDFATYYCQQSYSTPQTFGQGTK
VDIKR; or                                                 (SEQ ID NO: 22)
DIQMTQSPSSLSASVGDRVTITCRASQYIQGFLNWYQQKPGKAPLLIYDAS
NLETGVPSRFSGSGSGTDFTLTISSLQPEDFATYYCQQSYSTPQTFGQGTK
VDIK, or                                                  (SEQ ID NO: 23)
a light chain amino acid sequence:
```

```
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC.                                              (SEQ ID NO: 1)
Antibody 165 13 E1* (derived from B12)
VH CDR1:         DYAMH                                   (SEQ ID NO: 3)
VH CDR2:         GISGSGGSTYYADSVKG                       (SEQ ID NO: 4)
VH CDR3:         DISAVMDVPQT                             (SEQ ID NO: 30)

VH amino acid sequence:

QVQLVESGGGLVQPGRSLRLSCAASGFTFDDYAMHWVRQAPGKGLEWVSGI

SGSGGSTYYADSVKGRFTISRDNAKNSLYLQMNSLRAEDTALYYCAKDISA      (SEQ ID NO: 31)

VMDVPQTWGQGTMVTSS

VL CDR1:         RASQYIQGFLN                             (SEQ ID NO: 7)
VL CDR2:         DASNLET                                 (SEQ ID NO: 8)
VL CDR3:         QQSYSTPQT                               (SEQ ID NO: 9)
VL amino acid sequence:
DIQMTQSPSSLSASVGDRVTITCRASQYIQGFLNWYQQKPGKAPLLIYDAS
NLETGVPSRFSGSGSGTDFTLTISSLQPEDFATYYCQQSYSTPQTFGQGTK
VDIKR; or                                                (SEQ ID NO: 22)
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIK, or                                                (SEQ ID NO: 23)
a light chain amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC,                                              (SEQ ID NO: 1)
Antibody 180 11 F5* (derived from B12)
VH CDR1:         DYAMH                                   (SEQ ID NO: 3)
VH CDR2:         GISGSGGSTYYADSVKG                       (SEQ ID NO: 4)
VH CDR3:         VMRTGLDTFDI                             (SEQ ID NO: 32)

VH amino acid sequence:

QVQLVESGGGLVQPGRSLRLSCAASGFTFDDYAMHWVRQAPGKGLEWVSGI

SGSGGSTYYADSVKGRFTISRDNAKNSLYLQMNSLRAEDTALYYCAKVMRT      (SEQ ID NO: 33)

GLDVPQTWGQGTMVTSS

VL CDR1:         RASQYIQGFLN                             (SEQ ID NO: 7)
VL CDR2:         DASNLET                                 (SEQ ID NO: 8)
VL CDR3:         QQSYSTPQT                               (SEQ ID NO: 9)
VL amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKR; or                                               (SEQ ID NO: 22)
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIK, or                                                (SEQ ID NO: 23)
a light chain amino acid sequence:
DIQMTQSPSSLSASVGDRVTITCRASQYIQGFLNWYQQKPGKAPKLLIYDA
SNLETGVPSRFSGSGSGTDFTLTISSLQPEDFATYYCQQSYSTPQTFGQGT
KVDIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC.                                              (SEQ ID NO: 1)
IgG4 165 13 C3 (constant region with hinge modifi-
cation as described in Angal 1993)
Reference: Angal S1, King DJ, Bodmer MW, Turner A,
Lawson AD, Roberts G, Pedley B, Adair JR. Mol
Immunol. 1993 Jan; 30(1):105-8.
QVQLVESGGGLVQPGRSLRLSCAASGFTFDDYAMHWVRQAPGKGLEWVSGI
SGSGGSTYYADSVKGRFTISRDNAKNSLYLQMNSLRAEDTALYYCAKYQS
DEDAFDIWGQGTMVTVSSASTKGPSVFPLAPCSRSTSESTAALGCLVKDYF
PEPVTVSWNSGALTSGVHTFPAVLQSSGLYSLSSVVTVPSSSLGTKTYTCN
VDHKPSNTKVDKRVESKYGPPCPPCPAPEFLGGPSVFLFPPKPKDTLMISR
TPEVTCVVVDVSQEDPEVQFNWYVDGVEVHNAKTKPREEQFNSTYRVVSVL
TVLHQDWLNGKEYKCKVSNKGLPSSIEKTISKAKGQPREPQVYTLPPSQEE
```

```
MTKNQVSLTCLVKGFPSDIAVEWESNGQPENNYKTTPPVLDSDGSFFLYSR        (SEQ ID NO: 34)
LTVDKSRWQEGNVFSCSVMHEALHNHYTQKSLSLSLGK
Antibody B12
Framework Germlined: VH amino acid sequence:

EVQLVESGGGLVQPGRSLRLSCAASGFTFD DYAMH WVRQAPGKGLEWVS GI

SGSGGSTYYADSVKY RFTISRDNAKNSLYLQMNSLRAEDTALYYCAK DISA    (SEQ ID NO: 35)

VPDVPQT WGQGTMVTVSS

CDRs changed as a result of the germlined sequence:
VH CDR2:          GISGSGGSTYYADSVKY                        (SEQ ID NO: 20)
```

Example 13—Activity of the C3 Antibody In Vitro

In order to confirm that the monoclonal antibody C3 (165_13_C3) acts by disrupting the binding of TNC-FBG to its receptor TLR4, first an in vitro binding assay was developed for TLR4 and Fc-His-FBG then the effect of pre-incubation of Fc-His-FBG with C3 was determined.

Recombinant human TLR4 (R&D systems) (1 ug/ml (14.6 nM)) in PBS (or PBS alone) was bound to a 96-well plate. After blocking (10% BSA) the indicated concentrations of Human Fc-His-FBG was added and detection was carried out by incubation of an anti-human IgG1 MAb (AbD Serotec, clone 2C11) at 1 ug/ml, an anti-mouse HRP conjugated secondary antibody (AbD Serotec, STAR13B) at 1 ug/ml, and TMB substrate. The results are shown in FIG. 1A, n=4 mean and SEM shown. This experiment shows that Fc-His-FBG binds TLR4 in vitro in a dose dependent manner.

Figure 1B:
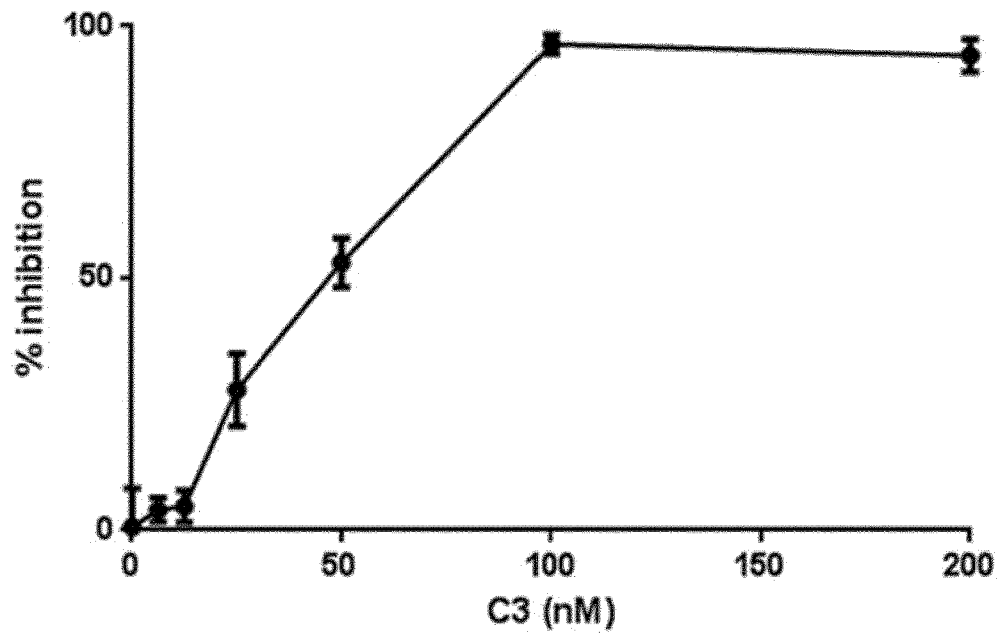

As shown in FIG. 1B, monoclonal Ab C3 disrupts the binding FBG and TLR4 in vitro. Recombinant human TLR4 in PBS (or PBS alone) was bound to a 96-well plate, after blocking recombinant human Fc-His-TNC-FBG (100 nM) which had been pre-incubated with C3 Mab or isotype control antibody was added. Detection was carried out by successive incubation of antibody directed against the Fc portion of the protein, an anti-mouse HRP conjugated secondary antibody and TMB substrate. The percentage inhibition in the C3 pre-incubated samples was calculated compared to the isotype control samples (IC50=44.5 nM). n=4.

Example 14—Anti-Inflammatory Effect of Antibodies B12 and C3

It was confirmed that the anti-TNC-FBG antibodies B12, and C3 (165_13_C3) have an anti-inflammatory effect in a biological system. To do this, human monocytes were isolated from peripheral blood (London blood bank) by Ficoll gradient and counter-flow centrifugation. The monocytes were then differentiated with 100 ng/ml M-CSF (Peprotec) for 5 days to produce M2 macrophages.

Figure 2A:
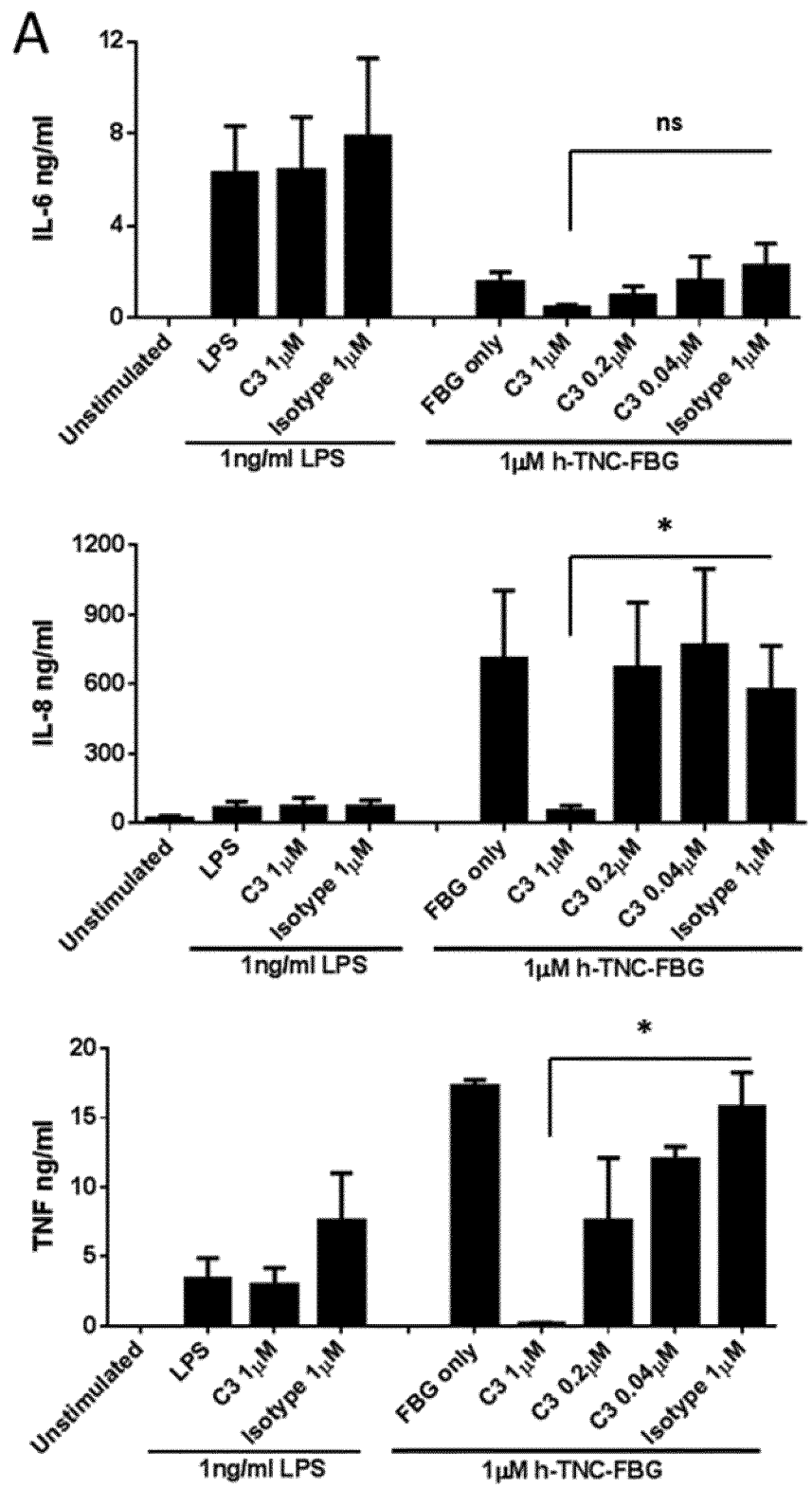
FIG. 2 (A) graphs showing effect on pro-inflammatory cytokine release by human M2 macrophages stimulated with recombinant human TNC-FBG after incubation with MAb C3. (B) graphs showing effect on pro-inflammatory cytokine release by human M2 macrophages stimulated with recombinant murine TNC-FBG after incubation with MAb C3. (C) graphs showing effect on pro-inflammatory cytokine release by human M2 macrophages stimulated with recombinant mutated Fc TNC-FBG after incubation with MAb C3, A4 or B12.

As shown by the results in FIG. 2A, recombinant human Fc-TNC FBG (1 uM) or LPS (Enzo) (1 ng/ml) was pre-incubated for 30 min at RT with MAb C3 (1, 0.2, and 0.04 uM) or isotype control (Eureka) MAb (1 uM) before being added in triplicate to Human M2 macrophage cultures. After 24 h supernatants were taken and subjected to IL-8, IL-6 and TNF cytokine ELISA (BD Biosciences), n=3. These results show that at 1 uM C3 greatly reduces the pro-inflammatory cytokine release by human M2 macrophages stimulated with TNC-FBG, this reduction is statistically significant for both IL-8 and TNF. As expected C3 has no effect on LPS-induced cytokine release.

FIG. 2B shows results from the experiment where recombinant murine Fc-TNC FBG (1 uM) was pre-incubated for 30 min at RT with MAb C3 (1, 0.2 and 0.04 uM) or isotype control MAb (Eureka) (1 uM) before being added in triplicate to Human M2 macrophage cultures. After 24 h supernatants were taken and subjected to cytokine ELISA. n=3 or over, mean and SEM shown. Again C3 at 1 uM greatly reduced the murine Fc-TNC-FBG-induced cytokine release by macrophages, indicating good cross-species reactivity of the antibody.

Figure 2C:
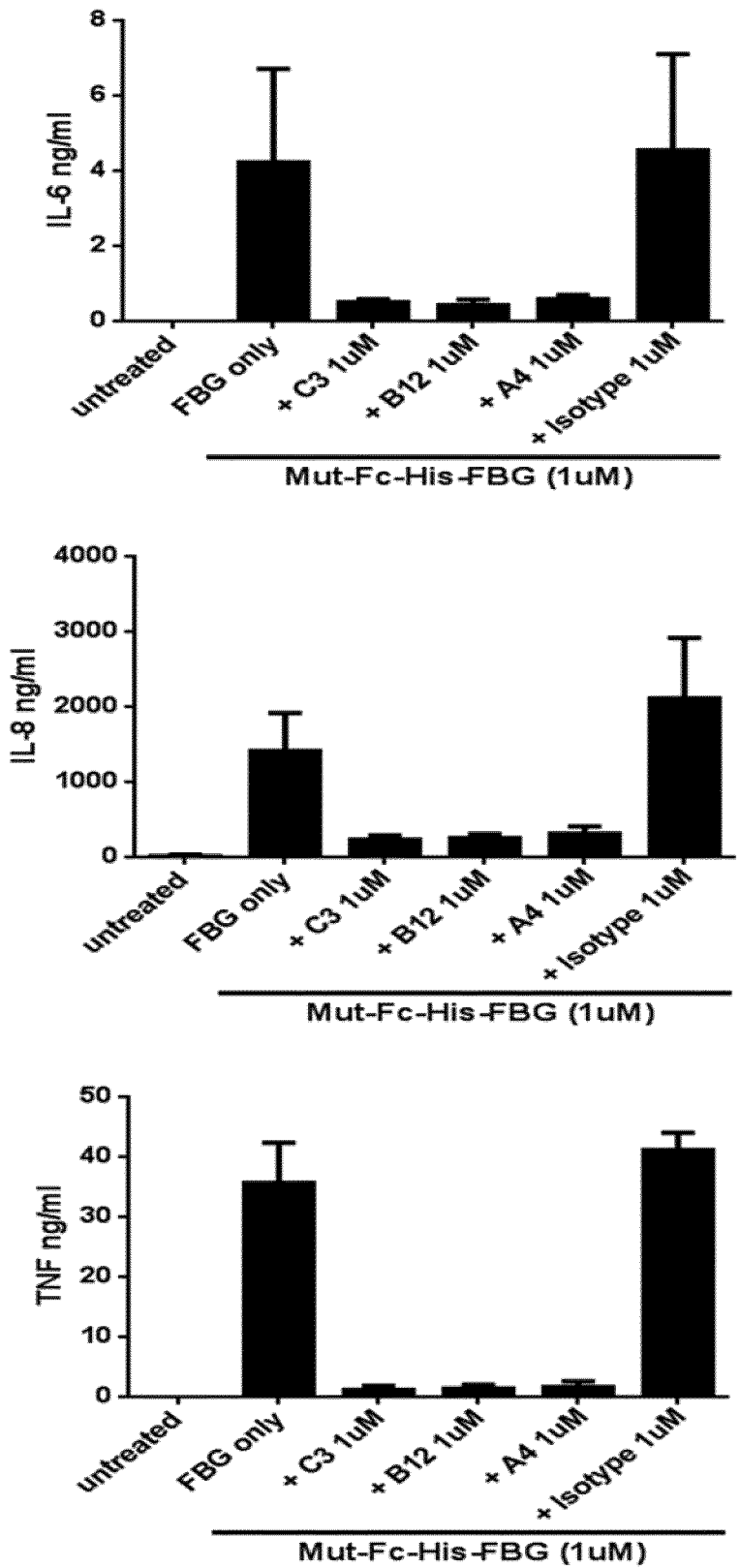

To confirm that the FBG-induced cytokine release was induced by the FBG rather than the Fc portion of the protein, a protein where the Fc portion is mutated to be inactive (Fc-Mut-FBG) was used, Anti-TNC-FBG antibodies, B12, C3 (165_13_C3) and A4 (160_01_A4) were also tested for activity against this molecule. Fc-Mut-FBG (1 uM) and C3, A4 or B12 (1 uM) were pre-incubated for 30 min at RT before being added to human M2 macrophage cultures. After 24 h supernatants were taken and subjected to cytokine ELISA. n=3, mean and SEM shown. Results are shown in FIG. 2C. This experiment confirms that Fc-His-FBG-induced cytokine synthesis is not due to the Fc portion signalling through Fc-receptors. Further, it shows that pre-incubation of the related antibodies B12 and A4, as well as C3 greatly reduce FBG-induced cytokine release by human M2 macrophages.

Figure 3A:
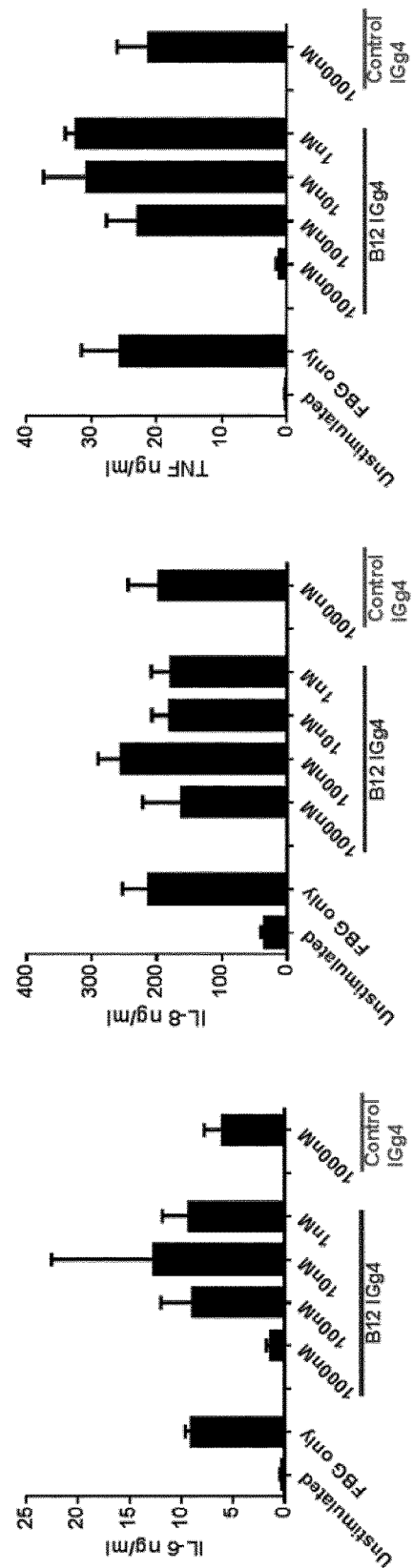
FIG. 3 (A) graphs showing effect on pro-inflammatory cytokine release by human M2 macrophages stimulated with recombinant human TNC-FBG after incubation with MAb B12. (B) graphs showing effect on pro-inflammatory cytokine release by human M2 macrophages stimulated with recombinant human TNC-FBG after incubation with MAb B12 at laboratory/larger scale.

FIG. 3A shows that Monoclonal antibody B12 reduces the production of pro-inflammatory cytokines by primary human macrophages stimulated with human TNC-FBG. In that experiment, recombinant Human tenascin-C FBG (1 uM) was pre-incubated for 30 min at RT with MAb B12 (1, 0.1, 0.01 or 0.001 uM) or isotype control MAb (1 uM) before being added in triplicate to Human M2 macrophage cultures. After 24 h supernatants were taken and subjected to cytokine ELISA, n=1. Here again we see that the B12 antibody pre-incubation reduces FBG-induced cytokine release, in this donor IL-8 gives a minimal response.

Figure 3B:
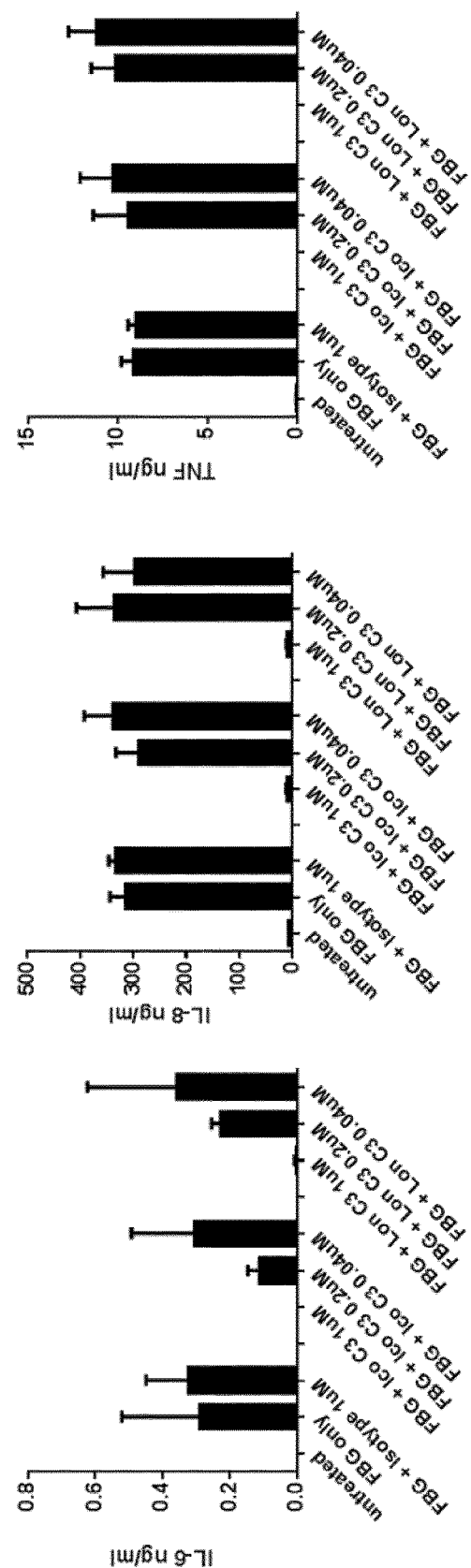

FIG. 3B shows that monoclonal antibody C3 produced at laboratory or larger scale show the same level of efficacy in blockade of FBG-induced cytokine synthesis by primary human macrophages.

To take the C3 antibody into animal studies, IgG4 B12 165-13-C3 product was cloned, expressed and purified at a leading contract manufacturing organisation using a commercial GS-CHO expression. cDNAs for the heavy and light chain variable regions were optimised for CHO expression and synthesised (with commercial signal sequences) by Life Technologies prior to cloning into the expression vectors.

CHO cells were transfected as pools and the highest expressing pool was taken forward into large-scale shake flask production (22 L—11×2 L in SL shake flasks). Proprietary feeds were administered on day 4 and 8 prior to harvesting the culture on day 12. Material was centrifuged prior to depth filtration and filter sterilisation. Approximately a 5.5 fold concentration of material was performed using tangential flow filtration (30 kDa molecular weight cut off) and the resulting concentrate was filter sterilised again prior to MabSelect SuRe purification. The product was eluted and product was neutralised and then concentrated/diafiltered to approximately 11 mg/mL in 20 mM NaOAc, pH 5.5, 150 mM NaCl. Reduced and non-reduced SDS-PAGE analysis together with size exclusion—HPLC showed material that was highly pure and greater than 98% monomer. Endotoxin was less than 0.1Eu per mg.

In this experiment the potency of the larger scale antibody batch was compared to the current smaller scale batch. Recombinant Human tenascin-C FBG (1 uM) was pre-incubated for 30 min at RT with MAb C3 (1, 0.2 and 0.04 uM) or isotype control MAb (1 uM) before being added in triplicate to Human M2 macrophage cultures. After 24 h supernatants were taken and subjected to cytokine ELISA. n=1, Ico=laboratory scale Lon=larger scale material. This experiment shows that both batches of antibodies show equal potency in the reduction of FBG-induced cytokine synthesis, i.e. the results are consistent irrespective of production.

Example 15—Monoclonal Antibody C3 (165_13_C3) Reduces the Production of Pro-Inflammatory Cytokines by RA Synovial Fibroblasts Stimulated with Human TNC-FBG It has been reported that synovial fibroblasts could be an important source of pro-inflammatory cytokine release in RA (R Bucala et al. (1991) Constitutive Production of Mitogenic and Inflammatory Cytokines by Rheumatoid Synovial Fibroblasts. J. Exp. Med. 173:569-574), it was therefore tested whether the C3 antibody also showed similar effects on FBG-induced cytokine release as in the macrophages.

Human RA fibroblasts were grown out of donor RA synovial tissue by digestion of the tissue in RPMI (Lonza) containing 0.5 mg/ml Liberase (Roche) and 0.2 mg/ml DNase (Roche) and incubation at 37° C. for 1-1.5 h. The resulting tissue was pipetted through a 200 µm nylon mesh; the material that did not pass through the mesh was put into a petri-dish containing RPMI with 10% FBS (Life technologies) and 1% pen/strep (Life technologies) and incubated at 37° C. for 5 days. After 5 days synovial fibroblasts grow out of the tissue and the remaining tissue was removed from the RA synovial fibroblast (RASF) culture which was subsequently maintained in DMEM (Lonza) containing 10% FBS and 1% pen/strep. For this experiment RASF were plated out at $1\times10^4$ cells/well. Recombinant Human TNC-FBG (1 uM) was pre-incubated for 30 min at RT with MAb C3 (1, 0.2 and 0.04 uM) or isotype control MAb (1 uM) before being added in triplicate to the synovial fibroblast cultures. After 24 h supernatants were taken and subjected to cytokine ELISA. n=1, mean and SEM shown (see FIG. 4).

These results indicate that C3 acts to reduce FBG induced pro-inflammatory cytokine release (both IL-8 and IL-6) in RA synovial fibroblasts, showing that this is a potential mechanism in multiple cell types found in the inflamed RA joint.

Example 16—Levels of Tenascin-C in Rat Model

Expression of tenascin-C in both mouse and rat CIA (collagen-induced arthritis) models was confirmed and disease activity shown to correlate with clinical score.

Figure 5:
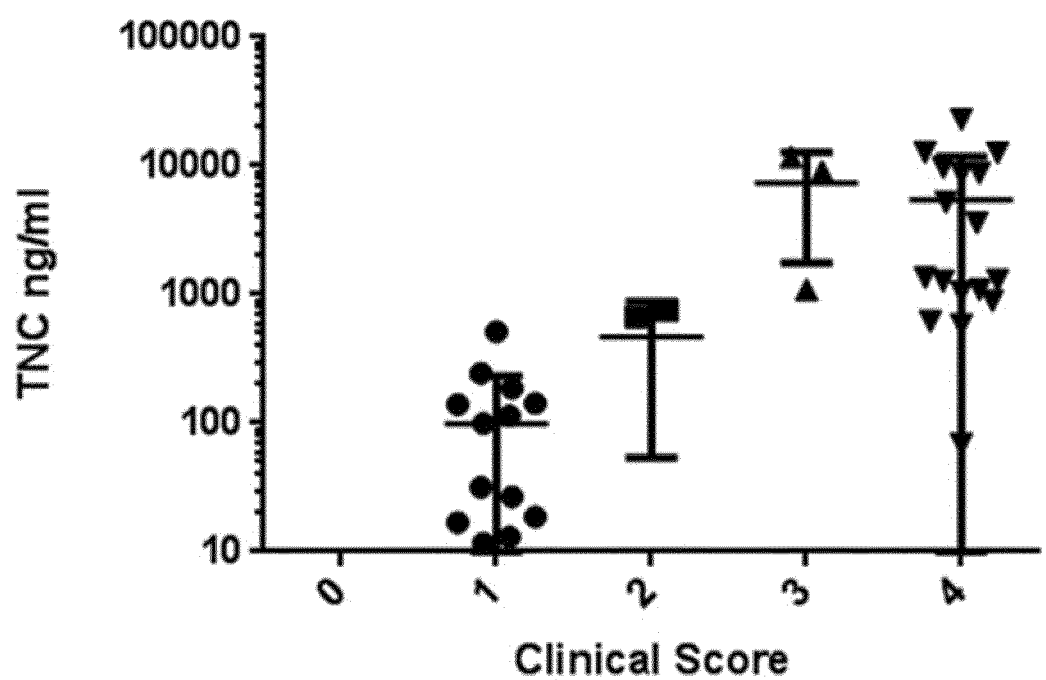
FIG. 5 Scatter-plot showing tenascin-C levels vs clinical score in synovial fluid wash-out from rat paws measured by ELISA.

FIG. 5 shows the results of an experiment measuring the levels of tenascin-C in synovial fluid wash-out from the paws of rats at the conclusion of two separate CIA studies (KWS). Tenascin-C levels were measured by ELISA (IBL, large (FN III-B) kit). The measured TNC level was then correlated with the clinical score associated with that paw designated by KWS. This experiment shows that the higher the clinical score for the paw, the higher the level of TNC seen in the synovial fluid from that paw. This indicates that the rat CIA model is a good model for testing of the C3 antibody.

Example 17—Evaluation of C3 Antibody in a Rat Model of Collagen-Induced Arthritis IgG4 C3 (165_13_C3) was tested for therapeutic activity in the standard rat collagen induced arthritis model. Adult male Lewis rats were randomly allocated to experimental groups and allowed to acclimatise for one week. On Day 0, animals were administered with 500 µl of a 1 mg/ml emulsion of type II bovine collagen in incomplete Freund's adjuvant (CII/IFA) by intra-dermal injection in the lower back. On Day 7, animals received a second injection of CII/IFA. Injections were performed under gas (isoflurane) anaesthesia. Treatments were administered according to the Administration Schedule shown below in Table 12.

TABLE 12

Administration Schedule

| Group | Treatment | Dose | Route | Regimen | Disease Induction |
|---|---|---|---|---|---|
| 1 | Vehicle (0.9% NaCl) | n/a | IV | Twice weekly* | Day 0, Day 7: CII/IFA, ID |
| 2 | Control IgG4 [1] | 10 mg/kg | IV | Day 0-End | |
| 3 | IgG4 165_13_C3 | 1 mg/kg | IV | | |
| 4 | IgG4 165_13_C3 | 3 mg/kg | IV | | |
| 5 | IgG4 165_13_C3 | 10 mg/kg | IV | | |

[1] Fully human IgG4 isotype control, preclinical grade, (ET904, Eureka Therapeutics),
n/a: not applicable,
IV: intra-venous injections,
ID: intra-dermal injections,
CII/IFA: Type II collagen and Incomplete Freund's Adjuvant emulsion,
*Day 0, Day 3, Day 7, Day 10, Day 14, Day 17, Day 21 and Day 24

From Day 7 until the end of the experiment, animals were scored three times per week for clinical signs of arthritis by an experimenter blind to the treatments. On Day 0, Day 14, Day 21 and Day 28, paw volumes were measured using a plethysmometer by an experimenter blind to the treatments.

Results

Non-Specific Clinical Observations

From Day 0 until the end of the experiment, animals were checked daily for non-specific clinical signs to include abnormal posture (hunched), abnormal coat condition (pilo-erection) and abnormal activity levels (reduced or increased activity). One animal in Group 6 (ID #6.9, antibody 10 mg/kg-treated) did not recover from the isoflurane anaesthesia on Day 21. Animals did not show any non-specific clinical signs such as abnormal posture, abnormal coat condition and abnormal activity levels. One animal in Group 1 (ID #1.10, vehicle-treated) was culled on Day 22, prior to the end of the experiment, due to the severity of the clinical signs of arthritis.

Clinical Scores

Figure 6:
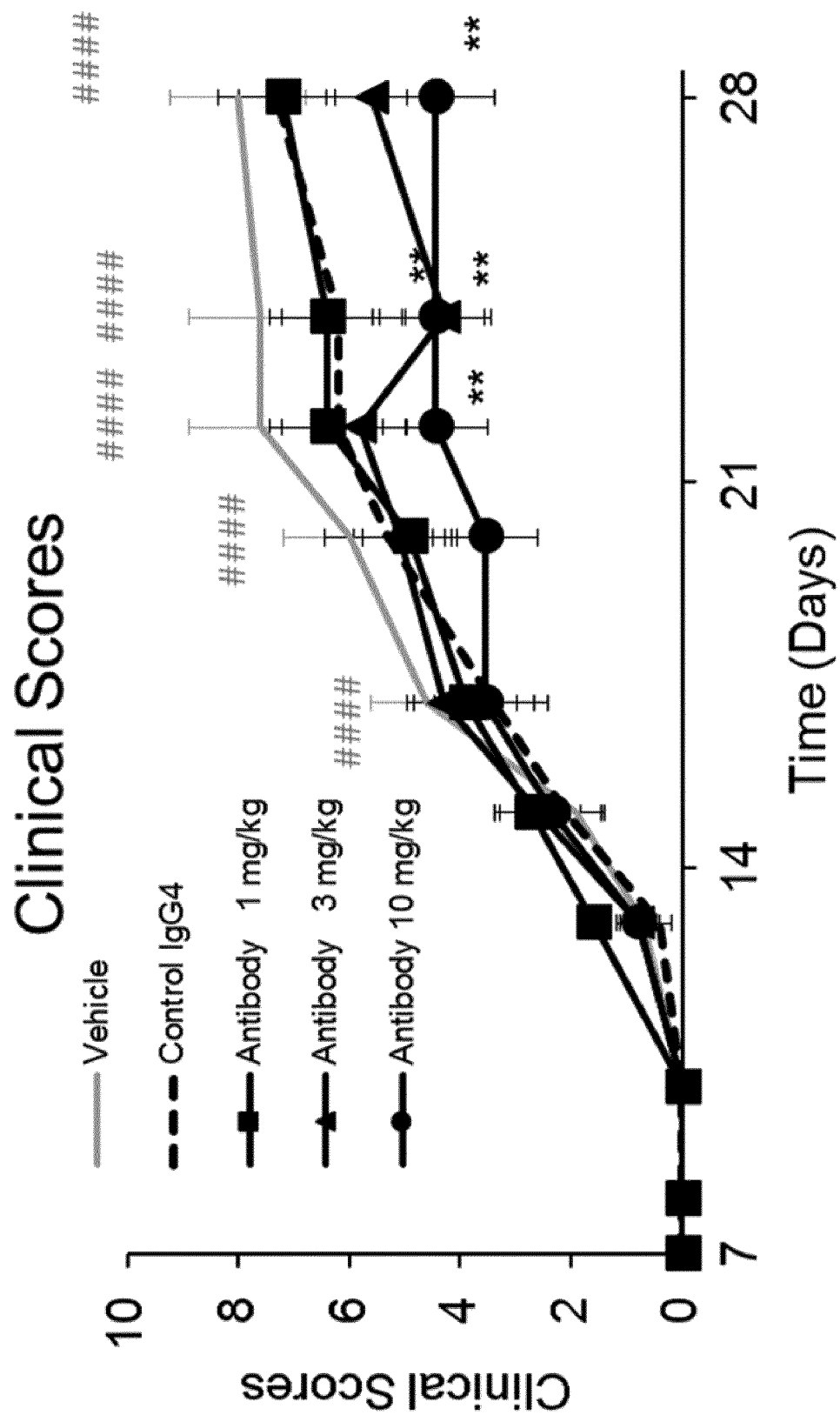
FIG. 6 Graph showing clinical score of rats over time following treatment with different dosages of C3 MAb.

From Day 7 until the end of the experiment, animals were scored three times per week for clinical signs of arthritis to include front and hind limb swelling. The experimenter was blind to the treatments. Each limb was scored on a five-point scale: (0) absence of swelling, (1) slight swelling and/or erythema, (2) mild swelling, (3) moderate swelling and (4) severe swelling and/or joint rigidity. A clinical score was calculated for each animal by adding the score of each limb. Data provided in FIG. 6 were graphed (Mean±SEM for each experimental group) and analysed by two-way ANOVA followed by Dunnett's post-test for multiple comparisons between experimental groups. The last recorded score for the vehicle-treated animal #1.10 was used after Day 22. Data recorded from animal #6.9 were excluded from the analysis. Clinical scores in the vehicle-treated group significantly increased from Day 17 until the end of the experiment on Day 28 when compared to the clinical scores measured on Day 7 ($p<0.0001$). Control IgG4 and IgG4 C3 1 mg/mL dose groups did not induce any significant difference when compared to the vehicle-treated group between Day 7 and the end of the experiment on Day 28. IgG4 C3 administered at 3 mg/kg, induced a significant reduction of the clinical scores when compared to the vehicle-treated group on Day 24 ($p<0.01$). IgG4 C3 administered at 10 mg/kg, induced a significant reduction of the clinical scores when compared to the vehicle-treated group from Day 22 until the end of the experiment on Day 28 ($p<0.01$).

Paw Volumes

Figure 7:
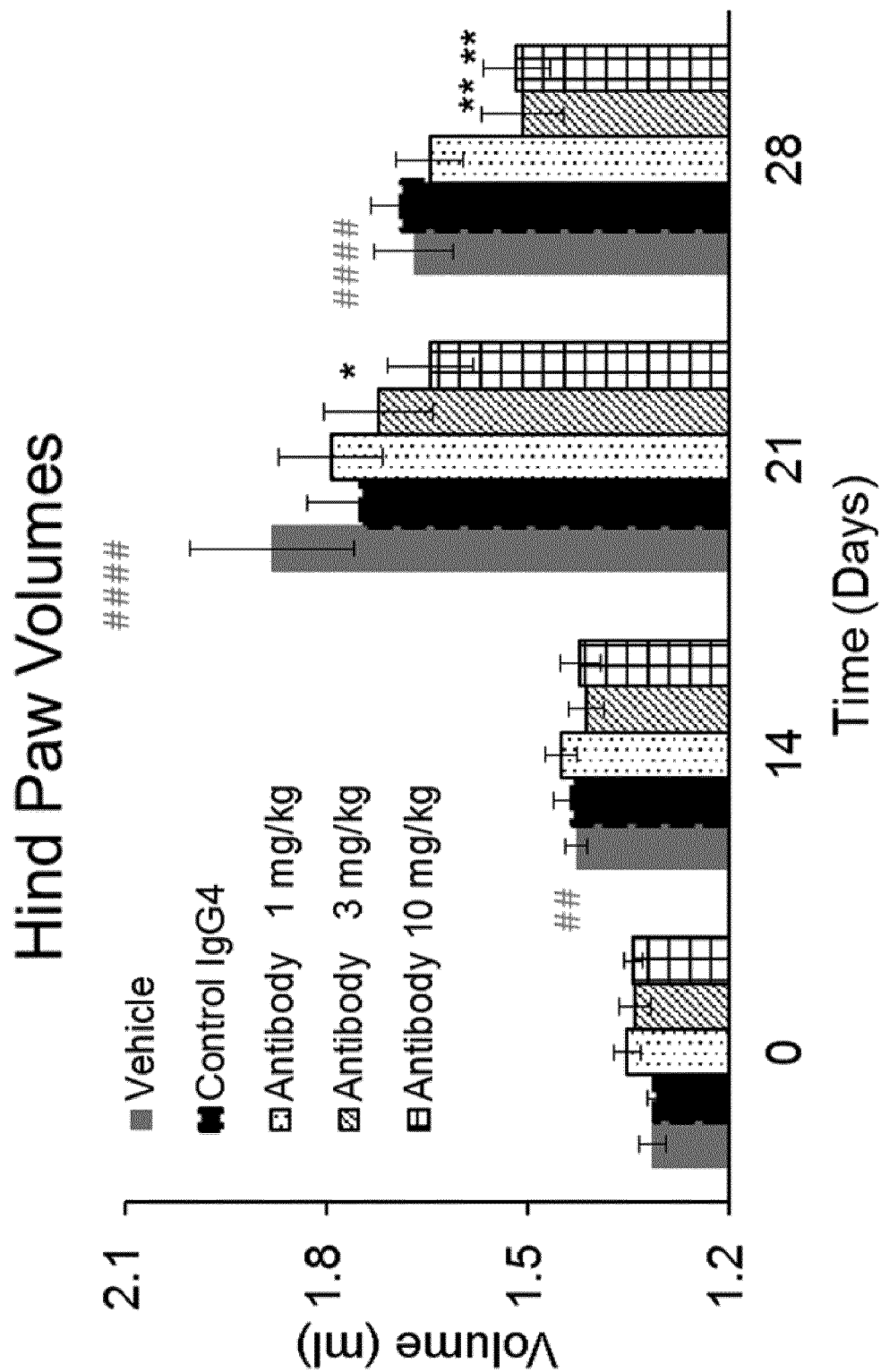
FIG. 7 Graph showing hind paw volumes of rats over time following treatment with different dosages of C3 MAb.
Figure 9:
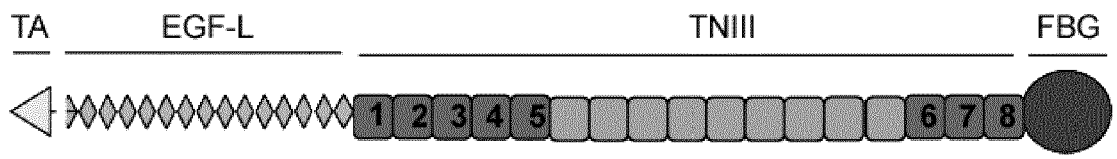
FIG. 9 (A) schematic diagram showing tenascin-C domain structure. (B) Legend.

On Day 0, Day 14, Day 21 and Day 28, hind paw volumes were measured using a plethysmometer (water-displacement device). Measurements were performed under gas (isoflurane) anaesthesia. The experimenter was blind to the treatment. Right and left hind paw volumes from each animal on each experimental day were averaged. FIG. 7 shows graphed data (Mean±SEM for each experimental group). Data were analysed by two-way ANOVA followed by Dunnett's post-test for multiple comparisons between experimental groups. The last recorded value for the vehicle-treated animal #1.10 was used on Day 28. Data recorded from animal #6.9 were excluded from the analysis.

Paw volumes measured in the vehicle-treated group increased significantly from Day 14 until the end of the experiment on Day 28 when compared to the paw volumes measured on Day 0 ($p<0.01$ on Day 14, $p<0.0001$ on Day 21 and Day 28). The control IgG4 and 1 mg/kg IgG4 C3 dose groups did not induced any difference in hind paw volumes when compared to the vehicle-treated group between Day 0 and Day 28. IgG4 C3 administered at 3 mg/kg induced a significant decrease of the hind paw volumes when compared to the vehicle-treated group on Day 28 ($p<0.01$). IgG4 C3 administered at 10 mg/kg induced a significant decrease of the hind paw volumes when compared to the vehicle-treated group on Day 21 ($p<0.05$) and Day 28 ($p<0.01$).

Conclusions

The test antibody, IgG4 C3 (165_13_C3), when administered at 3 mg/kg or 10 mg/kg, significantly reduced the severity of the clinical signs.

Example 18—Protocol for In Vivo Testing

Adult male Lewis rats randomly allocated to experimental groups and allowed to acclimatise for one week are employed. On Day 0, animals are administered with 500 μl of a 1 mg/ml emulsion of type II bovine collagen in incomplete Freund's adjuvant (CII/IFA) by intra-dermal injections in the lower back. On Day 7, animals receive a second injection of CII/IFA. Injections are performed under gas (isoflurane) anaesthesia. Treatments are administered according to the Administration Schedule below. From Day 0 until the end of the experiment, animals will be weighed three times per week. From Day 7 until the end of the experiment, animals are scored three times per week for clinical signs of arthritis by an experimenter blind to the treatments. On Day 0, Day 14, Day 21 and Day 28, paw volumes are measured using a plethysmometer by an experimenter blind to the treatments.

Treatment Groups and Dosages

Treatment groups and dosages are summarised in Table 13. Vehicle for test compounds was a 0.9% Sodium Chloride solution (Saline). Administration volume for intra-venous injection was 5 ml/kg. All groups are n=10.

TABLE 13

Treatment groups and dosages

| Group | Route | Treatment Regimen | Disease Induction |
|---|---|---|---|
| 1 Vehicle (Saline) | IV | Three times per week: Days 0, 2, 4, 7, 9, 11, 14, 16, 18, 21, 23, 25 | Day 0: CII/IFA Day 7: CII/IFA |
| 2 Methotrexate 1 mg/kg | IP | Twice weekly: Day 0-End | |
| 3 IgG4[1] 165_13_C3 (NSCT-121), 10 mg/kg | IV | Three times per week: Days 0, 2, 4, 7, 9, 11, 14, 16, 18, 21, 23, 25 | |
| 4 IgG4[1] 165_13_C3 (NSCT-121), 30 mg/kg | | Days 0,1, 4, 7, 10, 14, 17, 21, 24 | |
| 5 IgG4[1] 165_13_C3* (NSCT-141), 10 mg/kg | | Three times per week: Days 0, 2, 4, 7, 9, 11, 14, 16, 18, 21, 23, 25 | |

TABLE 13-continued

| | Treatment groups and dosages | | |
|---|---|---|---|
| Group | Route | Treatment Regimen | Disease Induction |
| 6 IgG4[1] 165_13_C3* (NSCT-141), 30 mg/kg | | Days 0, 1, 4, 7, 10, 14, 17, 21, 24 | | n/a: not applicable,
IV: intra-venous injection,
IP: intra-peritoneal injection,
CII: Type II collagen,
IFA: incomplete Freund's adjuvant,
[1]Hinge modified IgG4 (S241P; Angal etal, 1993).

Clinical Scores

From Day 7 until the end of the experiment, animals are scored three times per week for clinical signs of arthritis to include front and hind limb swelling. The experimenter is blind to the treatments. Each limb is scored on a five-point scale: (0) absence of swelling, (1) slight swelling and/or erythema, (2) mild swelling, (3) moderate swelling and (4) severe swelling and/or joint rigidity. A clinical score is calculated for each animal by adding the score of each limb. In the model methotrexate, which is a control, reduces clinical systems. The C3 antibody reduces clinical systems, the C3* antibody shows activity similar or greater than C3 in this model.

Example 19—Biacore Analysis of C3 and C3* Antibodies Human and Mouse TNC FBG and Human TNR FBG Kinetic Assay: Characterisation of Binding of Human, and Mouse TNC rCd4-his-FBG and Human TNR rCd4-his-FBG to NSCT Antibodies SPR experiments were performed to test whether the germline changes made in 165_13_C3* have retained the affinity or specificity of 165_13_C3. SPR experiments were performed using a BIAcore T200 instrument (GE Healthcare) according to the protocol of the Human antibody capture kit (GE, BR-1008-39).

For the kinetic assay ~1,500-1,900 response units (RU) of anti-human Fc IgG (GE, BR-1008-39) was immobilised in all flow-cells (FC1-4) on a Series S CM5 sensor chip (BR-1005-30) using EDC/NHS cross-linking chemistry according to the amine coupling kit protocol (GE, BR-1000-50). Purified NSCT antibody was diluted in HBS-P+ (Hepes pH 7.4, 150 mM NaCl, 0.05% Tween 20) running buffer to a concentration of 3.5 nM and injected into FC2 and FC4 (using a flowrate 10 μL/min and 115 s contact time) at 25° C. Antibody capture levels ranged typically from 70 RU (for TNR interactions) to 90 RU (for TNC interactions).

A 1:1 dilution series of antigen in HBS-P+ (30 nM of human and mouse TNC rCd4-His-FBG and 480 nM of human TNR rCd4-His-FBG) was injected with a flow-path via the reference flow cell (FC1 and FC3, respectively) and the antibody capture flow cell (FC2 and FC4, respectively) with a flow rate of 30 μl/min. The association and dissociation phases were measured over a 3.5 and 30 min time period, respectively, for human and mouse TNC rCd4-His-FBG, and 2 and 8 min time period for human TNR rCd4-His-FBG. For interaction analysis with human and mouse TNC rCD4-His-FBG regeneration of free capture antibody surfaces after each antigen injection was done by injection of 3 M MgCl2 for 60 s and for each sample injection a fresh NSCT antibody was captured. Carry over of antigen was prohibited by an extra needle wash step with 50% DMSO before every injection. Runs were performed at the more physiologically relevant temperature of 37° C. Kinetic parameters were determined by reference cell subtraction and fitting the sensorgram experimental data to a 1:1 interaction model using the BIAcore T200 Evaluation software version 2.0. Conclusion: 165_13_C3 and 165_13_C3* show comparable binding to the TNC FBG and TNR FBG proteins tested.

TABLE 14

Kinetic binding data for initial protein samples determined by surface plasmon resonance (SPR) spectroscopy at 37° C.

| | Protein | $K_D$(M) | Tmax (RU) | SA (%) | ka (1/Ms) | SE (ka) | kd (1/s) | SE (kd) | Chi$^2$ (RU$^2$) | U-value |
|---|---|---|---|---|---|---|---|---|---|---|
| C3 | hTNR | 5.27e−8 | 13 | 184 | 1.127e6 | 3.2e3 | 0.059 | 1.7e−4 | 0.0260 | 1 |
| | hTNC | 1.24e−9 | 17 | 298 | 3.398e6 | 6.4e2 | 0.0042 | 6.8e−7 | 0.214 | 1 |
| | mTNC | 4.33e−10 | 17 | 303 | 9.272e6 | 5.0e3 | 0.0040 | 2.3e−6 | 0.0801 | 1 |
| C3* | hTNR | 5.31e−8 | 15 | 233 | 1.108e6 | 1.0e3 | 0.058 | 4.2e−5 | 0.0656 | 1 |
| | hTNC | 4.43e−10 | 14 | 297 | 9.350e6 | 5.8e3 | 0.0041 | 2.7e−6 | 0.0750 | 1 |
| | mTNC | 6.70e−10 | 14 | 304 | 6.275e6 | 6.8e3 | 0.0042 | 2.2e−6 | 0.644 | 2 |

KD, equilibrium constant (M); T Rmax, theoretical maximal binding level of ligand in response units (RU); SA, surface activity in percent (%); ka, association constant (1/Ms); kd, dissociation constant (1/s); Chi$^2$, value is a statistical measure of the closeness of fit (typically <2), The U-value is an additional indicator of the parameter significance. This is a parameter that represents the uniqueness of the calculated rate constants and R max, determined by testing the dependence of fitting on correlated variations between selected variables. Lower values indicate greater confidence in the results. A high value (above about 10) indicates that the reported kinetic constants contain no useful information.

Example 20 Expression of 165_13_C3 and 165_13_C3* in a CHO-Pool Shake Flask Production 165_13_C3 and 165_13_C3* were cloned into a GS-CHO expression vector with a hinge modified IgG4 heavy chain constant region. Cell lines were generated and material expressed and purified as described in example 14. Antibody titre data from the cell culture supernatant prior to concentration and affinity purification is provided in table 15. Expression of IgG4 165_13_C3 * was more than three-fold higher than IgG4 165_13_C3.

TABLE 15

Titre from cell culture supernatant at the end of production

| Product | Lot Number | Culture Volume (L) | Titre (mg/L) |
| --- | --- | --- | --- |
| IgG4 165_13_C3* | 357-180516-1 | 10 | 375 |
| IgG4 165_13_C3 | Pooled 237-230115-01 and 237-260115-01 | 22 | 111 |
| IgG4 165_13_C3 | 443-231116-01 | 20 | 110 |

The invention claimed is:

1. An isolated human antibody or antigen-binding fragment thereof specific to a fibrinogen-like globe (FBG) domain of Tenascin C, wherein the antibody or antigen-binding fragment thereof comprises a VL sequence as shown in SEQ ID NO: 23, and a VH sequence with a CDRH1 of SEQ ID NO: 3, a CDRH2 of SEQ ID NO: 4 and a CDRH3 selected from SEQ ID NO: 5, 12, 14, 16, 18, 20, 24, 26, 28, 30 or 32.

2. The antibody or antigen-binding fragment thereof specific to a FBG domain of Tenascin C of claim 1, wherein the antibody or antigen-binding fragment thereof comprises a VL sequence as shown in SEQ ID NO: 22 and a VH sequence with a CDRH1 of SEQ ID NO: 3, a CDRH2 of SEQ ID NO: 4 and a CDRH3 of SEQ ID NO: 18.

3. The antibody or antigen-binding fragment of claim 1, comprising a VH sequence selected from SEQ ID NO: 6, 13, 15, 17, 19, 21, 25, 27, 29, 31, 33, 35 or a variant thereof wherein up to 5 amino acids in the sequence are changed.

4. The antibody or antigen-binding fragment of claim 3, comprising a VH sequence of SEQ ID NO: 19.

5. The antibody or antigen-binding fragment of claim 1, wherein the antibody or antigen-binding fragment is a Fab or Fab' fragment.

6. The antibody or antigen-binding fragment of claim 1, wherein the antibody or antigen-binding fragment is a full length antibody.

7. The antibody or antigen-binding fragment of claim 6, wherein the light chain has a sequence as shown in SEQ ID NO: 1.

8. The antibody or antigen-binding fragment of claim 6, wherein the heavy chain has a sequence as shown in SEQ ID NO: 2.

9. The antibody or antigen-binding fragment of claim 1, wherein the heavy chain has a sequence as shown in SEQ ID NO: 34.

10. A pharmaceutical composition comprising an antibody or antigen-binding fragment according to claim 1 and a pharmaceutically acceptable excipient, diluent or carrier.

11. A polynucleotide encoding the antibody or antigen-binding fragment of claim 1.

12. A vector comprising the polynucleotide of claim 11.

13. A host cell comprising the polynucleotide of claim 11.

14. A host cell comprising the vector of claim 12.

* * * * *

SEQUENCE LISTING

```
<160> NUMBER OF SEQ ID NOS: 99

<210> SEQ ID NO 1
<211> LENGTH: 214
<212> TYPE: PRT
<213> ORGANISM: Artificial Sequence
<220> FEATURE:
<223> OTHER INFORMATION: light chain amino acid sequence

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Thr Phe Gly Gln Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 446
<212> TYPE: PRT
<213> ORGANISM: Artificial Sequence
<220> FEATURE:
<223> OTHER INFORMATION: heavy chain amino acid sequence

<400> SEQUENCE: 2
```

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ser Tyr Gln Ser Asp Glu Asp Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Arg Leu Thr Val Asp Lys Ser Arg
                405                 410                 415
```

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly
        435                 440                 445

<210> SEQ ID NO 3
<211> LENGTH: 5
<212> TYPE: PRT
<213> ORGANISM: Artificial Sequence
<220> FEATURE:
<223> OTHER INFORMATION: CDHR1 amino acid sequence

<400> SEQUENCE: 3

Asp Tyr Ala Met His
1               5

<210> SEQ ID NO 4
<211> LENGTH: 17
<212> TYPE: PRT
<213> ORGANISM: Artificial Sequence
<220> FEATURE:
<223> OTHER INFORMATION: CDRH2 amino acid sequence

<400> SEQUENCE: 4

Gly Ile Ser Gly Ser Gly Gly Ser Thr Tyr Tyr Ala Asp Ser Val Lys
1               5                   10                  15

Gly

<210> SEQ ID NO 5
<211> LENGTH: 11
<212> TYPE: PRT
<213> ORGANISM: Artificial Sequence
<220> FEATURE:
<223> OTHER INFORMATION: Antibody B12/B12* VH CDR3 amino acid sequence

<400> SEQUENCE: 5

Asp Ile Ser Ala Val Pro Asp Thr Phe Asp Ile
1               5                   10

<210> SEQ ID NO 6
<211> LENGTH: 120
<212> TYPE: PRT
<213> ORGANISM: Artificial Sequence
<220> FEATURE:
<223> OTHER INFORMATION: VH amino acid sequence

<400> SEQUENCE: 6

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Ser Ala Val Pro Asp Thr Phe Asp Ile Trp Gly Gln
            100                 105                 110

Gly Thr Met Val Thr Val Ser Ser
        115                 120

```
<210> SEQ ID NO 7
<211> LENGTH: 11
<212> TYPE: PRT
<213> ORGANISM: Artificial Sequence
<220> FEATURE:
<223> OTHER INFORMATION: CDRL1 amino acid sequence

<400> SEQUENCE: 7

Arg Ala Ser Gln Tyr Ile Gln Gly Phe Leu Asn
1               5                   10

<210> SEQ ID NO 8
<211> LENGTH: 7
<212> TYPE: PRT
<213> ORGANISM: Artificial Sequence
<220> FEATURE:
<223> OTHER INFORMATION: CDRL2 amino acid sequence

<400> SEQUENCE: 8

Asp Ala Ser Asn Leu Glu Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Antibody CDRL3 amino acid sequence

<400> SEQUENCE: 9

Gln Gln Ser Tyr Ser Thr Pro Gln Thr
1               5

<210> SEQ ID NO 10
<211> LENGTH: 108
<212> TYPE: PRT
<213> ORGANISM: Artificial Sequence
<220> FEATURE:
<223> OTHER INFORMATION: VL amino acid sequence

<400> SEQUENCE: 10

Asp Ile Gln Met Thr Gln Ser Pro Ala Ser Leu Pro Thr Pro Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Thr Phe Gly Gln Gly Thr Lys Val Asp Ile Lys Arg
            100                 105

<210> SEQ ID NO 11
<211> LENGTH: 107
<212> TYPE: PRT
<213> ORGANISM: Artificial Sequence
<220> FEATURE:
<223> OTHER INFORMATION: VL amino acid sequence
```

<400> SEQUENCE: 11

Asp Ile Gln Met Thr Gln Ser Pro Ala Ser Leu Pro Thr Pro Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Thr Phe Gly Gln Gly Thr Lys Val Asp Ile Lys
            100                 105

<210> SEQ ID NO 12
<211> LENGTH: 11
<212> TYPE: PRT
<213> ORGANISM: Artificial Sequence
<220> FEATURE:
<223> OTHER INFORMATION: CDRH3 amino acid sequence

<400> SEQUENCE: 12

Val Met Ser Ser Met Glu Asp Ala Phe Asp Ile
1               5                   10

<210> SEQ ID NO 13
<211> LENGTH: 120
<212> TYPE: PRT
<213> ORGANISM: Artificial Sequence
<220> FEATURE:
<223> OTHER INFORMATION: VH amino acid sequence

<400> SEQUENCE: 13

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Val Met Ser Ser Met Glu Asp Ala Phe Asp Ile Trp Gly Gln
            100                 105                 110

Gly Thr Met Val Thr Val Ser Ser
            115                 120

<210> SEQ ID NO 14
<211> LENGTH: 11
<212> TYPE: PRT
<213> ORGANISM: Artificial Sequence
<220> FEATURE:
<223> OTHER INFORMATION: CDRH3 amino acid sequence

```
<400> SEQUENCE: 14

Gly Gln Lys Gly Glu Gly Asp Thr Phe Asp Ile
1               5                   10

<210> SEQ ID NO 15
<211> LENGTH: 120
<212> TYPE: PRT
<213> ORGANISM: Artificial Sequence
<220> FEATURE:
<223> OTHER INFORMATION: VH amino acid sequence

<400> SEQUENCE: 15

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Gln Lys Gly Glu Gly Asp Thr Phe Asp Ile Trp Gly Gln
            100                 105                 110

Gly Thr Met Val Thr Val Ser Ser
        115                 120

<210> SEQ ID NO 16
<211> LENGTH: 11
<212> TYPE: PRT
<213> ORGANISM: Artificial Sequence
<220> FEATURE:
<223> OTHER INFORMATION: CDRH3 amino acid sequence

<400> SEQUENCE: 16

Gly Thr Arg Gly Glu Gly Asp Thr Phe Asp Ile
1               5                   10

<210> SEQ ID NO 17
<211> LENGTH: 120
<212> TYPE: PRT
<213> ORGANISM: Artificial Sequence
<220> FEATURE:
<223> OTHER INFORMATION: VH amino acid sequence

<400> SEQUENCE: 17

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95
```

```
Ala Lys Gly Thr Arg Gly Glu Gly Asp Thr Phe Asp Ile Trp Gly Gln
            100                 105                 110

Gly Thr Met Val Thr Val Ser Ser
        115                 120
```

<210> SEQ ID NO 18
<211> LENGTH: 11
<212> TYPE: PRT
<213> ORGANISM: Artificial Sequence
<220> FEATURE:
<223> OTHER INFORMATION: CDRH3 amino acid sequence

<400> SEQUENCE: 18

```
Ser Tyr Gln Ser Asp Glu Asp Ala Phe Asp Ile
1               5                   10
```

<210> SEQ ID NO 19
<211> LENGTH: 120
<212> TYPE: PRT
<213> ORGANISM: Artificial Sequence
<220> FEATURE:
<223> OTHER INFORMATION: VH amino acid sequence

<400> SEQUENCE: 19

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ser Tyr Gln Ser Asp Glu Asp Ala Phe Asp Ile Trp Gly Gln
            100                 105                 110

Gly Thr Met Val Thr Val Ser Ser
        115                 120
```

<210> SEQ ID NO 20
<211> LENGTH: 17
<212> TYPE: PRT
<213> ORGANISM: Artificial Sequence
<220> FEATURE:
<223> OTHER INFORMATION: CDRH2 amino acid sequence - CDRs changed as
      result of the germlined sequence

<400> SEQUENCE: 20

```
Gly Ile Ser Gly Ser Gly Gly Ser Thr Tyr Tyr Ala Asp Ser Val Lys
1               5                   10                  15

Tyr
```

<210> SEQ ID NO 21

<400> SEQUENCE: 21

000

<210> SEQ ID NO 22

```
<211> LENGTH: 108
<212> TYPE: PRT
<213> ORGANISM: Artificial Sequence
<220> FEATURE:
<223> OTHER INFORMATION: VL amino acid sequence

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Thr Phe Gly Gln Gly Thr Lys Val Asp Ile Lys Arg
            100                 105

<210> SEQ ID NO 23
<211> LENGTH: 107
<212> TYPE: PRT
<213> ORGANISM: Artificial Sequence
<220> FEATURE:
<223> OTHER INFORMATION: VL amino acid sequence

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Thr Phe Gly Gln Gly Thr Lys Val Asp Ile Lys
            100                 105

<210> SEQ ID NO 24
<211> LENGTH: 11
<212> TYPE: PRT
<213> ORGANISM: Artificial Sequence
<220> FEATURE:
<223> OTHER INFORMATION: CDRH3 amino acid sequence

<400> SEQUENCE: 24

Gly Thr Val Gly Glu Gly Asp Thr Phe Asp Ile
1               5                   10

<210> SEQ ID NO 25
<211> LENGTH: 120
<212> TYPE: PRT
<213> ORGANISM: Artificial Sequence
<220> FEATURE:
```

<223> OTHER INFORMATION: VH amino acid sequence

<400> SEQUENCE: 25

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Thr Val Gly Glu Gly Asp Thr Phe Asp Ile Trp Gly Gln
            100                 105                 110

Gly Thr Met Val Thr Val Ser Ser
        115                 120

<210> SEQ ID NO 26
<211> LENGTH: 11
<212> TYPE: PRT
<213> ORGANISM: Artificial Sequence
<220> FEATURE:
<223> OTHER INFORMATION: CDRH3 amino acid sequence

<400> SEQUENCE: 26

Asp Lys Tyr Pro Val Leu Asp Thr Phe Asp Ile
1               5                   10

<210> SEQ ID NO 27
<211> LENGTH: 120
<212> TYPE: PRT
<213> ORGANISM: Artificial Sequence
<220> FEATURE:
<223> OTHER INFORMATION: VH amino acid sequence

<400> SEQUENCE: 27

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Lys Tyr Pro Val Leu Asp Thr Phe Asp Ile Trp Gly Gln
            100                 105                 110

Gly Thr Met Val Thr Val Ser Ser
        115                 120

<210> SEQ ID NO 28
<211> LENGTH: 11
<212> TYPE: PRT

<213> ORGANISM: Artificial Sequence
<220> FEATURE:
<223> OTHER INFORMATION: CDRH3 amino acid sequence

<400> SEQUENCE: 28

```
Ala Leu Ala Arg Gly His Asp Thr Phe Asp Ile
1               5                   10
```

<210> SEQ ID NO 29
<211> LENGTH: 120
<212> TYPE: PRT
<213> ORGANISM: Artificial Sequence
<220> FEATURE:
<223> OTHER INFORMATION: VH amino acid sequence

<400> SEQUENCE: 29

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Gly Ser Gly Gly Ser Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ala Leu Ala Arg Gly His Asp Thr Phe Asp Ile Trp Gly Gln
            100                 105                 110

Gly Thr Met Val Thr Val Ser Ser
        115                 120
```

<210> SEQ ID NO 30
<211> LENGTH: 11
<212> TYPE: PRT
<213> ORGANISM: Artificial Sequence
<220> FEATURE:
<223> OTHER INFORMATION: CDRH3 amino acid sequence

<400> SEQUENCE: 30

```
Asp Ile Ser Ala Val Met Asp Val Pro Gln Thr
1               5                   10
```

<210> SEQ ID NO 31
<211> LENGTH: 120
<212> TYPE: PRT
<213> ORGANISM: Artificial Sequence
<220> FEATURE:
<223> OTHER INFORMATION: VH amino acid sequence

<400> SEQUENCE: 31

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Gly Ser Gly Gly Ser Thr Tyr Tyr Ala Asp Ser Val
        50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Leu Tyr Tyr Cys
                    85                  90                  95

Ala Lys Asp Ile Ser Ala Val Met Asp Val Pro Gln Thr Trp Gly Gln
            100                 105                 110

Gly Thr Met Val Thr Val Ser Ser
        115                 120

<210> SEQ ID NO 32
<211> LENGTH: 11
<212> TYPE: PRT
<213> ORGANISM: Artificial Sequence
<220> FEATURE:
<223> OTHER INFORMATION: CDRH3 amino acid sequence

<400> SEQUENCE: 32

Val Met Arg Thr Gly Leu Asp Thr Phe Asp Ile
1               5                   10

<210> SEQ ID NO 33
<211> LENGTH: 120
<212> TYPE: PRT
<213> ORGANISM: Artificial Sequence
<220> FEATURE:
<223> OTHER INFORMATION: VH amino acid sequence

<400> SEQUENCE: 33

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Gly Ser Gly Gly Ser Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                    85                  90                  95

Ala Lys Val Met Arg Thr Gly Leu Asp Thr Phe Asp Ile Trp Gly Gln
            100                 105                 110

Gly Thr Met Val Thr Val Ser Ser
        115                 120

<210> SEQ ID NO 34
<211> LENGTH: 446
<212> TYPE: PRT
<213> ORGANISM: Artificial Sequence
<220> FEATURE:
<223> OTHER INFORMATION: Modified IgG4

<400> SEQUENCE: 34

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Gly Ser Gly Gly Ser Thr Tyr Tyr Ala Asp Ser Val
        50                  55                  60
```

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
             85                  90                  95

Ala Lys Ser Tyr Gln Ser Asp Glu Asp Ala Phe Asp Ile Trp Gly Gln
            100                 105                 110

Gly Thr Met Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 35
<211> LENGTH: 120
<212> TYPE: PRT
<213> ORGANISM: Artificial Sequence
<220> FEATURE:

<223> OTHER INFORMATION: Antibody B12 framework germlined VH amino acid
      sequence

<400> SEQUENCE: 35

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Tyr Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Ser Ala Val Pro Asp Thr Phe Asp Ile Trp Gly Gln
            100                 105                 110

Gly Thr Met Val Thr Val Ser Ser
        115                 120

<210> SEQ ID NO 36
<211> LENGTH: 8
<212> TYPE: PRT
<213> ORGANISM: Artificial Sequence
<220> FEATURE:
<223> OTHER INFORMATION: Hinge linker

<400> SEQUENCE: 36

Asp Lys Thr His Thr Cys Ala Ala
1               5

<210> SEQ ID NO 37
<211> LENGTH: 11
<212> TYPE: PRT
<213> ORGANISM: Artificial Sequence
<220> FEATURE:
<223> OTHER INFORMATION: Hinge linker

<400> SEQUENCE: 37

Asp Lys Thr His Thr Cys Pro Pro Cys Pro Ala
1               5                   10

<210> SEQ ID NO 38
<211> LENGTH: 18
<212> TYPE: PRT
<213> ORGANISM: Artificial Sequence
<220> FEATURE:
<223> OTHER INFORMATION: Hinge linker

<400> SEQUENCE: 38

Asp Lys Thr His Thr Cys Pro Pro Cys Pro Ala Thr Cys Pro Pro Cys
1               5                   10                  15

Pro Ala

<210> SEQ ID NO 39
<211> LENGTH: 25
<212> TYPE: PRT
<213> ORGANISM: Artificial Sequence
<220> FEATURE:
<223> OTHER INFORMATION: Hinge linker

<400> SEQUENCE: 39

Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25

<210> SEQ ID NO 40
<211> LENGTH: 30
<212> TYPE: PRT
<213> ORGANISM: Artificial Sequence
<220> FEATURE:
<223> OTHER INFORMATION: Hinge linker

<400> SEQUENCE: 40

Asp Lys Thr His Thr Cys Pro Pro Cys Pro Ala Gly Lys Pro Thr Leu
1               5                   10                  15

Tyr Asn Ser Leu Val Met Ser Asp Thr Ala Gly Thr Cys Tyr
            20                  25                  30

<210> SEQ ID NO 41
<211> LENGTH: 31
<212> TYPE: PRT
<213> ORGANISM: Artificial Sequence
<220> FEATURE:
<223> OTHER INFORMATION: Hinge linker

<400> SEQUENCE: 41

Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30

<210> SEQ ID NO 42
<211> LENGTH: 15
<212> TYPE: PRT
<213> ORGANISM: Artificial Sequence
<220> FEATURE:
<223> OTHER INFORMATION: Hinge linker

<400> SEQUENCE: 42

Asp Lys Thr His Thr Cys Cys Val Glu Cys Pro Pro Cys Pro Ala
1               5                   10                  15

<210> SEQ ID NO 43
<211> LENGTH: 26
<212> TYPE: PRT
<213> ORGANISM: Artificial Sequence
<220> FEATURE:
<223> OTHER INFORMATION: Hinge linker

<400> SEQUENCE: 43

Asp Lys Thr His Thr Cys Pro Arg Cys Pro Glu Pro Lys Ser Cys Asp
1               5                   10                  15

Thr Pro Pro Pro Cys Pro Arg Cys Pro Ala
            20                  25

<210> SEQ ID NO 44
<211> LENGTH: 11
<212> TYPE: PRT
<213> ORGANISM: Artificial Sequence
<220> FEATURE:
<223> OTHER INFORMATION: Hinge linker

<400> SEQUENCE: 44

Asp Lys Thr His Thr Cys Pro Ser Cys Pro Ala

```
1               5                   10
```

<210> SEQ ID NO 45
<211> LENGTH: 7
<212> TYPE: PRT
<213> ORGANISM: Artificial Sequence
<220> FEATURE:
<223> OTHER INFORMATION: Flexible linker

<400> SEQUENCE: 45

```
Ser Gly Gly Gly Gly Ser Glu
1               5
```

<210> SEQ ID NO 46
<211> LENGTH: 6
<212> TYPE: PRT
<213> ORGANISM: Artificial Sequence
<220> FEATURE:
<223> OTHER INFORMATION: Flexible linker

<400> SEQUENCE: 46

```
Asp Lys Thr His Thr Ser
1               5
```

<210> SEQ ID NO 47
<211> LENGTH: 6
<212> TYPE: PRT
<213> ORGANISM: Artificial Sequence
<220> FEATURE:
<223> OTHER INFORMATION: Flexible linker

<400> SEQUENCE: 47

```
Ser Gly Gly Gly Gly Ser
1               5
```

<210> SEQ ID NO 48
<211> LENGTH: 11
<212> TYPE: PRT
<213> ORGANISM: Artificial Sequence
<220> FEATURE:
<223> OTHER INFORMATION: Flexible linker

<400> SEQUENCE: 48

```
Ser Gly Gly Gly Gly Ser Gly Gly Gly Gly Ser
1               5                   10
```

<210> SEQ ID NO 49
<211> LENGTH: 16
<212> TYPE: PRT
<213> ORGANISM: Artificial Sequence
<220> FEATURE:
<223> OTHER INFORMATION: Flexible linker

<400> SEQUENCE: 49

```
Ser Gly Gly Gly Gly Ser Gly Gly Gly Gly Ser Gly Gly Gly Gly Ser
1               5                   10                  15
```

<210> SEQ ID NO 50
<211> LENGTH: 21
<212> TYPE: PRT
<213> ORGANISM: Artificial Sequence
<220> FEATURE:
<223> OTHER INFORMATION: Flexible linker

<400> SEQUENCE: 50

```
Ser Gly Gly Gly Gly Ser Gly Gly Gly Gly Ser Gly Gly Gly Gly Ser
1               5                   10                  15
```

```
Gly Gly Gly Gly Ser
            20

<210> SEQ ID NO 51
<211> LENGTH: 26
<212> TYPE: PRT
<213> ORGANISM: Artificial Sequence
<220> FEATURE:
<223> OTHER INFORMATION: Flexible linker

<400> SEQUENCE: 51

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser
            20                  25

<210> SEQ ID NO 52
<211> LENGTH: 11
<212> TYPE: PRT
<213> ORGANISM: Artificial Sequence
<220> FEATURE:
<223> OTHER INFORMATION: Flexible linker

<400> SEQUENCE: 52

Ala Ala Ala Gly Ser Gly Gly Ala Ser Ala Ser
1               5                   10

<210> SEQ ID NO 53
<211> LENGTH: 16
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 53

Ala Ala Ala Gly Ser Gly Xaa Gly Gly Gly Ser Gly Ala Ser Ala Ser
1               5                   10                  15

<210> SEQ ID NO 54
<211> LENGTH: 21
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 54

Ala Ala Ala Gly Ser Gly Xaa Gly Gly Gly Ser Xaa Gly Gly Gly Ser
1               5                   10                  15

Gly Ala Ser Ala Ser
            20

<210> SEQ ID NO 55
<211> LENGTH: 26
<212> TYPE: PRT
<213> ORGANISM: Artificial Sequence
```

```
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 55

Ala Ala Ala Gly Ser Gly Xaa Gly Gly Gly Ser Xaa Gly Gly Gly Ser
1               5                   10                  15

Xaa Gly Gly Gly Ser Gly Ala Ser Ala Ser
            20                  25

<210> SEQ ID NO 56
<211> LENGTH: 31
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 56

Ala Ala Ala Gly Ser Gly Xaa Gly Gly Gly Ser Xaa Gly Gly Gly Ser
1               5                   10                  15

Xaa Gly Gly Gly Ser Xaa Gly Gly Gly Ser Gly Ala Ser Ala Ser
            20                  25                  30

<210> SEQ ID NO 57
<211> LENGTH: 13
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 57

Ala Ala Ala Gly Ser Gly Xaa Ser Gly Ala Ser Ala Ser
1               5                   10

<210> SEQ ID NO 58
<211> LENGTH: 28
<212> TYPE: PRT
<213> ORGANISM: Artificial Sequence
<220> FEATURE:
<223> OTHER INFORMATION: Flexible linker
```

<400> SEQUENCE: 58

Pro Gly Gly Asn Arg Gly Thr Thr Thr Arg Arg Pro Ala Thr Thr
1               5                   10                  15

Thr Gly Ser Ser Pro Gly Pro Thr Gln Ser His Tyr
            20                  25

<210> SEQ ID NO 59
<211> LENGTH: 11
<212> TYPE: PRT
<213> ORGANISM: Artificial Sequence
<220> FEATURE:
<223> OTHER INFORMATION: Flexible linker

<400> SEQUENCE: 59

Ala Thr Thr Thr Gly Ser Ser Pro Gly Pro Thr
1               5                   10

<210> SEQ ID NO 60
<211> LENGTH: 6
<212> TYPE: PRT
<213> ORGANISM: Artificial Sequence
<220> FEATURE:
<223> OTHER INFORMATION: Flexible linker

<400> SEQUENCE: 60

Ala Thr Thr Thr Gly Ser
1               5

<210> SEQ ID NO 61
<211> LENGTH: 21
<212> TYPE: PRT
<213> ORGANISM: Artificial Sequence
<220> FEATURE:
<223> OTHER INFORMATION: Flexible linker

<400> SEQUENCE: 61

Glu Pro Ser Gly Pro Ile Ser Thr Ile Asn Ser Pro Pro Ser Lys Glu
1               5                   10                  15

Ser His Lys Ser Pro
            20

<210> SEQ ID NO 62
<211> LENGTH: 15
<212> TYPE: PRT
<213> ORGANISM: Artificial Sequence
<220> FEATURE:
<223> OTHER INFORMATION: Flexible linker

<400> SEQUENCE: 62

Gly Thr Val Ala Ala Pro Ser Val Phe Ile Phe Pro Pro Ser Asp
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Flexible linker

<400> SEQUENCE: 63

Gly Gly Gly Gly Ile Ala Pro Ser Met Val Gly Gly Gly Gly Ser
1               5                   10                  15

<210> SEQ ID NO 64

```
<211> LENGTH: 15
<212> TYPE: PRT
<213> ORGANISM: Artificial Sequence
<220> FEATURE:
<223> OTHER INFORMATION: Flexible linker

<400> SEQUENCE: 64

Gly Gly Gly Gly Lys Val Glu Gly Ala Gly Gly Gly Gly Gly Ser
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Flexible linker

<400> SEQUENCE: 65

Gly Gly Gly Gly Ser Met Lys Ser His Asp Gly Gly Gly Gly Ser
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Flexible linker

<400> SEQUENCE: 66

Gly Gly Gly Gly Asn Leu Ile Thr Ile Val Gly Gly Gly Gly Ser
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Flexible linker

<400> SEQUENCE: 67

Gly Gly Gly Gly Val Val Pro Ser Leu Pro Gly Gly Gly Gly Ser
1               5                   10                  15

<210> SEQ ID NO 68
<211> LENGTH: 12
<212> TYPE: PRT
<213> ORGANISM: Artificial Sequence
<220> FEATURE:
<223> OTHER INFORMATION: Flexible linker

<400> SEQUENCE: 68

Gly Gly Glu Lys Ser Ile Pro Gly Gly Gly Gly Ser
1               5                   10

<210> SEQ ID NO 69
<211> LENGTH: 18
<212> TYPE: PRT
<213> ORGANISM: Artificial Sequence
<220> FEATURE:
<223> OTHER INFORMATION: Flexible linker

<400> SEQUENCE: 69

Arg Pro Leu Ser Tyr Arg Pro Pro Phe Pro Phe Gly Phe Pro Ser Val
1               5                   10                  15

Arg Pro
```

```
<210> SEQ ID NO 70
<211> LENGTH: 18
<212> TYPE: PRT
<213> ORGANISM: Artificial Sequence
<220> FEATURE:
<223> OTHER INFORMATION: Flexible linker

<400> SEQUENCE: 70

Tyr Pro Arg Ser Ile Tyr Ile Arg Arg His Pro Ser Pro Ser Leu
1               5                   10                  15

Thr Thr

<210> SEQ ID NO 71
<211> LENGTH: 18
<212> TYPE: PRT
<213> ORGANISM: Artificial Sequence
<220> FEATURE:
<223> OTHER INFORMATION: Flexible linker

<400> SEQUENCE: 71

Thr Pro Ser His Leu Ser His Ile Leu Pro Ser Phe Gly Leu Pro Thr
1               5                   10                  15

Phe Asn

<210> SEQ ID NO 72
<211> LENGTH: 18
<212> TYPE: PRT
<213> ORGANISM: Artificial Sequence
<220> FEATURE:
<223> OTHER INFORMATION: Flexible linker

<400> SEQUENCE: 72

Arg Pro Val Ser Pro Phe Thr Phe Pro Arg Leu Ser Asn Ser Trp Leu
1               5                   10                  15

Pro Ala

<210> SEQ ID NO 73
<211> LENGTH: 18
<212> TYPE: PRT
<213> ORGANISM: Artificial Sequence
<220> FEATURE:
<223> OTHER INFORMATION: Flexible linker

<400> SEQUENCE: 73

Ser Pro Ala Ala His Phe Pro Arg Ser Ile Pro Arg Pro Gly Pro Ile
1               5                   10                  15

Arg Thr

<210> SEQ ID NO 74
<211> LENGTH: 18
<212> TYPE: PRT
<213> ORGANISM: Artificial Sequence
<220> FEATURE:
<223> OTHER INFORMATION: Flexible linker

<400> SEQUENCE: 74

Ala Pro Gly Pro Ser Ala Pro Ser His Arg Ser Leu Pro Ser Arg Ala
1               5                   10                  15

Phe Gly

<210> SEQ ID NO 75
<211> LENGTH: 18
<212> TYPE: PRT
<213> ORGANISM: Artificial Sequence
```

<220> FEATURE:
<223> OTHER INFORMATION: Flexible linker

<400> SEQUENCE: 75

Pro Arg Asn Ser Ile His Phe Leu His Pro Leu Leu Val Ala Pro Leu
1               5                   10                  15
Gly Ala

<210> SEQ ID NO 76
<211> LENGTH: 18
<212> TYPE: PRT
<213> ORGANISM: Artificial Sequence
<220> FEATURE:
<223> OTHER INFORMATION: Flexible linker

<400> SEQUENCE: 76

Met Pro Ser Leu Ser Gly Val Leu Gln Val Arg Tyr Leu Ser Pro Pro
1               5                   10                  15
Asp Leu

<210> SEQ ID NO 77
<211> LENGTH: 18
<212> TYPE: PRT
<213> ORGANISM: Artificial Sequence
<220> FEATURE:
<223> OTHER INFORMATION: Flexible linker

<400> SEQUENCE: 77

Ser Pro Gln Tyr Pro Ser Pro Leu Thr Leu Thr Leu Pro Pro His Pro
1               5                   10                  15
Ser Leu

<210> SEQ ID NO 78
<211> LENGTH: 18
<212> TYPE: PRT
<213> ORGANISM: Artificial Sequence
<220> FEATURE:
<223> OTHER INFORMATION: Flexible linker

<400> SEQUENCE: 78

Asn Pro Ser Leu Asn Pro Pro Ser Tyr Leu His Arg Ala Pro Ser Arg
1               5                   10                  15
Ile Ser

<210> SEQ ID NO 79
<211> LENGTH: 17
<212> TYPE: PRT
<213> ORGANISM: Artificial Sequence
<220> FEATURE:
<223> OTHER INFORMATION: Flexible linker

<400> SEQUENCE: 79

Leu Pro Trp Arg Thr Ser Leu Leu Pro Ser Leu Pro Leu Arg Arg Arg
1               5                   10                  15
Pro

<210> SEQ ID NO 80
<211> LENGTH: 18
<212> TYPE: PRT
<213> ORGANISM: Artificial Sequence
<220> FEATURE:
<223> OTHER INFORMATION: Flexible linker

<400> SEQUENCE: 80

```
Pro Pro Leu Phe Ala Lys Gly Pro Val Gly Leu Leu Ser Arg Ser Phe
1               5                   10                  15

Pro Pro
```

<210> SEQ ID NO 81
<211> LENGTH: 18
<212> TYPE: PRT
<213> ORGANISM: Artificial Sequence
<220> FEATURE:
<223> OTHER INFORMATION: Flexible linker

<400> SEQUENCE: 81

```
Val Pro Pro Ala Pro Val Val Ser Leu Arg Ser Ala His Ala Arg Pro
1               5                   10                  15

Pro Tyr
```

<210> SEQ ID NO 82
<211> LENGTH: 17
<212> TYPE: PRT
<213> ORGANISM: Artificial Sequence
<220> FEATURE:
<223> OTHER INFORMATION: Flexible linker

<400> SEQUENCE: 82

```
Leu Arg Pro Thr Pro Arg Val Arg Ser Tyr Thr Cys Cys Pro Thr
1               5                   10                  15

Pro
```

<210> SEQ ID NO 83
<211> LENGTH: 18
<212> TYPE: PRT
<213> ORGANISM: Artificial Sequence
<220> FEATURE:
<223> OTHER INFORMATION: Flexible linker

<400> SEQUENCE: 83

```
Pro Asn Val Ala His Val Leu Pro Leu Leu Thr Val Pro Trp Asp Asn
1               5                   10                  15

Leu Arg
```

<210> SEQ ID NO 84
<211> LENGTH: 18
<212> TYPE: PRT
<213> ORGANISM: Artificial Sequence
<220> FEATURE:
<223> OTHER INFORMATION: Flexible linker

<400> SEQUENCE: 84

```
Cys Asn Pro Leu Leu Pro Leu Cys Ala Arg Ser Pro Ala Val Arg Thr
1               5                   10                  15

Phe Pro
```

<210> SEQ ID NO 85
<211> LENGTH: 11
<212> TYPE: PRT
<213> ORGANISM: Artificial Sequence
<220> FEATURE:
<223> OTHER INFORMATION: Rigid linker

<400> SEQUENCE: 85

```
Gly Ala Pro Ala Pro Ala Ala Pro Ala Pro Ala
1               5                   10
```

```
<210> SEQ ID NO 86
<211> LENGTH: 4
<212> TYPE: PRT
<213> ORGANISM: Artificial Sequence
<220> FEATURE:
<223> OTHER INFORMATION: Rigid linker

<400> SEQUENCE: 86

Pro Pro Pro Pro
1

<210> SEQ ID NO 87
<211> LENGTH: 22
<212> TYPE: DNA
<213> ORGANISM: Artificial Sequence
<220> FEATURE:
<223> OTHER INFORMATION: Primer 2561

<400> SEQUENCE: 87
ggtacctcgc gaatgcatct ag                                              22

<210> SEQ ID NO 88
<211> LENGTH: 20
<212> TYPE: DNA
<213> ORGANISM: Artificial Sequence
<220> FEATURE:
<223> OTHER INFORMATION: Primer 2562

<400> SEQUENCE: 88
catgcaggcc tctgcagtcg                                                 20

<210> SEQ ID NO 89
<211> LENGTH: 58
<212> TYPE: DNA
<213> ORGANISM: Artificial Sequence
<220> FEATURE:
<223> OTHER INFORMATION: Primer 2565

<400> SEQUENCE: 89 tttttccat ggcccagatt ggactcctgt acccttccc caaagattgc tctcaggc         58

<210> SEQ ID NO 90
<211> LENGTH: 56
<212> TYPE: DNA
<213> ORGANISM: Artificial Sequence
<220> FEATURE:
<223> OTHER INFORMATION: Primer 2566

<400> SEQUENCE: 90 tttttccat ggcccagatt ggactcctgt acccttccc tcgcgactgc tcacag           56

<210> SEQ ID NO 91
<211> LENGTH: 53
<212> TYPE: DNA
<213> ORGANISM: Artificial Sequence
<220> FEATURE:
<223> OTHER INFORMATION: Primer 2567C

<400> SEQUENCE: 91 tttttggat cccatcatca tcaccatcac ttccccaaag attgctctca ggc             53

<210> SEQ ID NO 92
<211> LENGTH: 39
<212> TYPE: DNA
<213> ORGANISM: Artificial Sequence
<220> FEATURE:
```

<223> OTHER INFORMATION: Primer 2570

<400> SEQUENCE: 92 tttttttaagc ttttattacg cccgtttacg ccgaccctc          39

<210> SEQ ID NO 93
<211> LENGTH: 71
<212> TYPE: DNA
<213> ORGANISM: Artificial Sequence
<220> FEATURE:
<223> OTHER INFORMATION: Primer 2567

<400> SEQUENCE: 93 tttttttggat cccatcatca tcaccatcac attggactcc tgtacccctt ccccaaagat    60
tgctctcagg c                                                         71

<210> SEQ ID NO 94
<211> LENGTH: 51
<212> TYPE: DNA
<213> ORGANISM: Artificial Sequence
<220> FEATURE:
<223> OTHER INFORMATION: Primer 2569C

<400> SEQUENCE: 94 tttttttggat cccatcatca tcaccatcac ttccctcgcg actgctcaca g             51

<210> SEQ ID NO 95
<211> LENGTH: 39
<212> TYPE: DNA
<213> ORGANISM: Artificial Sequence
<220> FEATURE:
<223> OTHER INFORMATION: Primer 2571

<400> SEQUENCE: 95 tttttttaagc ttttattacg cccgtttccg ccgaccttc           39

<210> SEQ ID NO 96
<211> LENGTH: 69
<212> TYPE: DNA
<213> ORGANISM: Artificial Sequence
<220> FEATURE:
<223> OTHER INFORMATION: Primer 2568C

<400> SEQUENCE: 96 tttttttggat cccatcatca tcaccatcac attggactcc tgtacccctt ccctcgcgac    60
tgctcacag                                                            69

<210> SEQ ID NO 97
<211> LENGTH: 39
<212> TYPE: DNA
<213> ORGANISM: Artificial Sequence
<220> FEATURE:
<223> OTHER INFORMATION: Primer 2574

<400> SEQUENCE: 97 tttttttggat cccatcatca tcaccatcac taataaaag          39

<210> SEQ ID NO 98
<211> LENGTH: 38
<212> TYPE: DNA
<213> ORGANISM: Artificial Sequence
<220> FEATURE:
<223> OTHER INFORMATION: Primer 2575

<400> SEQUENCE: 98

```
tttttttaagc ttttattagt gatggtgatg atgatggg                               38

<210> SEQ ID NO 99
<211> LENGTH: 40
<212> TYPE: DNA
<213> ORGANISM: Artificial Sequence
<220> FEATURE:
<223> OTHER INFORMATION: Primer 2580

<400> SEQUENCE: 99 tttttttctcg agcatcatca tcaccatcac attggactcc                              40
```